(12) United States Patent
Gopalakrishnan et al.

(10) Patent No.: US 8,759,504 B2
(45) Date of Patent: Jun. 24, 2014

(54) CHOLINERGIC/SEROTONINERGIC RECEPTOR AND USES THEREOF

(75) Inventors: Murali Gopalakrishnan, Libertyville, IL (US); Jinhe Li, Long Grove, IL (US); Steven C. Cassar, Kenosha, WI (US); John Malysz, Columbia, SC (US); David J. Anderson, Lake Bluff, IL (US); Earl J. Gubbins, Libertyville, IL (US); Daniel C. Bertrand, Geneva (CH)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/367,102

(22) Filed: Feb. 6, 2012

(65) Prior Publication Data

US 2012/0219967 A1    Aug. 30, 2012

Related U.S. Application Data

(63) Continuation-in-part of application No. 12/146,088, filed on Jun. 25, 2008, now abandoned.

(60) Provisional application No. 60/946,583, filed on Jun. 27, 2007.

(51) Int. Cl.
   *C12N 15/62*    (2006.01)
   *G01N 33/567*   (2006.01)
   *C07K 14/705*   (2006.01)

(52) U.S. Cl.
   USPC ......... 536/23.4; 435/7.21; 435/69.7; 530/350

(58) Field of Classification Search
   None
   See application file for complete search history.

(56) References Cited

PUBLICATIONS

Dinklo et al., Desensitization Characteristics of the Human alpha7nAChR/5HT3A Chimera Receptor, Feb. 2006, J. Mol. Neurosci. 30(1-2):109-110.*
Arendash G.W., et al., "Improved Learning and Memory in Aged Rats with Chronic Administration of the Nicotinic Receptor Agonist GTS-21," Brain Research, 1995, vol. 674 (2), pp. 252-259.
Bettany J.H., et al., "Ventral Hippocampal Alpha 7 Nicotinic Receptor Blockade and Chronic Nicotine Effects on Memory Performance in the Radial-Arm Maze," Pharmacology, Biochemistry, and Behavior, 2001, vol. 70 (4), pp. 467-474.
Briggs C.A., et al., "Ion Channels—Ligand Gated ," Comprehensive Medicinal Chemistry, 2006, vol. 2, pp. 877-918.
Craig P.J., et al., "Stable Expression and Characterisation of a Human Alpha 7 Nicotinic Subunit Chimera: a Tool for Functional High-Throughput Screening," European Journal of Pharmacology, 2004, vol. 502 (1-2), pp. 31-40.
Curzon P., et al, "Antisense Knockdown of the Rat Alpha7 Nicotinic Acetylcholine Receptor Produces Spatial Memory Impairment," Neuroscience Letters, 2006, vol. 410 (1), pp. 15-19.
Eisele J.L., et al., "Chimaeric Nicotinic-Serotonergic Receptor Combines Distinct Ligand Binding and Channel Specificities," Nature, 1993, vol. 366 (6454), pp. 479-483.
Felix R., et al., "Nicotinic Antagonist Administration into the Ventral Hippocampus and Spatial Working Memory in Rats," Neuroscience, 1997, vol. 81 (4), pp. 1009-1017.
Gronlien J.H., et al., "Distinct Profiles of Alpha7 nAChR Positive Allosteric Modulation Revealed by Structurally Diverse Chemotypes," Molecular Pharmacology, 2007, vol. 72 (3), pp. 715-724.
Hajos M., et al., "The Selective Alpha7 Nicotinic Acetylcholine Receptor Agonist PNU-282987 [N-{(3R)-1-Azabicyclo {2.2.2} oct-3-yl)-4-Chlorobenzamide Hydrochloride) Enhances GABAergic Synaptic Activity in Brain Slices and Restores Auditory Gating Deficits in Anesthetized," Journal of Pharmacology and Experimental Therapeutics, 2005, vol. 312 (3), pp. 1213-1222.
Hurst R.S., et al., "A Novel Positive Allosteric Modulator of the Alpha7 Neuronal Nicotinic Acetylcholine Receptor: in vitro and in vivo Characterization," Journal of Neuroscience, 2005, vol. 25 (17), pp. 4396-4405.
International Preliminary Report on Patentability and Written Opinion for Application No. PCT/US2008/068264, mailed on Aug. 3, 2010, 10 pages.
International Search Report for PCT Application No. PCT/US2008/068264, mailed on Jul. 23, 2010, 4 pages.
Levin E.D., "Nicotine Effects on Working Memory: Neural Substrates and Transmitter Interactions," Behavioural Pharmacology, 1999, vol. 10 (Suppl. 1), pp. 857-858.
Quick M.W., et al., "Desensitization of Neuronal Nicotinic Receptors," Journal of Neurobiology, 2002, vol. 53 (4), pp. 457-478.
Ren K., et al., "Multiple Calcium Channels and Kinases Mediate Alpha7 Nicotinic Receptor Neuroprotection in PC12 Cells," Journal of Neurochemistry, 2005, vol. 94 (4), pp. 926-933.
Richardson B.P., et al., "Identification of Serotonin M-receptor Subtypes and their Specific Blockade by a new Class of Drugs," Nature, 1985, vol. 316 (6024), pp. 126-131.
Roman J., et al., "Nicotine and Fibronectin Expression in Lung Fibroblasts: Implications for Tobacco-Rlated Lung tissue Remodeling," The FASEB Journal, 2004, vol. 18 (12), pp. 1436-1438.
Shaw S., et al., "Janus Kinase 2, An Early Target of Alpha 7 Nicotinic Acetylcholine Receptor-Mediated Neuroprotection Against Abeta-(1-42) Amyloid," The Journal of Biological Chemistry, 2002, vol. 277 (47), pp. 44920-44924.
Van Kampen M., et al., "Ar-R 17779 Improves Social Recognition in Rate by Activation of Nicotinic Alpha7 Receptors," Psychopharmacology, 2004, vol. 172 (4), pp. 375-383.
Zwart R., et al., "5-Hydroxyindole Potentiates Human Alpha 7 Nicotinic Receptor-Mediated Responses and Enhances Acetylcholine-Induced Glutamate Release in Cerebellar Slices," Neuropharmacology, 2002, vol. 43 (3), pp. 374-384.

* cited by examiner

*Primary Examiner* — John Ulm
(74) *Attorney, Agent, or Firm* — Lisa V. Mueller; Michael Best & Friedrich LLP

(57) ABSTRACT

The present invention describes new cholinergic/serotoninergic chimeric receptors and provides methods and compositions suitable for screening for ligands such as agonists, antagonists and allosteric modulators of α7 nicotinic acetylcholine receptors.

10 Claims, 20 Drawing Sheets

Genistein preferentially potentiates chimera 2 and not chimera 1

CHOLINERGIC/SEROTONINERGIC RECEPTOR AND USES THEREOF

CROSS REFERENCE TO RELATED APPLICATIONS

This is a continuation-in-part to U.S. patent application Ser. No. 12/146,088, filed Jun. 25, 2008, which claims priority to U.S. Provisional Appl. No. 60/946,583 filed on Jun. 27, 2007, each of which are fully incorporated herein by reference.

FIELD AND BACKGROUND OF THE INVENTION

The present invention relates to alpha-7 nicotinic acetylcholine receptor (α7 nAChR) chimeric receptors containing one or more regions homologous to a nicotinic cholinergic receptor and a serotoninergic receptor for measuring α7 nAChR function and methods and compositions useful in the identification of α7 nAChR agonists, antagonists and allosteric modulators.

Ion channels are hydrophilic pores across the cellular membrane that open in response to stimulation to allow specific inorganic ions of appropriate size and charge to pass across the membrane. Depending on the nature of the ligand, ion channels expressed in the plasma membrane are broadly classified as voltage-gated ion channels (VGIC) or ligand-gated ion channels (LGIC) where the ligand usually is considered to be an extracellular messenger such as a neurotransmitter (Gopalakrishnan and Briggs, 2006). Specific residues in ion channel proteins also determine the specificity for the inorganic ion transported including sodium, potassium, calcium, and chloride ions.

Ligand-gated ion channels are essential in mediating communication between cells. These channels convert a chemical signal (often a neurotransmitter, as for example, acetylcholine) released by one cell into an electrical signal that propagates along a target cell membrane through specific ion influx. A variety of neurotransmitters and neurotransmitter receptors exist in the central and peripheral nervous systems. Numerous families of ligand-gated receptors have been identified and categorized by their specific ligands and on the basis of sequence identity. These include receptors specific for acetylcholine, glutamate, glycine, GABA A, and 5-HT.

nAChRs receptors, members of the cys-loop superfamily of LGIC, are widely characterized transmembrane proteins involved in the physiological responses to the neurotransmitter ACh and are distributed throughout both the central nervous system (CNS) and the peripheral nervous system (PNS). The nicotinic acetylcholine receptors (nAChRs) are multiunit proteins of neuromuscular and neuronal origins and mediate synaptic transmission between nerve and muscle and between neurons upon interaction with the neurotransmitter acetylcholine (ACh). Organizationally, nAChRs are homopentamers or heteropentamers composed of nine alpha and four beta subunits that co-assemble to form multiple subtypes of receptors that have a distinctive pharmacology. ACh is the endogenous ligand (agonist), while nicotine is a prototypical agonist that non-selectively activates all nAChRs. Functional nAChRs are widely expressed in the central nervous system and in the ganglia of the autonomic nervous system. nAChRs are involved in a range of synaptic and extra synaptic functions. In the peripheral nervous system, nAChRs mediate ganglionic neurotransmission whereas in the CNS, nicotinic cholinergic innervation mediates fast synaptic transmission and regulates processes such as transmitter release, synaptic plasticity and neuronal network integration by providing modulatory input to a range of other neurotransmitter systems. Thus, nAChR subtypes are implicated in a range of physiological and pathophysiological functions related to cognitive functions, learning and memory, reward, motor control, arousal and analgesia.

The α7 nAChR is a ligand-gated calcium channel formed by a homopentamer of α7 subunits. These receptors are expressed in several brain regions, especially localized at presynaptic and postsynaptic terminals in the hippocampus and cerebral cortex, regions critical to the synaptic plasticity underlying learning and memory. Presynaptic α7 nAChRs present on GABAergic, glutamatergic and cholinergic neurons can facilitate directly or indirectly the release of neurotransmitters such as glutamate, GABA and norepinephrine whereas postsynaptic receptors can modulate other neuronal inputs and trigger a variety of downstream signaling pathways. This facilitation of pre- and post-synaptic mechanisms by α7 nAChRs could influence synaptic plasticity, important for cognitive functions involved in attention, learning, and memory. Support for this hypothesis has emerged from pre-clinical studies with selective agonists, antagonists, and more recently, positive allosteric modulators (PAMs). Structurally diverse α7 nAChR agonists such as PNU-282987, SSR-180711A and AR-R17779 can improve performance in social recognition (Van Kampen, M. et. al., 2004), maze training (Levin, E. D. et. al., 1999; Arendash, G. W. et. al, 1995) and active avoidance (Arendash, G. W. et. al, 1995) models while α7 nAChR antagonists or antisense impair such performance (Bettany, J. H. et. al., 2001; Felix, R. and Levin, E. D., 1997; Curzon, P. et. al., 2006). Both agonists and PAMs, exemplified respectively by PNU-282987 and PNU-120596, have also been shown to reverse auditory gating deficits in animal models (Hajos, M. et. al., 2005; Hurst et al, 2005).

Although α7 nAChRs have significant Ca2+ permeability comparable to NMDA receptors, these receptors do not require membrane depolarization for activation, and the current responses are curtailed by rapid receptor desensitization processes (Quick, M. W., and Lester, R. A. J., 2002). The functional significance of α7 nAChRs is not only attributable to its electrogenic properties (i.e. modulation of neuronal excitability and neurotransmitter release) but also to its high $Ca^{2+}$-permeability and association with biochemical signaling pathways. Thus, activation of α7 nAChR can result in increased intracellular Ca2+, leading to signal transduction cascades involving the activation of a variety of protein kinases and other proteins by phosphorylation. Proteins that are phosphorylated in response to α7 nAChR activation could include extracellular signal-regulated kinase ½ (ERK1/2) (Ren, K. et. al., 2005), cAMP response element binding protein (CREB) (Roman, J. et. al., 2004) and Akt (Shaw, S. H. et. al., 2002).

The rapid receptor desensitization (within 50-100 milliseconds) of α7 nAChRs greatly limits the development of functional assays required for measurement of channel activity. A simple and high throughput assay is critical for screening for ligands that interact with the α7 nAChR with potential for the treatment of diseases where cognitive deficits remain an underlying component.

Serotonin (5-hydroxytryptamine, or 5-HT) receptors belong to at least two superfamilies: G-protein-associated receptors and ligand-gated ion channels. The majority of 5-HT receptors couple to effector molecules through G-protein coupled receptors. However, the 5-$HT_3$ receptor functions as a rapidly activating ion channel and, like other LGIC family members, incorporates a nonselective cation channel in its primary structure. 5-$HT_3$ receptors are expressed in native central and peripheral neurons where they are thought to play important roles in sensory processing and control of autonomic reflexes (Richardson, B. P., et al., 1985). 5-HT3 channels desensitize much slower than α7 nAChR.

Therefore, a chimeric receptor prepared from the human N-terminal ligand binding domain of α7 nAChR and the pore forming C-terminal domain of the human 5-HT3 would preserve the ligand selectivity for human α7 nAChR while delay the desensitization of the receptor. The delayed desensitization would make it easier to measure the channel function of α7 nAChR. Other amino acid stretches containing different segments of the α7 nAChR could be introduced to generate additional chimeras. Such chimeric receptors would be particularly useful for functional screening and identifying novel α7 nAChR agonists, modulators and antagonists.

SUMMARY OF INVENTION

In one aspect, the present invention is directed to a recombinant nucleic acid that encodes a cholinergic/serotoninergic chimeric receptor. The nucleic acid may comprise SEQ ID NO:1, SEQ ID NO:2, SEQ ID NO:3, SEQ ID NO:4, SEQ ID NO:5, SEQ ID NO:6, SEQ ID NO:7, and/or SEQ ID NO:8. The nucleic acid may encode an extracellular domain of a human neuronal nicotinic cholinergic receptor subunit and an intracellular domain of a human serotonin receptor. The human neuronal nicotinic cholinergic subunit may be an α7 subunit. The human serotonin receptor may be a 5HT$_3$ receptor. The recombinant nucleic acid may be expressed from a vector. The vector may control expression of the recombinant nucleic acid via control sequences. The recombinant nucleic acid may be operably linked to control sequences that are recognized by a host cell that is transformed with the vector.

In another aspect, the present invention is directed to a host cell that comprises the vector. The host cell may be from a cell line that is derived from a mammalian cell, a primary mammalian cell culture, and/or an oocyte. The host cell that comprises the vector may be used to produce a cholinergic/serotoninergic chimeric receptor. Accordingly, in another aspect, the present invention is directed to a method of producing a cholinergic/serotoninergic chimeric receptor. The method may comprise transforming a host cell with the vector. The vector may comprise SEQ ID NO:1, SEQ ID NO:2, SEQ ID NO:3, SEQ ID NO:4, SEQ ID NO:5, SEQ ID NO:6, SEQ ID NO:7, and/or SEQ ID NO:8, whereby SEQ ID NO:1 encodes SEQ ID NO:9; SEQ ID NO:2 encodes SEQ ID NO:10; SEQ ID NO:3 encodes SEQ ID NO:11; SEQ ID NO:4 encodes SEQ ID NO:12; SEQ ID NO:5 encodes SEQ ID NO:13; SEQ ID NO:6 encodes SEQ ID NO:14; SEQ ID NO:7 encodes SEQ ID NO:15; and SEQ ID NO:8 encodes SEQ ID NO:16.

In another aspect, the present invention is directed to a polypeptide encoded by the recombinant nucleic acid. The polypeptide may comprise SEQ ID NO:9, SEQ ID NO:10, SEQ ID NO:11, SEQ ID NO:12, SEQ ID NO:13, SEQ ID NO:14, SEQ ID NO:15, and/or SEQ ID NO:16. Each of SEQ ID NO:9-16 may be encoded by SEQ ID NOs:1-8, respectively.

In another aspect, the present invention is directed to a composition that comprises a cholinergic/serotoninergic chimeric receptor. The cholinergic/serotoninergic chimeric receptor may comprise one or more subunits of a human neuronal nicotinic receptor and one or more subunits of a human serotonin receptor. The chimeric receptor may be encoded by SEQ ID NO:1, SEQ ID NO:2, SEQ ID NO:3, SEQ ID NO:4, SEQ ID NO:5, SEQ ID NO:6, SEQ ID NO:7, and/or SEQ ID NO:8. The chimeric receptor may comprise a polypeptide having the amino acid sequence of SEQ ID NO:9, SEQ ID NO:10, SEQ ID NO:11, SEQ ID NO:12, SEQ ID NO:13, SEQ ID NO:14, SEQ ID NO:15, and/or SEQ ID NO:16.

In another aspect, the present invention is directed to a method for identifying a ligand to a cholinergic/serotoninergic chimeric receptor. The cholinergic/serotoninergic chimeric receptor may comprise the amino acid sequence of SEQ ID NO:9, SEQ ID NO:10, SEQ ID NO:11, SEQ ID NO:12, SEQ ID NO:13, SEQ ID NO:14, SEQ ID NO:15, and/or SEQ ID NO:16. The method may comprise contacting the cholinergic/serotoninergic chimeric receptor with a test compound, or a test compound and a positive allosteric modulator, and then measuring a response of the cholinergic/serotoninergic chimeric receptor to the test compound, wherein a measurable response of the cell indicates that the test compound is a ligand to the cholinergic/serotoninergic chimeric receptor. The receptor's response to the compound may be measured by a binding assay or an electrophysiological assay, for example. The compound may be a human neuronal nicotinic cholinergic α7 agonist and/or a human neuronal nicotinic cholinergic α7 antagonist. The positive allosteric modulator may be ivermectin, galantamine, bovine serum albumin, SLURP-1, a peptide derived from acetylcholinesterase (AChE), a derivative of quinuclidine, a derivative of indole, a derivative of benzopyrazole, a derivative of thiazole, a derivative of benzoisothiazole, and/or biarylurea. The positive allosteric modulator may be a type I positive allosteric modulator or a type II positive allosteric modulator. The type I positive allosteric modulator may be 5-HI, genistein, NS-1738, LY-2087101, and/or SB-206553. The type II positive allosteric modulator may be PNU-120596, TQS, and/or A-867744.

Figure 1:
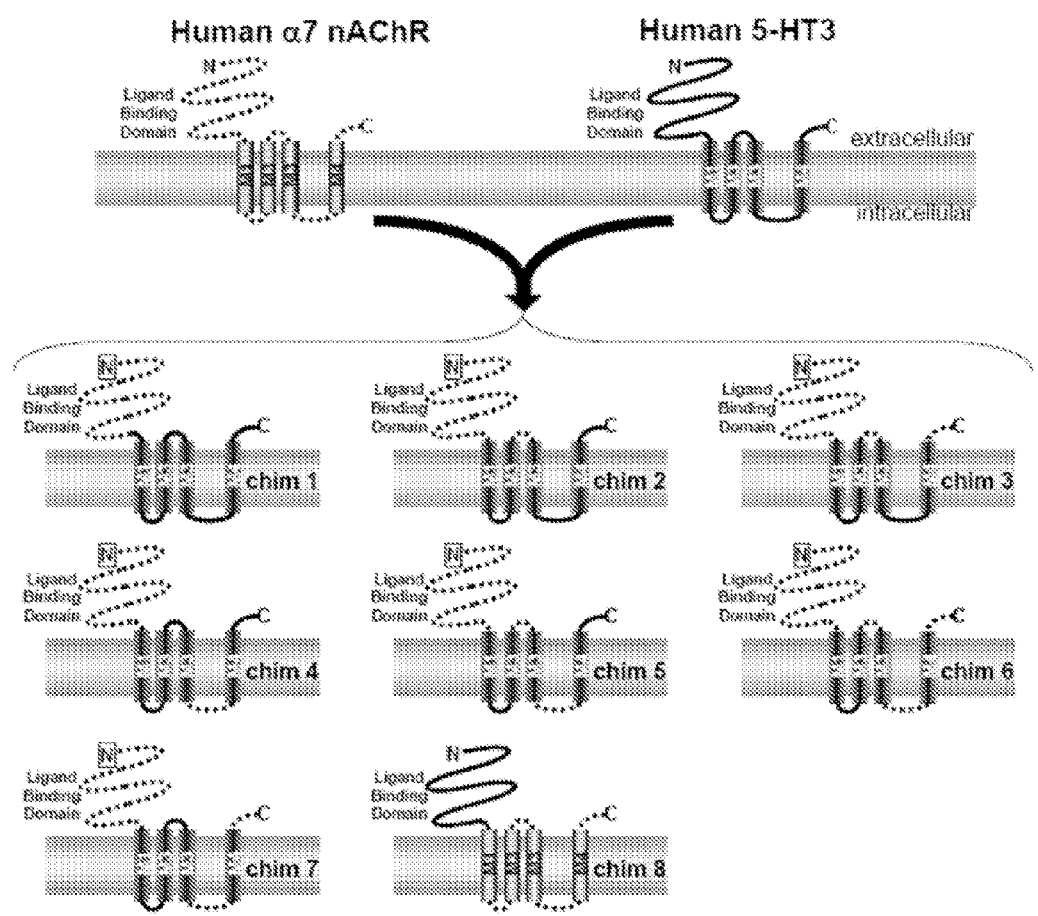
FIG. 1. Schematic representation of cholinergic (α7)/serotoninergic (5HT$_3$) Chimeras 1-8.

Table 1. Summary of α7 agonist effects in Chimera 1 and 2 expressing *Xenopus leavis* or HEK-293 cells stably expressing Chimeras studied using electrophysiology (POETs), radioligand binding, and FLIPR-FMP.

Table 2. Coefficients for the best fits of α7 wild-type, Chimera 1, and Chimera 2.

Table 3. Effects of modulators on the ACh sensitivity of the α7 wild-type receptor and the Chimeras.

Table 4. Summary of agonist potencies in Chimeras, wild-type α7 and 5-HT$_{3A}$ receptors.

Table 5. Summary of genistein and 5-HI positive allosteric modulation potencies on agonist-evoked responses in the Chimeras, wild-type α7, and 5-HT$_{3A}$ receptors.

SEQUENCE LISTING

SEQ ID NO. 1: polynucleotide sequence for human-human Chimera 1

SEQ ID NO. 2: polynucleotide sequence for human-human Chimera 2

SEQ ID NO. 3: polynucleotide sequence for human-human Chimera 3

SEQ ID NO. 4: polynucleotide sequence for human-human Chimera 4

SEQ ID NO. 5: polynucleotide sequence for human-human Chimera 5

SEQ ID NO. 6: polynucleotide sequence for human-human Chimera 6

SEQ ID NO. 7: polynucleotide sequence for human-human Chimera 7

SEQ ID NO. 8: polynucleotide sequence for human-human Chimera 8

SEQ ID NO. 9: polypeptide sequence for human-human Chimera 1

SEQ ID NO. 10: polypeptide sequence for human-human Chimera 2

SEQ ID NO. 11: polypeptide sequence for human-human Chimera 3

SEQ ID NO. 12: polypeptide sequence for human-human Chimera 4

SEQ ID NO. 13: polypeptide sequence for human-human Chimera 5

SEQ ID NO. 14: polypeptide sequence for human-human Chimera 6

SEQ ID NO. 15: polypeptide sequence for human-human Chimera 7

SEQ ID NO. 16: polypeptide sequence for human-human Chimera 8

DETAILED DESCRIPTION OF THE INVENTION

The present invention discloses fully human α7 nAChR-5HT3 chimeric receptors and an easy way to measure the channel function by delaying the desensitization, which in turn provides for a more efficient high throughput assay. Incorporation of additional amino acid stretches such as the M2-M3 segment of the α7 nAChR confers advantageous screening opportunities, particularly for allosteric modulators.

The principal embodiment of the present invention is a recombinant nucleic acid encoding a fully human amino acid sequence of a cholinergic/serotoninergic chimeric receptor. Another embodiment of said recombinant nucleic acid comprises an amino acid sequence of the fully human cholinergic/serotoninergic chimeric receptor comprising an amino acid extracellular domain with the sequence of a human neuronal nicotinic cholinergic subunit receptor, and an amino acid intracellular domain with the sequence of a human serotonin receptor. In another embodiment of the present invention the fully human cholinergic/serotoninergic chimeric receptor amino acid sequence comprises an amino acid extracellular domain with the sequence of a human neuronal nicotinic cholinergic subunit receptor, an amino acid intracellular domain with the sequence of a human serotonin receptor, and a four-transmembrane domain with an amino acid sequence of a human serotonin receptor.

Another embodiment of the present invention comprises the encoded fully human cholinergic/serotoninergic chimeric receptor amino acid sequence, in which the human neuronal nicotinic cholinergic subunit is an α7 subunit and the human serotonin receptor is a $5HT_3$ receptor.

Another embodiment of the present invention comprises the fully human cholinergic/serotoninergic chimeric receptor amino acid sequence, in which part of the sequence of the transmembrane domain is from a human neuronal nicotinic cholinergic subunit receptor, in which the N-terminal extracellular domain is from human serotonin receptor is a $5HT_3$ receptor, and in which the transmembrane domain is from a human neuronal nicotinic cholinergic subunit receptor.

It is intended that the nucleic acid sequence of the present invention can be selected from the group consisting of SEQ.ID.NO:1, SEQ.ID.NO:2, SEQ.ID.NO:3, SEQ.ID.NO:4, SEQ.ID.NO:5, SEQ.ID.NO:6, SEQ.ID.NO:7, and SEQ.ID.NO:8. It is also intended that the amino acid sequence encoded by any of said nucleic acid sequences is selected from the group consisting of SEQ.ID.NO:9, SEQ.ID.NO:10, SEQ.ID.NO:11, SEQ.ID.NO:12, SEQ.ID.NO:13, SEQ.ID.NO:14, SEQ.ID.NO:15, and SEQ.ID.NO:16.

Another embodiment of the present invention comprises a vector containing any of the recombinant nucleic acid sequences of the present invention. It is intended that the vector is operable linked to control sequences recognized by a host cell transformed with the vector.

Another embodiment of the present invention comprises a host cell comprising the vector of the present invention; it is intended that the host cell is a cell line derived from mammalian cells, primary mammalian cell cultures, or oocytes.

Another embodiment of the present invention comprises a fully human cholinergic/serotoninergic chimeric receptor encoded by the recombinant nucleic acid sequence of the present invention. It is intended that the present invention also includes a method of manufacturing the chimeric receptor of the invention, comprising a cholinergic/serotoninergic chimeric receptor with one or more regions of a human neuronal nicotinic receptor subunit and a human serotonin receptor with the vector of the invention.

Another embodiment of the present invention includes a composition comprising a cholinergic/serotoninergic chimeric receptor comprising one or more regions of a human neuronal nicotinic receptor subunit and a human serotonin receptor, preferably wherein the composition comprises any of the amino acid sequences described in the present invention.

Another embodiment includes a method of screening for compounds that bind to a region of the fully human cholinergic/serotoninergic chimeric receptor of the present invention. Said region is selected from the N-terminal domain, C-terminal domain and the extracellular loop between TM2-TM3, to modulate the activity of a neuronal nicotinic receptor. The screening method of the present invention is selected from binding or activity-based assays. Said assays can be used to determining whether the test compound binds or modulates the chimeric receptor of the present invention, wherein the binding or modulation is indicative that the test compound binds or modulates the neuronal nicotinic receptor.

Another embodiment of the present invention comprises a method of screening for a compound that binds or modulates the activity of a neuronal nicotinic receptor, comprising introducing a host cell expressing the chimeric receptor of the present invention into an acceptable medium, and monitoring an effect in said host cell indicative of binding or modulation of the test compound with the chimeric receptor, wherein the binding or modulation is indicative that the test compound binds or modulates the neuronal nicotinic receptor.

Another embodiment of the present invention is a kit comprising a host cell transformed or transfected with an expression vector comprising a nucleic acid sequence encoding a chimeric receptor of the present invention.

It is intended that any of the embodiments described herein can be modified in various obvious respects by the skilled in the art, and that all of the obvious modifications are included in the present invention.

A chimeric receptor prepared from the human N-terminal ligand binding domain of α7 nAChR and the pore forming C-terminal domain of the human 5-HT3 would preserve the ligand selectivity for human α7 nAChR while delaying the desensitization of the receptor. The delayed desensitization would make it easier to measure the channel function of α7 nAChR. The chimeras of the present invention that contain the N-terminal fragment along with the extracellular TMII-III loop corresponding to the α7 nAChR sequence are particularly useful for functional screening and identifying novel α7 nAChR ligands, i.e. agonists, modulators and antagonists. In addition, the human-human chimeric receptors described in the present application would be expected to better preserve the nature of human α7 nAChR as compared to human-rat chimera (Hurst et al, 2005).

The α7 nAChR-5-HT3 chimeric receptors of the present invention are also useful for α7 nAChR ligand binding assays. Ligand binding can be measured using either whole cells or membrane preparations. Whole cell assays are usually low throughput, while the assays using isolated membranes from animal brains typically require extensive manipulation and washing to obtain a favorable signal to noise ratio. A binding assay using cell membranes from HEK-293 cells stably transfected with α7 nAChR-$5HT_3$ chimeric receptors of the present invention that show similar binding properties to that of wild type α7 nAChR, would be extremely useful for high throughput drug screening.

Positive allosteric modulators (PAMs) have, in general, been shown not to affect α7 nAChR channel function by themselves, but can selectively enhance the effect of α7 nAChR agonists. Two types of PAMs have been described: PAM I that enhances amplitude of inward currents only (Zwart R. et. al., 2002) and PAM II that delays desensitization of the receptor and enhancing amplitude of inward currents (Hurst et al, 2005, Grønlien et al, 2007). PAM II type has been shown to enhance the acetylcholine-evoked inward currents in hippocampal interneurons on brain slice and improved the auditory gating deficit when systemically administrated to rats, suggesting that PAM II may be used as a new class of molecule that enhances α7 nAChR function and thus has the potential to treat psychiatric and neurological disorders. The binding site of PAMI/II on α7 nAChR and mechanism of their action remain unclear. These fundamental questions could be answered by using α7 nAChR-5HT3 chimeric receptors with various replacements of domains of 5-HT3 with those of α7 nAChR. More importantly, the α7 nAChR-5HT3 chimeric receptors can also be used to screen for both novel α7 agonists and positive allosteric modulators.

(I) DEFINITIONS

The following is a list of some of the definitions used in the present disclosure. These definitions are to be understood in light of the entire disclosure provided herein.

By "ligand" as used herein has its general meaning in the art, and refers to a natural or synthetic compound that has the capability to bind to a receptor and mediate, prevent or modify a biological effect.

By "agonist" as used herein has its general meaning in the art, and refers to a compound natural or not which has the capability to activate a receptor.

By "antagonist" as used herein has its general meaning in the art, and refers to a compound natural or not which has the capability to inhibit the activation of a receptor.

By "positive allosteric modulator" as used herein has its general meaning in the art, and refers to a compound natural or not which has the capability to enhance the effects of an agonist, endogenous or exogenously applied, and can interaction with sites on the receptor that are topographically distinct from the site for agonists (orthosteric sites).

By "selective", a compound that is selective is a compound able to activate or inhibit the activation of a specific receptor and not any other receptor. As used herein, selective or selectivity is used in reference to the nAChR.

By "desensitization" as used herein has its general meaning in the art, and refers to a process in vitro or in vivo in which persistent exposure of receptors to an ligand results in the eventual loss or diminution of receptor-activated responses.

(II) CHIMERIC RECEPTORS

As indicated above, the present invention provides chimeric receptors that include human N-terminal ligand binding domain of α7 nAChR and the pore forming C-terminal domain of the human 5-HT3. Transmembrane regions, intracellular and extracellular loops, are also varied to obtain the chimeras of the present invention. Schematic representation of cholinergic (α7)/serotoninergic (5HT3) Chimeras 1-8, native α7 and 5HT3 constructs, are shown in FIG. 1.

Chimera 1:

Chimera 1 has the N-terminal ligand-binding domain of α7 nAChR and the C-terminal transmembrane/pore forming region of 5-HT3. Using PCR, coding sequences were amplified with overlapping ends for the N-terminal 224 amino acids of human α7 nicotinic receptor (α7 nAChR, protein AAA83561) and the C-terminal 242 amino acids of human 5-hydroxytryptamine type-3 (5-HT3) serotonin receptor (protein AAP35868). Recombinant PCR using these two overlapping fragments yielded the open reading frame of Chimera 1. Primers used to generate the α7 nAChR portion of this chimera were (5' to 3') GCCGCCATGCGCTGCTCGC-CGGGAGGCGTCT (A7F-forward) (SEQ ID NO:17) and AGGCTGACCACATAGAAGAGTGGC-CTACGTCGGATGACCACTGTGAAGGTGACA TCG (Chi1R-reverse) (SEQ ID NO:18). Primers used to generate the 5-HT3 portion of this Chimera were (5' to 3') GTCAAGCGTACTGCCAGATGGACCAGA (5HT3R-reverse) (SEQ ID NO:19) and CGATGTCACCTTCACAGTG-GTCATCCGACGTAGGCCACTCTTCTAT-GTGGTCAGCC T (Chi1F-forward) (SEQ ID NO:20). The primers listed in these methods were manufactured and HPLC purified by Sigma Genosys. PCR was performed in a Stratagene Robocycler using 10 ng each template, 0.4 µM each primer with Invitrogen Platinum® Taq DNA Polymerase High Fidelity following Invitrogen's protocol. Recombinant PCR used 1 µl of amplicon directly from each of the two reactions along with 0.4 µM each of primers A7F and 5HT3R. All else are equal to the primary PCR. The recombinant PCR product was cloned into the expression vector pcDNA3.1 using Invitrogen's pcDNA3.1 TOPO TA cloning kit and transformed into DH5 alpha Max Efficiency Chemically Competent Bacteria from Invitrogen following the protocol. Clones were selected on plates containing LB agar medium and 100 µg/ml ampicillin. The sequence of the inserted DNA was verified.

Chimera 2:

Chimera 2 has the same amino acid composition as Chimera 1 except that 10 amino acids between transmembrane spanning (TM) region 2 and TM3 have been changed to be amino acids 280-289 of α7 nAChR (AEIMPATSDS) (SEQ ID NO:21) instead of amino acids 298-307 of 5-HT3 (SDTL-PATAIG) (SEQ ID NO:22). This was accomplished through PCR amplifying two fragments that flank the region of interest, overlap each other with codons for the desired α7 nAChR sequence, and extend to unique restriction enzyme sites for EcoRI and Bsu36I that flank the region of interest. Recombinant PCR using these two fragments produced a single amplicon to be digested with the aforementioned restriction enzymes and cloned into analogous sites of Chimera 1. Primers used to generate the 5' portion of this amplicon were (5' to 3') CACACTAACGTGTTGGTGAATTCTT (A7.ECORIF-forward) (SEQ ID NO:23) and TCGGATGTTGCGGGCAT-GATCTCAGCAACGATGATCAGGAAGACCGAGTA (Chi2R-reverse) (SEQ ID NO:24). Primers used to generate the 3' portion of this amplicon were (5' to 3') GAAGT-TGACTGCTCCCTCAGGCAA (5HT.BSUR-reverse) (SEQ ID NO:25) and ATCATGCCCGCAACATCCGATTC-GACTCCTCTCATTGGTGTCTAC (Chi2F-forward) (SEQ ID NO:26). PCR was performed as described above except that Chimera 1 plasmid was used as template in each of the two reactions. Recombinant PCR used 1 µl of amplicon directly from each of the two reactions along with 0.4 µM each of primers A7.ECORIF and 5HT.BSUR. The product from the recombinant PCR was purified using Qiagen's Qiaquick Purification kit following the protocol. EcoRI and Bsu36I from New England Biolabs were used to digest approximately 5 µg of the purified PCR product in NEBuffer 3 for 2 hours at 37° C. This digestion product (insert) was then purified using the Qiaquick method. These same restriction enzyme conditions were used to digest 1 µg Chimera 1 plasmid. The Chimera 2 plasmid digestion product was electrophoresed in 0.8% agarose and the large band was purified from the small EcoRI-Bsu36I fragment by gel purification. The purified insert and plasmid were then ligated using NEB Quick Ligase following the protocol and transformed into DH5 alpha Max Efficiency Chemically Competent Bacteria from Invitrogen. Clones were selected on plates containing LB agar medium and 100 µg/ml ampicillin. The sequence of the inserted DNA was verified.

Chimera 3:

Chimera 3 has the same amino acid composition as Chimera 2 except that the last 3 amino acids (originally 5-HT3 amino acids 482-484, QYA) have been replaced by the 9 most C-terminal amino acids of α7 nAChR (VEAVSKDFA) (SEQ ID NO:27). This was accomplished by manufacturing the replacement sequence encoding these 9 amino acids with flanking restriction enzyme sites for NheI and ApaI and then cloning this piece into the analogous sites of Chimera 2. Primers used to manufacture the replacement sequence (5' to 3') were TATTCCACATTTACCTGCTAGCGGT-GCTGGCCTACAGCATCACCCTGGTTATGCTCTG 5 (HT .NHEIF-forward) (SEQ ID NO:28) and GGGCCCT-CACGCAAAGTCTTTGGACACGGCCTC-CACCCAGATGGACCAGAGCATAA CCAGGG TGA (A7.CTAILR-reverse) (SEQ ID NO:29). These primers anneal to one another and may be extended through PCR to manufacture the desired insert. PCR was performed as described above except that no template was added to the reaction; the primers alone acted as template. Approximately 5 µg of the product from this reaction was purified using Qiagen's Qiaquick Purification Kit following the protocol and digested with NheI and ApaI from New England Biolabs in NEBuffer 4 for 2 hours at 37° C. Chimera 2 plasmid (1 µg) was digested similarly. Agarose electrophoresis using 0.8% agarose was used to purify the manufactured insert from its cleaved ends and also to purify the Chimera 2 plasmid from the small NheI-ApaI fragment. The prepared insert was then ligated to the prepared Chimera 2 plasmid using NEB Quick Ligase following the protocol and transformed into DH5 alpha Max Efficiency Chemically Competent Bacteria from Invitrogen. Clones were selected on plates containing LB agar medium and 100 µg/ml ampicillin. The sequence of the inserted DNA was verified.

Chimera 4:

Chimera 4 has the same amino acid composition as Chimera 1 except that the loop between transmembrane-3 portion (TM3) and transmembrane-4 portion (TM4) of 5-HT-3 have been replaced with that of α7 nAChR. This was accomplished by combination of three fragments.

(1) The ligand binding domain to TM3 fragments: This fragment contains the coding sequences of the human α7 nAChR ligand binding domain starting at the unique EcoRI site upstream the α7 nAChR ligand binding domain, through 5HT-3 TM3. It was generated by PCR from Chimera 1 using the following primers (5'-3') CACATTCCACACTAACGT-GTTGGTGAA (A7-R1-5p-5') (SEQ ID NO:30) and ATGC CGTCTCCTCTCGGCCAAACTTATCACC (5HT3-M3-3p-3') (SEQ ID NO:31) that included a terminal BsmBI restriction enzyme site, underlined, and a I-base silent mutation, in bold, which eliminates an existing BsmBI site. The PCR products were purified, digested with BsmBI and EcoRI, and then again purified.

(2) TM3-TM4 fragment: This fragment contains the coding sequences of the α7 nAChR TM3-TM4 cytoplasmic loop and was generated by PCR from a cDNA clone of the human α7 nAChR receptor. Primers used to generate the "TM3-TM4" fragment were (5' to 3') were ATGC CGTCTCCGAGACCGTGATCGTGCTGCAG (A7-M3-5p-5') (SEQ ID NO:32) that included a terminal BsmBI restriction enzyme site, underlined; and CAT GCTAGCAGGTAAATGTGGAATAGCAGCTTGTCCACC ACACAGGCGG (A7-M4-3p-3') (SEQ ID NO:33) that included the 5HT3R TM4 from its beginning through its internal NheI site, underlined). The PCR product was purified, digested with BsmBI and NheI, and then purified again.

(3) TM4 to EcoRI fragment: this fragment contains the 5HT-3 TM4, followed by 5HT-3 C-terminal, through the unique EcoRI site upstream α7 nAChR ligand binding domain. It was generated by digestion of the Chimeras 1 with EcoRI and NheI, followed by treatment with calf intestinal alkaline phosphatase and purification by gel electrophoresis.

These three DNA fragments were ligated together with DNA Ligase. The ligations were then transformed into DH5 alpha Max Efficiency Chemically Competent Bacteria from Invitrogen. Clones were selected on plates containing LB agar medium and 100 µg/ml ampicillin. The sequence of the inserted DNA was verified.

Chimera 5:

Chimera 5 has the same amino acid composition as Chimera 2 except that the loop between TM3 and TM4 of 5HT-3 has been replaced with that of α7 nAChR. This was accomplished by combination of three fragments.

(1) The ligand binding domain to TM3 fragment: This fragment contains the coding sequences of the human α7 nAChR ligand binding domain starting at the unique EcoRI site upstream the α7 nAChR ligand binding domain, through 5HT-3 TM3, in which the loop between TM2 and TM3 was from α7 nAChR. It was generated by PCR from Chimera 2 using the following primers: CACATTCCACACTAACGT-GTTGGTGAA (A7-R1-5p-5') (SEQ ID NO:30) and ATGC CGTCTCCTCTCGGCCAAACTTATCACC (5HT3-M3-3p-3') (SEQ ID NO:31) that included a terminal BsmBI restriction enzyme site, underlined, and a 1-base silent mutation, in bold, which eliminates an existing BsmBI site. The PCR products were purified, digested with BsmBI and EcoRI, and then again purified.

(2) TM3-TM4 fragment: This fragment contains the coding sequences of the α7 nAChR TM3-TM4 cytoplasmic loop and was generated by PCR from a cDNA clone of the human α7 nAChR receptor. Primers used to generate the "TM3-TM4" fragment were (5' to 3') ATGC CGTCTCCGAGACCGTGATCGTGCTGCAG (A7-M3-5p-5') (SEQ ID NO:32) that included a terminal BsmBI restriction enzyme site (underlined) and CAT GCTAGCAGGTAAATGTGGAATAGCAGCTTGTCCACC ACACAGGCGG (A7-M4-3p-3') (SEQ ID NO:33) that included the 5HT3R TM4 from its beginning through its internal NheI site (underlined). The PCR product was purified, digested with BsmBI and NheI, and then purified again.

(3) TM4 to EcoRI fragment: this fragment contains the 5HT-3 TM4, followed by 5HT-3 C-terminal, through the unique EcoRI site upstream α7 nAChR ligand binding domain. It was generated by digestion of the Chimeras 2 with EcoRI and NheI, followed by treatment with calf intestinal alkaline phosphatase and purification by gel electrophoresis.

These three DNA fragments were ligated together with DNA Ligase. The ligations were then transformed into DH5 alpha Max Efficiency Chemically Competent Bacteria from Invitrogen. Clones were selected on plates containing LB agar medium and 100 μg/ml ampicillin. The sequence of the inserted DNA was verified.

Chimera 6:

Chimera 6 has the same amino acid composition as Chimera 3 except that the loop between TM3 and TM4 of 5HT-3 has been replaced with that of α7 nAChR. This was accomplished by combination of three fragments.

(1) The ligand binding domain to TM3 fragment: This fragment contains the coding sequences of the human α7 nAChR ligand binding domain starting at the unique EcoRI site upstream the α7 nAChR ligand binding domain, through 5HT-3 TM3, in which the loop between TM2 and TM3 was from α7 nAChR. It was generated by PCR from Chimera 3 using the following primers: CACATTCCACACTAACGT-GTTGGTGAA (A7-R1-5p-5') (SEQ ID NO:30) and ATGC CGTCTCCTCTCGGCCAAACTTATCACC (5HT3-M3-3p-3') (SEQ ID NO:31) that included a terminal BsmBI restriction enzyme site, underlined, and a 1-base silent mutation, in bold, which eliminates an existing BsmBI site. The PCR products were purified, digested with BsmBI and EcoRI, and then again purified.

(2) TM3-TM4 fragment: This fragment contains the coding sequences of the α7 nAChR TM3-TM4 cytoplasmic loop and was generated by PCR from a cDNA clone of the human α7 nAChR receptor. Primers used to generate the "TM3-TM4" fragment were (5' to 3') ATGC CGTCTCCGAGACCGTGATCGTGCTGCAG (A7-M3-5p-5') (SEQ ID NO:32) that included a terminal BsmBI restriction enzyme site (underlined) and CAT GCTAGCAGGTAAATGTGGAATAGCAGCTTGTCCACC ACACAGGCGG (A7-M4-3p-3') (SEQ ID NO:33) that included the 5HT3R TM4 from its beginning through its internal NheI site (underlined). The PCR product was purified, digested with BsmBI and NheI, and then purified again.

(3) TM4 to EcoRI fragment: this fragment contains the 5HT-3 TM4, followed by α7 nAChR C-terminal, through the unique EcoRI site upstream α7 nAChR ligand binding domain. It was generated by digestion of the Chimeras 3 with EcoRI and NheI, followed by treatment with calf intestinal alkaline phosphatase and purification by gel electrophoresis.

These three DNA fragments were ligated together with DNA Ligase. The ligations were then transformed into DH5 alpha Max Efficiency Chemically Competent Bacteria from Invitrogen. Clones were selected on plates containing LB agar medium and 100 μg/ml ampicillin. The sequence of the inserted DNA was verified.

Chimera 7:

Chimera 7 has the same amino acid composition as Chimera 4 except that the 5HT-3 C-terminal has been replaced with the α7 nAChR C-terminal. This was accomplished by combination of three fragments.

(1) The ligand binding domain to TM3 fragment: This fragment contains the coding sequences of the human α7 nAChR ligand binding domain starting at the unique EcoRI site upstream the α7 nAChR ligand binding domain, through 5HT-3 TM3. It was generated by PCR from Chimera 1 using the following primers: CACATTCCACACTAACGTGTTG-GTGAA (A7-R1-5p-5') (SEQ ID NO:30) and ATGC CGTCTCCTCTCGGCCAAACTTATCACC (5HT3-M3-3p-3') (SEQ ID NO:31) that included a terminal BsmBI restriction enzyme site (underlined) and a 1-base silent mutation (in bold) which eliminates an existing BsmBI site. The PCR products were purified, digested with BsmBI and EcoRI, and then again purified.

(2) TM3-TM4 fragment: This fragment contains the coding sequences of the α7 nAChR TM3-TM4 cytoplasmic loop and was generated by PCR from a cDNA clone of the human α7 nAChR receptor. Primers used to generate the "TM3-TM4" fragment were (5' to 3') ATGC CGTCTCCGAGACCGTGATCGTGCTGCAG (A7-M3-5p-5') (SEQ ID NO:32) that included a terminal BsmBI restriction enzyme site (underlined) and CAT GCTAGCAGGTAAATGTGGAATAGCAGCTTGTCCACC ACACAGGCGG (A7-M4-3p-3') (SEQ ID NO:33) that included the 5HT3R TM4 from its beginning through its internal NheI site (underlined). The PCR product was purified, digested with BsmBI and NheI, and then purified again.

(3) TM4 to EcoRI fragment: this fragment contains the 5HT-3 TM4, followed by α7 nAChR C-terminal, through the unique EcoRI site upstream α7 nAChR ligand binding domain. It was generated by digestion of the Chimeras 3 with EcoRI and NheI, followed by treatment with calf intestinal alkaline phosphatase and purification by gel electrophoresis.

These three DNA fragments were ligated together with DNA Ligase. The ligations were then transformed into DH5 alpha Max Efficiency Chemically Competent Bacteria from Invitrogen. Clones were selected on plates containing LB agar medium and 100 pg/ml ampicillin. The sequence of the inserted DNA was verified.

Chimera 8 (Reverse Chimera):

Chimera 8 is the reverse form of Chimera 1. Chimera 8 has the ligand-binding domain of 5-HT3 and the transmembrane/pore-forming region of α7 nAChR. Using PCR, coding sequence for the 5HT-3 N-terminal and the α7 nAChR C-terminal were amplified with overlapping ends. Recombinant PCR using these two overlapping fragments yielded the open reading frame of Chimera 8. Primers used to generate the 5-HT3 portion of this Chimera were (5' to 3') GCCGCCAT-GCTTGGAAAGCTCGCTATGCT (5HT3F-forward) (SEQ ID NO:34) and AGCGTCCTGCGGCGCATGGTCACATA-GAACTTCATTTCTG (RChi1R-reverse) (SEQ ID NO:35). Primers used to generate the α7 nAChR portion of this Chimera were (5' to 3') GTTACGCAAAGTCTTTGGA-CACGGC (A7R-reverse) (SEQ ID NO:36) and CAGAAAT-GAAGTTCTATGTGACCATGCGCCGCAGGACGCT (RChi1F-forward) (SEQ ID NO:37) PCR was performed in a Stratagene Robocycler using 10 ng each template, 0.4 μM each primer with Invitrogen Platinum® Taq DNA Polymerase High Fidelity following Invitrogen's protocol. Recombinant PCR used 1 μl of amplicon directly from each of the two reactions along with 0.4 μM each of primers 5HT3F and A7R and was carried out identically to that for the generation of the Chimera 1 recombinant product. The recombinant PCR product was cloned into the expression vector pcDNA3.1 using Invitrogen's pcDNA3.1 TOPO TA cloning kit and transformed into DH5 alpha Max Efficiency Chemically Competent Bacteria from Invitrogen following the protocol. Clones were selected on plates containing LB agar medium and 100 μg/ml ampicillin. The sequence of the inserted DNA of was verified.

(III) POSITIVE ALLOSTERIC MODULATORS

Figure 9:
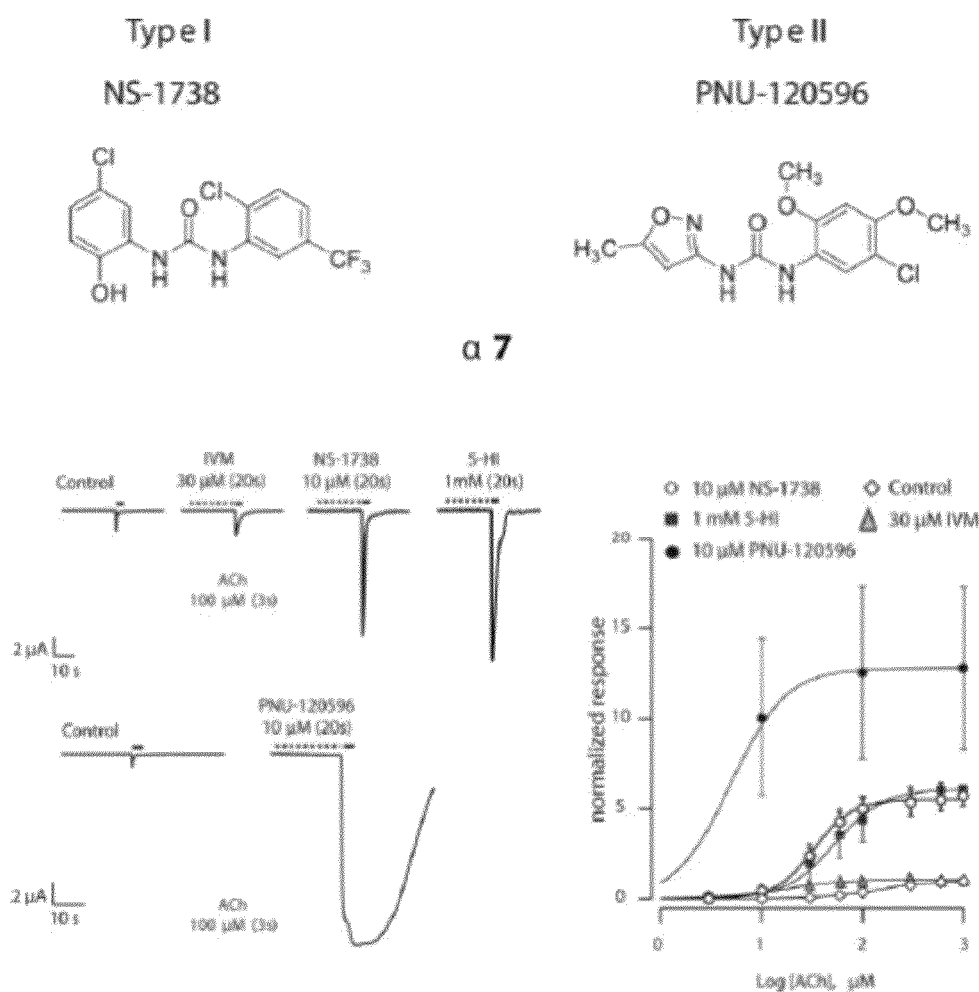
FIG. 9. Structures and effects of type I and II positive allosteric modulators of α7 nAChRs. Bottom left, effects of NS-1738 and PNU-120596 in an oocyte expressing the α7 nAChR. Currents evoked by brief ACh test pulse (100 μM, 3 s) were recorded at regular intervals. Exposure to IVM, NS-1738, and 5HI caused a substantial increase in the amplitude of the subsequent ACh-evoked current without major modification of the response time course. Full recovery was obtained after wash (not shown). By comparison, exposure to PNU-120596 in the same cell caused both an increase in the amplitude of the ACh-evoked current and a marked slowing of the receptor desensitization. The cell was maintained in voltage clamp at −100 mV. Right, effects of the positive allosteric modulators on the concentration-activation curves. Error bars indicate the S.E.M. for α7 (n=5), α7 IVM (n=5), α7 5-HI (n=3), α7 NS-1738 (n=5), and α7 PNU-120596 (n=3). Curves through data points are the best fit obtained with the empirical Hill equation. Corresponding coefficients are presented in Table 2.

A diversity of α7 positive allosteric modulators have been identified and are known. Type I modulators including 5-hydroxyindole (5-HI), genistein, NS-1738, LY-2087101, and SB-206553 predominantly increase the peak current response with little effect on current decay rate, and type II modulators exemplified by PNU-120596, TQS, and A-867744 that, in addition to potentiating the peak current amplitude, also strongly affect the current decay kinetics (desensitization). Other PAMs include ivermectin, galantamine, bovine serum albumin, and SLURP-1, and a peptide derived from acetylcholinesterase (AChE). Still other PAMs include derivatives of quinuclidine, indole, benzopyrazole, thiazole, and benzoisothiazoles (see for example, Hurst, R. S., et al., J. Neurosci., 2005, 25: 4396-4405; Broad, L. M., et al., Drugs of the Future, 2007, 32(2):161-170; U.S. Pat. No. 7,160,876). NS-1738 and PNU-120596 belong to the biarylurea class of PAMs where there may be differences in the substitution patterns on the aryl rings (for example, isoxazole in case of PNU-120596 versus substituted phenyl in case of NS-1738; FIG. 9); accordingly, there may be differences in the log P values (~2.8 for PNU-120596 versus ~4.8 for NS-1738, respectively). These differences may influence allosteric modulatory interactions of these two compounds at α7 nAChRs. The emergence of structurally distinct PAMs of different in vitro profiles offers valuable tools with which to further define the physiology and pharmacology of α7 nAChR transmission.

The modulative effects of dissimilar PAMs may be different depending on the presence of an α7 encoded extracellular M2-M3 loop on the nicotinic receptor. In Chimera 2, genestin and 5-HI function as positive allosteric modulators, similarly to their effects on the wild-type α7 nicotinic receptor. See below Examples. In Chimera 1, 5-HI but not genestin is effective a PAM. At concentrations higher than required for their allosteric modulation, 5-HI and genestin evoke non-decaying current activation in Chimera 2, but not Chimera 1. Still further, agonists are more potent and display slower current decay rate at Chimera 2 than Chimera 1 or α7 receptors. The M2-M3 loop is thereby an important for channel gating in addition to the obligatory role in the modulation for genestein and 5-HI, for example.

(IV) TECHNIQUES (1) Electrophysiology

Xenopus laevis oocytes were prepared and injected as previously described {Eisele, 1993 #2; Krause, 1998 #4}. Briefly, ovaries were harvested from female Xenopus. Isolation of the oocytes was obtained by enzymatic dissociation using collagenase type I in a medium deprived of calcium and by gentle mechanical agitation for approximately 3 hours. Oocytes stage 5-6 were manually selected on the next day and injected into the nucleus with 2 ng plasmid containing the cDNA of interest. Oocytes were then placed in a 96 well microtiter plate in Barth solution and used for electrophysiological investigation two to five days later. All recordings were performed at 18° C. and cells were superfused with OR2 medium containing in mM:NaCl 82.5, KCI 2.5, HEPES 5, $CaCl_2 \cdot 2H_2O$ 2.5, $MgCl_2 \cdot 6H_2O$ 1, pH 7.4, and 0.5 µM atropine was added to prevent possible activation of endogenous muscarinic receptors. Unless indicated cells were held at −100 mV using a two electrode voltage clamp apparatus connected to a Geneclamp amplifier (Molecular Devices). Data were captured and analyzed using data acquisition and analysis software. Concentration-response curves were fit using the empirical Hill equation: $Y=1/1+(EC_{50}/x)^{n_H}$ where: y=the fraction of remaining current, $EC_{50}$=concentration of half inhibition, $n_H$=the apparent cooperativity, x=agonist concentration. Values indicated throughout the text are given with their respective standard error of the mean (SEM). For statistical analysis we used the unpaired, two-tailed Student's T test using either excel (Microsoft) or Matlab (Mathworks Inc.).

(2) Membrane Potential Measurement

HEK-293 cells stably expressing human α7 nAChR-5HT3 chimeric receptors were grown to confluence in 162-175 $cm^2$ tissue culture flasks in Dulbecco's Modified Eagle Media (DMEM) supplemented with 10% fetal bovine serum (FBS) and 0.6 mg/ml G-418. The cells were then dissociated using cell dissociation buffer and resuspended in the growth medium. Cells were plated at 100 ul of cell suspension (~60,000-80,000 cells/well) into 96-well black plates (poly-D-lysine precoated) with clear bottom and maintained for 24-48 hrs in a tissue culture incubator at 37° C. under an atmosphere of 5% $CO_2$: 95% air. On the day of testing, responses were measured using Fast Membrane Potential (FMP) dye (Molecular Devices) according to manufacturer's instructions. Briefly, a stock solution of the dye was prepared by dissolving each vial supplied by the vendor in low $Ca^{2+}$ and low $Mg^{2+}$ Hank's balanced salt solution buffer (HBSS) containing 10 mM HEPES and 0.5 uM atropine. The low $Ca^{2+}$ and $Mg^{2+}$ HBSS buffer was obtained by adding 0.1 mM CaC12 and 0.1 mM MgC12 to $Ca^{2+}$ and $Mg^{2+}$ free HBSS. Instead of $Ca^{2+}$ and $Mg^{2+}$ free HBSS, $Ca^{2+}$ and $Mg^{2+}$ free PBS can also be used. The dye stock solution was diluted 1:10 with the same buffer before use. The growth media was removed from the cells. The cells were loaded with 100 ul of the dye per well and incubated at room temperature for up to 1 hr. Fluorescence measurements were read simultaneously from all the wells by a Fluorometic Imaging Plate Reader (FLIPR) at an excitation wavelength of 480 nm and by using an emission filter provided by Molecular Devices specifically for the fluorescence membrane potential (FMP). Depending on the purpose of experiments either a single addition or double addition protocol was used. In a single addition (agonist) protocol, the basal fluorescence was measured for 10 sec and 50 ul of compounds (3-fold higher concentration) was added, and responses measured for up to 10 min. In the double addition (modulator) protocol, basal fluorescence was measured for 10 sec then 50 ul (3-fold higher concentration) of test compounds were added in the first addition for 5-10 min followed by 50 ul of the second compound addition (4-fold higher concentration). The double addition protocol can be used to measure antagonist or positive allosteric modulator activity when the second addition utilizes submaximum concentration of an agonist. Data were normalized to maximal responses of a reference α7 nAChR agonist (100 uM acetylcholine or 1 uM NS6784) and plotted as a function of concentration In agonist experiments or to submaximum response of the reference agonist (60-120 nM NS6784).

(3) Radioligand Binding

[$^3$H]-A585539, also known as ([$^3$H]-(S,S)-2,2-dimethyl-5-(6-phenyl-pyridazin-3-yl)-5-aza-2-azonia-bicyclo[2.2.1] heptane iodide) or [$^3$H]-DPPB (U.S. patent application No. 20070072892A1), binding to α7 nAChR-5HT3 chimeric receptors was determined using cellular membranes. Adherent cells were scraped from tissue culture flasks using Dulbecco's PBS with 0.1 mM PMSF. The cells were centrifuged at 500× g for 10 min and the pellets were homogenized with a Polytron at a setting of 7 for 20 sec in 30 volumes of BSS-Tris buffer (120 mM NaCl, 5 mM KCl, 2 mM $CaCl_2$, 2 mM $MgCl_2$, and 50 mM Tris-Cl, pH 7.4, 4° C.). After centrifugation at 500× g for 10 min, the resultant supernatant was centrifuged at 40,000× g for 15 min. The membrane pellets were resuspended in BSS to result In 2-5 mg protein per aliquot. Maximal binding levels ($B_{MAX}$) and dissociation constants ($K_D$) were determined using 8-16 concentrations from 0.05 to 5 nM of [$^3$H]-A585539 (62.8 Ci/mmol; R46V, Abbott Labs). Samples were incubated in a final volume of 500 µl for 75 min at 4° C. in quadruplicate. Non-specific binding was determined in the presence of 10 µM (−)nicotine In duplicate. Bound radioactivity was collected on Millipore Multi-Screen® harvest plates FB presoaked with 0.3% PEI using a PerkinElmer cell harvester, washed with 2.5 ml ice-cold buffer, and radioactivity was determined using a PerkinElmer TopCount® microplate beta counter. $K_D$ and $B_{MAX}$ values were determined from nonlinear regression analysis of untransformed data using GraphPad Prism®. For displacement curves, seven log-dilution concentrations of test compounds containing 2-5 µg of protein, and 0.5 nM [$^3$H]-A585539 (62.8 Ci/mmol; R46V, Abbott Labs) were incubated in a final volume of 500 µl for 75 minutes at 4° C. in duplicate. Non-specific binding was determined in the presence of 10 µM methyllycaconitine. $IC_{50}$ values were determined by nonlinear regression in Microsoft® Excel or Assay Explorer. $K_i$ values were calculated from the $IC_{50}$s using the Cheng-Prusoff equation, where $K_i = IC_{50}/(1+[Ligand]/K_D)$ (V) EXAMPLES Example 1

Expression of Chimeras and Responses to α7 nAChR Agonists

Figure 2:
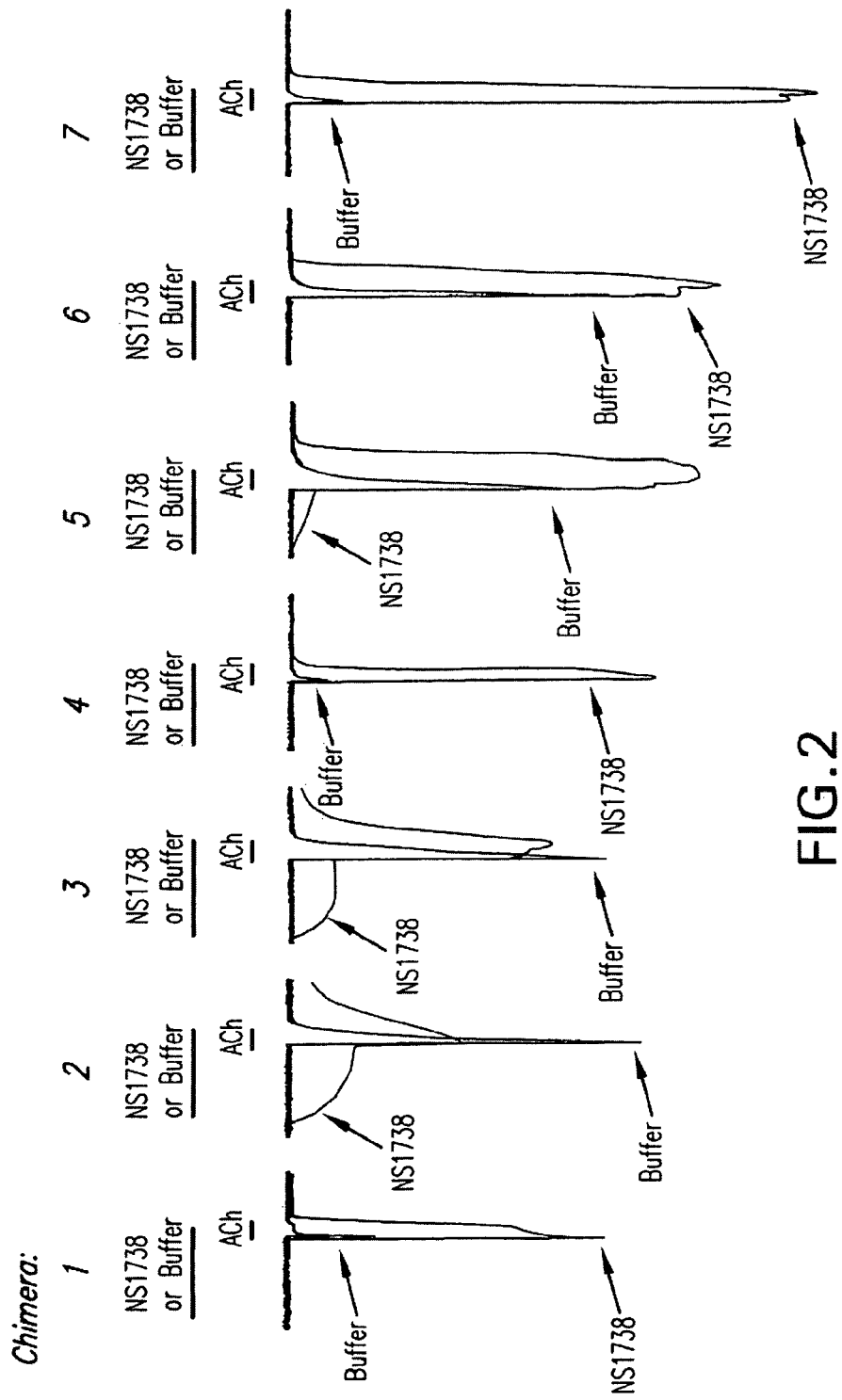
FIG. 2. Illustration of expression of cholinergic (α7)/serotoninergic (5HT$_3$) chimeras by electrophysiology (two electrode voltage clamp).

All engineered chimeras contain the α7 encoded N-terminal extracellular region, which contains the agonist binding sites. Therefore, α7 agonists, but not 5-HT3A agonists, should activate these channels. All α7-5HT3 chimeras were screened for functional expression by injecting the cDNA in *Xenopus laevis* oocytes. FIG. 2 shows all 7 chimeras expressed in *Xenopus* oocytes were activated by ACh by electrophysiology (two electrode voltage clamp). As demonstrated in the figure, ACh activated currents in all chimeras. FIG. 2 also shows that NS 1738, a positive allosteric modulator, can differentially potentiate various chimeras activated by the endogenous agonist, acetylcholine. Secondly, unlike at the wild type α7 nAChRs, NS 1738 alone generally activated current responses when the α7 encoded sequence for extracellular TM 2-3 loop was present.

Figure 3A:
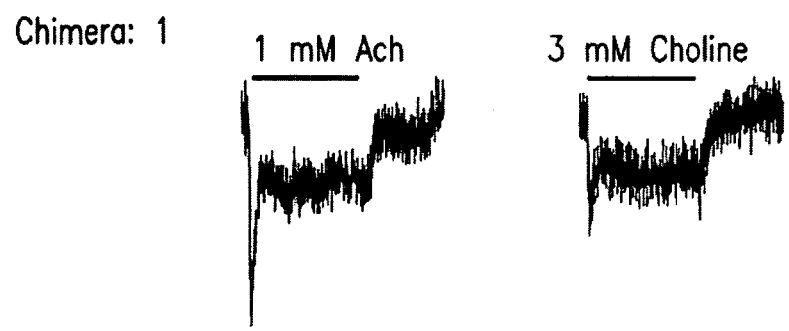
FIG. 3. HEK-293 cells stably expressing Chimera 1 and 2 express functional currents with distinct properties.
Figure 3B:
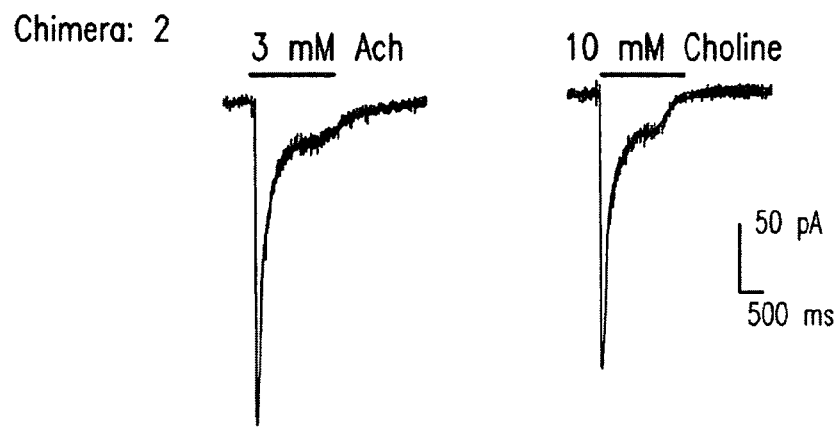

The α7 nAChR-like channel function of the chimeras was confirmed by currents evoked by ACh and choline in HEK-293 cells stably expressing Chimera 1 and 2. FIGS. 3 (a) and (b) show representative currents evoked by ACh and choline, as indicated by horizontal bars, in HEK-293-Chimera 1 and HEK-293-Chimera 2 cells, respectively. Responses were measured using the patch clamp technique and compounds were applied using rapid compound addition, holding potential was −80 mV. In general, Chimera 2 currents had higher amplitudes and showed slower decay rates than Chimera 1.

Figure 4A:
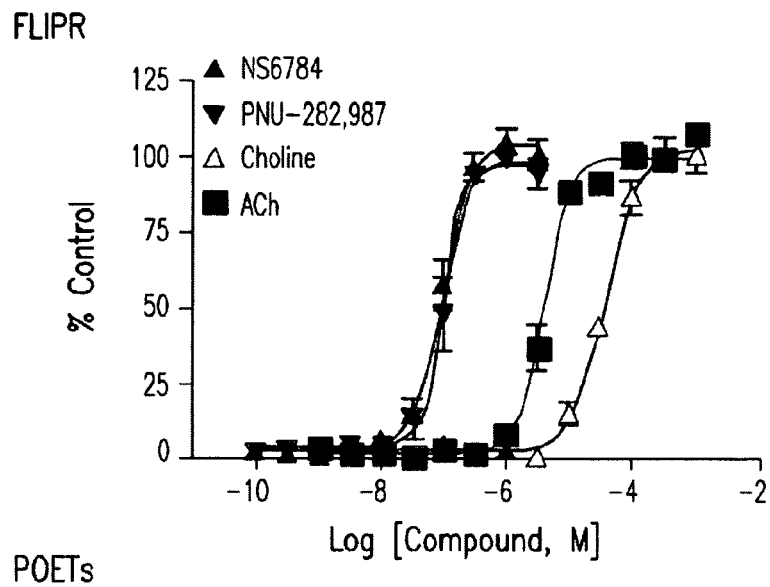
FIG. 4. Effects of α7 agonists in HEK-293 cells stably expressing Chimera 2.
Figure 4B:
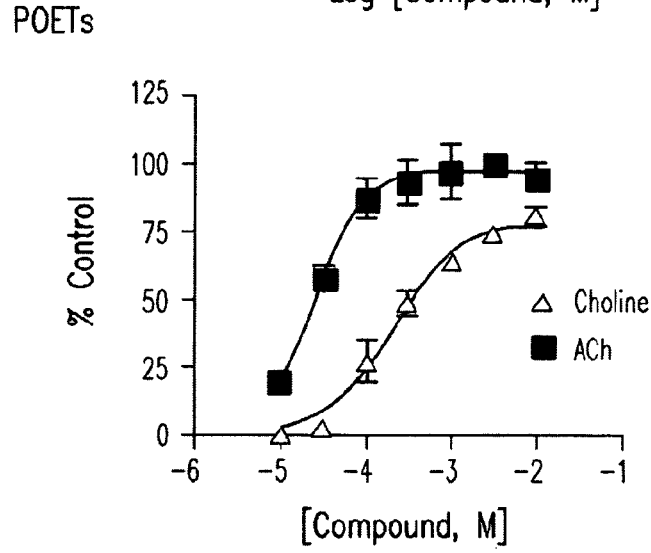
Figure 4C:
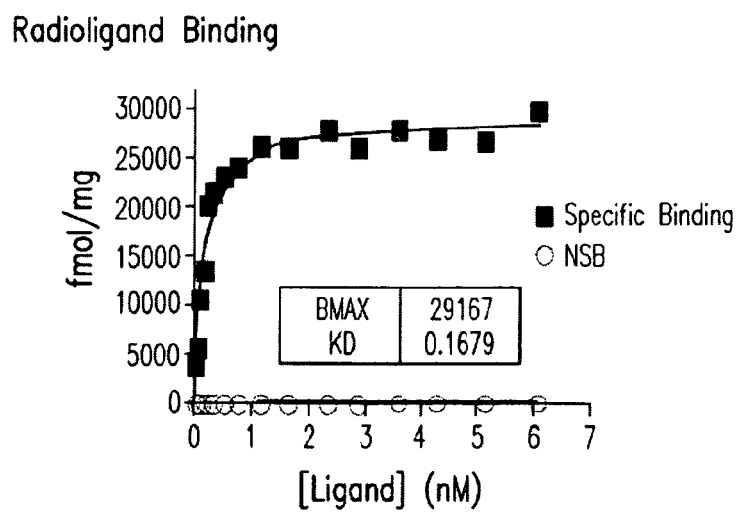

FIG. 4a shows a series of concentration-responses to four agonists measured in HEK-293-Chimera 2 cells using FMP dye in FLIPR. The rank order of potency is as follows: NS6784 (2-(1,4-diazabicyclo[3.2.2]nonan-4-yl)-5-phenyl-1,3,4-oxadiazole)NS6784≈PNU-282,987>ACh>choline. This shows that stable cell lines generated from the novel Chimeras can be used to screen for agonists, antagonists, or allosteric modulators. In Chimera 1 and 2 cells, the current and membrane potential responses could be evoked in concentration dependent manner by a7 agonists such as: ACh, choline, PNU-282,987, or NS6784. FIG. 4b shows concentration responses to ACh and choline recorded in *Xenopus lea vis* oocytes expressing Chimera 2 examined using Parallel Oocyte Electrophysiology Test Station (POETs). ACh is more potent than choline similarly to what was observed in FLIPR-FMP experiments. FIG. 4c shows specific binding of [$^3$H]-A585539 to membranes obtained from HEK-293 cells expressing Chimera-1 or Chimera 2. The effect of increasing unlabelled A-585539, a selective α7 agonist, on displacement of [$^3$H]A-585539 in homogenates prepared from HEK-293-Chimera 2 cells, was used for determination of affinity of this compound. As shown, [$^3$H]A-585539 bound to a single saturable site with high affinity $K_D$ equal to 0.17 nM. The Bmax was also high, 29167 fmol/mg protein, indicating high expression of Chimera 2 in this cell line. Binding was high, saturable, rapid and represented >95% of total binding over the concentration range, 0.05 to 5 nM, examined. The dissociation constants ($K_D$) of 0.65 and 0.17 nM were determined for Chimeras 1 and 2 respectively. The studies of electrophysiology, membrane potential measurement and radioligand binding in Chimera 1 and 2 are summarized in Table 1. The comparison of potencies in Chimera 1 and 2 cells illustrates that $EC_{50}$ values in the former were shifted to the left by 2-5-fold consistent with the observed shift in the affinity to [$^3$H]A-585539 (Table 1). These results indicate that the Chimeras, especially Chimera 1 and Chimera 2, function as α7 nAChR-selective ion channels and will be useful for screening various types of a7-nAChR-selective ligands including, agonists, antagonists, and allosteric modulators.

Example 2

Responses of Chimeras to Positive Allosteric Modulators (PAMs)

Figure 5:
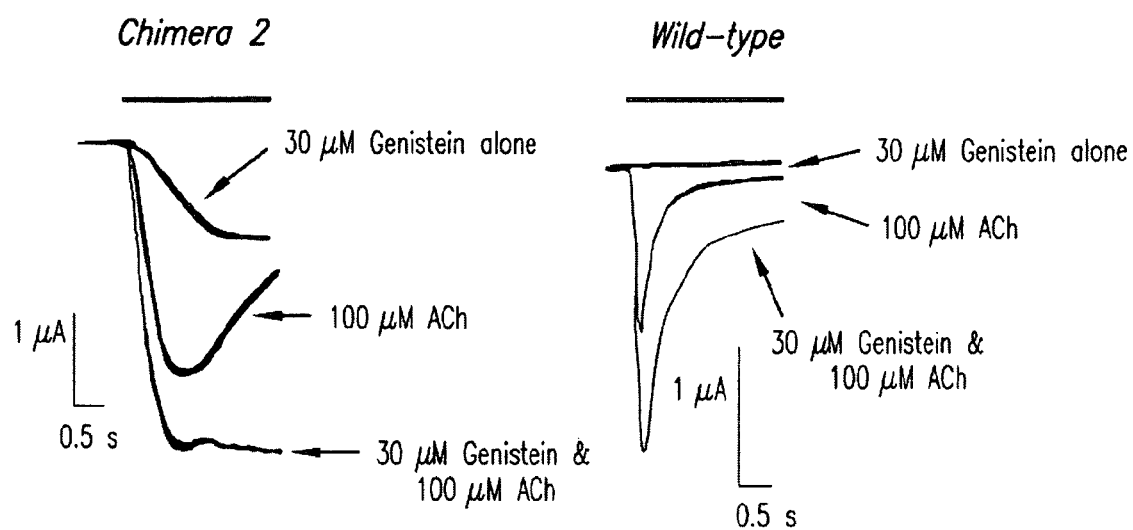
FIG. 5. Effects of genistein on ACh evoked responses in Chimera 2 expressing cells and in wild type.
Figure 6:
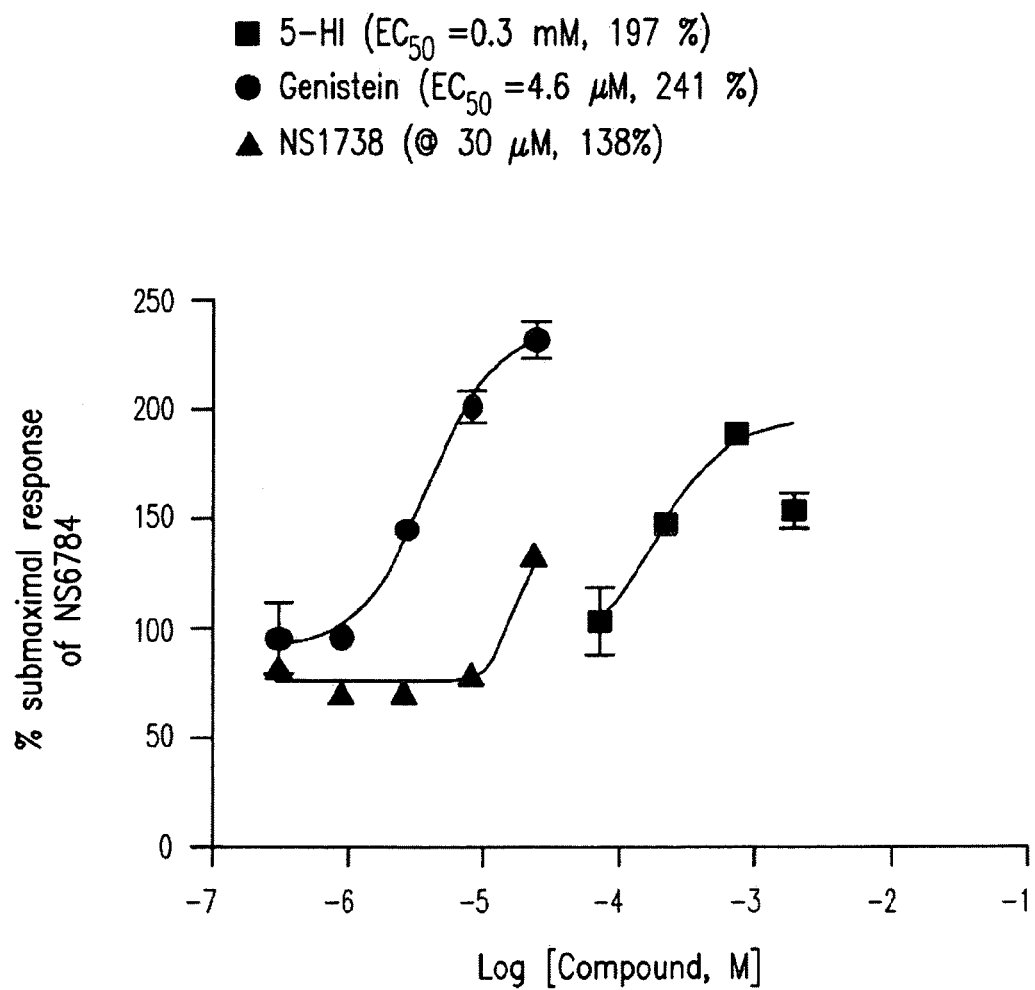
FIG. 6. Effects of modulators 5-HI, genistein and NS 1738 on Chimera 2.
Figure 7A:
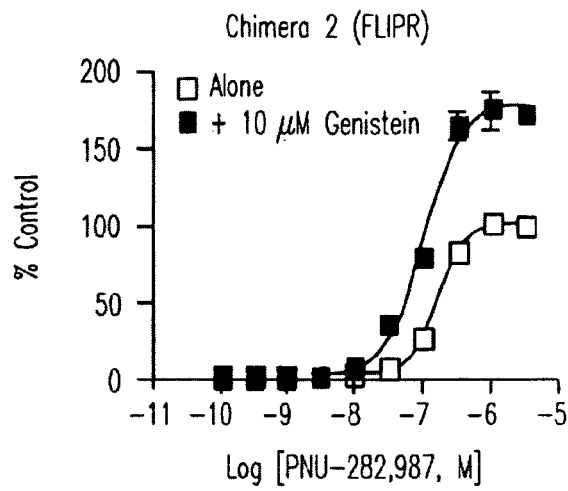
FIG. 7. Genistein potentiation of Chimera 2 and not of Chimera 1.
Figure 7B:
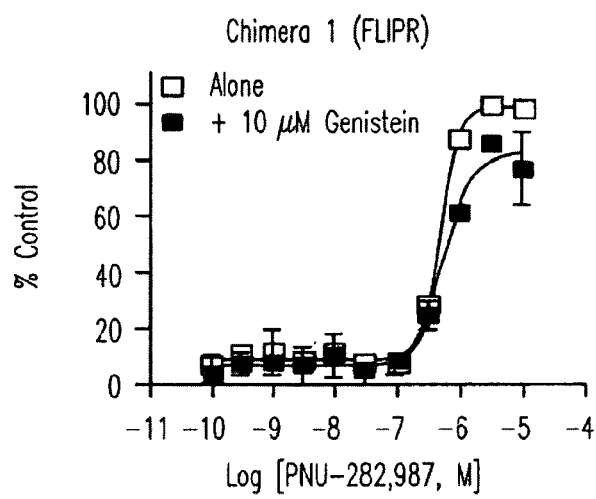

As described previously (Gronlien et al. Mol Pharmacol. 2007), the type I PAMs, genistein and 5-hydroxyindole (5-HI), potentiate α7 nAChR agonist-evoked currents by primarily increasing the current amplitude and with relatively little effect on time course of current response. These PAMs were examined to determine whether these compounds could modulate the chimeras. FIGS. 5-7, show that genistein and 5-HI had differential effects on chimeras.

In Chimera 2, 30 µM genistein not only potentiated peak amplitude of ACh current responses, but affected the time course of the response resulting in weakly or non-decaying decaying current. In addition, the time course of the response in Chimera 2 was affected differently by genistein in comparison to the wild type α7. At the wild type α7, genistein potentiates the α7 agonist evoked a7 currents by primarily increasing the current amplitude (FIG. 5).

FIG. 6 demonstrates that chimeras such as Chimera-2 (illustrated) can be utilized for screening for novel PAMs. Concentration-responses to three α7 PAMs-5-HI, NS 1738, and genistein, potentiated submaximum NS6784 evoked responses (60 nM) in HEK-293-Chimera 2 cells. The protocol employed here to determine the PAM activity is known to one skilled in the art, and involves using a submaximum concentration of a chosen α7 agonist—corresponding to $EC_{20}$ to $EC_{50}$—such as 60 nM of NS6784 in FLIPR experiments or 100 µM ACh in *Xenopus* oocyte studies, and determination of concentration-dependency of test compounds to affect these submaxmium agonist signals. As shown in FIG. 6, reference PAMs with various potencies such as genistein, 5HI and NS1738 were identified by examining membrane potential responses in Chimera-2.

Figure 7C:
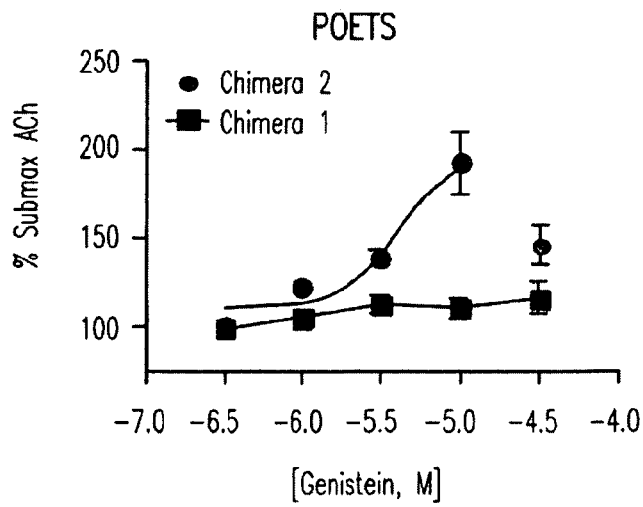

FIG. 7 shows differential potentiation by genestein in Chimeras 1 and 2. In Chimera 1—lacking the α7 encoded sequence for extracellular TMII-III loop—genistein was not effective as positive allosteric modulator. In contrast, in Chimera 2—containing the α7 encoded sequence for extracellular TMII-III loop—genestein was very effective. This differential potentiation of Chimera 2, and not Chimera 1, was confirmed electrophysiologically (see FIG. 7C), wherein genestein potentiated ACh responses in Chimera 2, but not Chimera 1. This demonstrates that the α7-encoded sequence for extracellular TMII-III loop was critical for the positive allosteric modulation by genestein. In contrast to genestein, two other PAMs, NS 1738 (Timmermann et al. J. Pharmacol. Exp. Ther. 2007) and 5-hydroxyindole, were able to potentiate both Chimeras.

Figure 8:
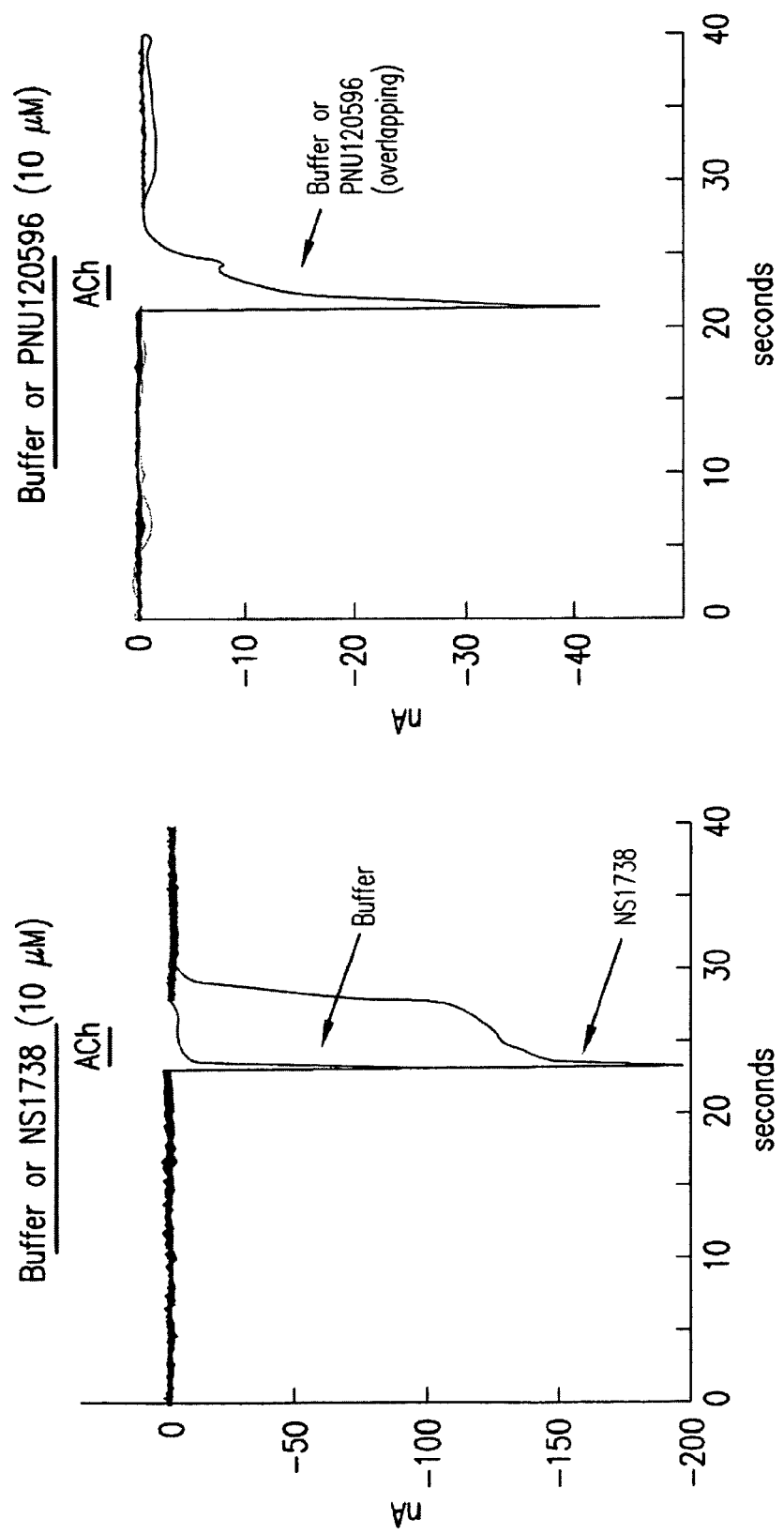
FIG. 8. Effects of PAMs NS 1738NS 1738 and PNU-120596 in Chimera 1 on responses induced by ACh.

FIG. 8 shows differential effects of NS1738 and PNU-120596 in Chimera 1 and 2; NS1738 potentiates Chimera 1, whereas PNU-120596 does not. The observation that genistein differentially potentiates Chimeras offers unique opportunities to screen compounds capable of potentiating wild-type α7. Compounds such as genistein that selectively potentiate Chimera (e.g. Chimera 2) containing the α7 encoding TMII-III loop (e.g. Chimera 2) can be identified by using this type of chimeric receptors and not when TMII-III loop is encoded by 5-HT3A. Therefore, the advantage of using these Chimeras is that PAMs of certain types or pharmacological properties can be readily identified.

Example 3

Structural Determinants Required for Positive Allosteric Modulation

Effects on the current amplitude and time course of the response were obtained after a preincubation with structurally diverse modulators: NS-1738, PNU-120596, and 5-HI. Typical α7 currents evoked by a brief ACh test pulse (100 μM, 3 s) were recorded in control, after a preincubation with NS-1738 (10 μM, 20 s) or PNU-120596 (10 μM, 20 s). Recordings of the ACh-evoked currents obtained in a series of ACh concentrations using the same experimental protocol allowed determination of the concentration dependence in the absence of and after exposure to the modulator. See FIG. 9, wherein the structures of two chemically related positive allosteric modulators of the α7 receptors are shown at the top.

The effects of NS-1738 and PNU-120596 in an oocyte expressing the α7 nAChR are shown at the bottom left of FIG. 9. Currents evoked by brief ACh test pulse (100 μM, 3 s) were recorded at regular intervals. Exposure to IVM, NS-1738, and 5HI caused a substantial increase in the amplitude of the subsequent ACh-evoked current without major modification of the response time course. Full recovery was obtained after wash (not shown). By comparison, exposure to PNU-120596 in the same cell caused both an increase in the amplitude of the ACh-evoked current and a marked slowing of the receptor desensitization. The cell was maintained in voltage clamp at −100 mV. The right side of FIG. 9 shows the effects of the positive allosteric modulators on the concentration-activation curves, wherein the error bars indicate the S.E.M. for α7 (n=5), α7 IVM (n=5), α7 5-HI (n=3), α7 NS-1738 (n=5), and α7 PNU-120596 (n=3). Curves through data points are the best fit obtained with the empirical Hill equation. Plot of the peak inward current as a function of the logarithm of the ACh concentration yielded typical concentration-response curves that are readily fitted by the empirical Hill equation. See Table 2. Pre-application of IVM, 5HI, NS-1738, and PNU-120596 yielded a series of concentration-activation curves with typical profiles of positive allosteric modulators—increase in the amplitudes of the peak ACh-evoked currents, leftward shift in concentration-activation curves, and increased steepness of the slope of the concentration response curve. Exposure of oocytes expressing the 5HT3 receptor to NS-1738 or PNU-120596 caused no significant modification of the subsequent response evoked by the agonist (data not shown). The ratio of potentiation obtained for the α7 and 5-HT3 receptor to a fixed exposure to NS 1738 and PNU-120596 are illustrated in FIG. 10.

When similar experiments were performed at Chimera 1, in which the extracellular domain of α7 is fused at position 201 to the 5HT3 receptor, strikingly different results were observed. Whereas NS-1738 retained a marked potentiation of ACh-evoked current at Chimera 1, PNU-120596 failed to elicit any increase in ACh-evoked current. This suggests that energy barriers for the transition from resting to the active state of Chimera 1 are different from those of α7 nAChR or that the PNU-120596 failed to bind and modulate this receptor.

To examine further the structural determinants of allosteric modulation, effects were tested using Chimera 2, which corresponds to Chimera 1, but with the M2-M3 segment from the 5-HT3 replaced with a corresponding α7 amino acid segment. Data obtained for the four allosteric modulators (IVM, NS-1738, 5HI and PNU-120596) are illustrated in the lower panel of FIG. 10.

Figure 10:
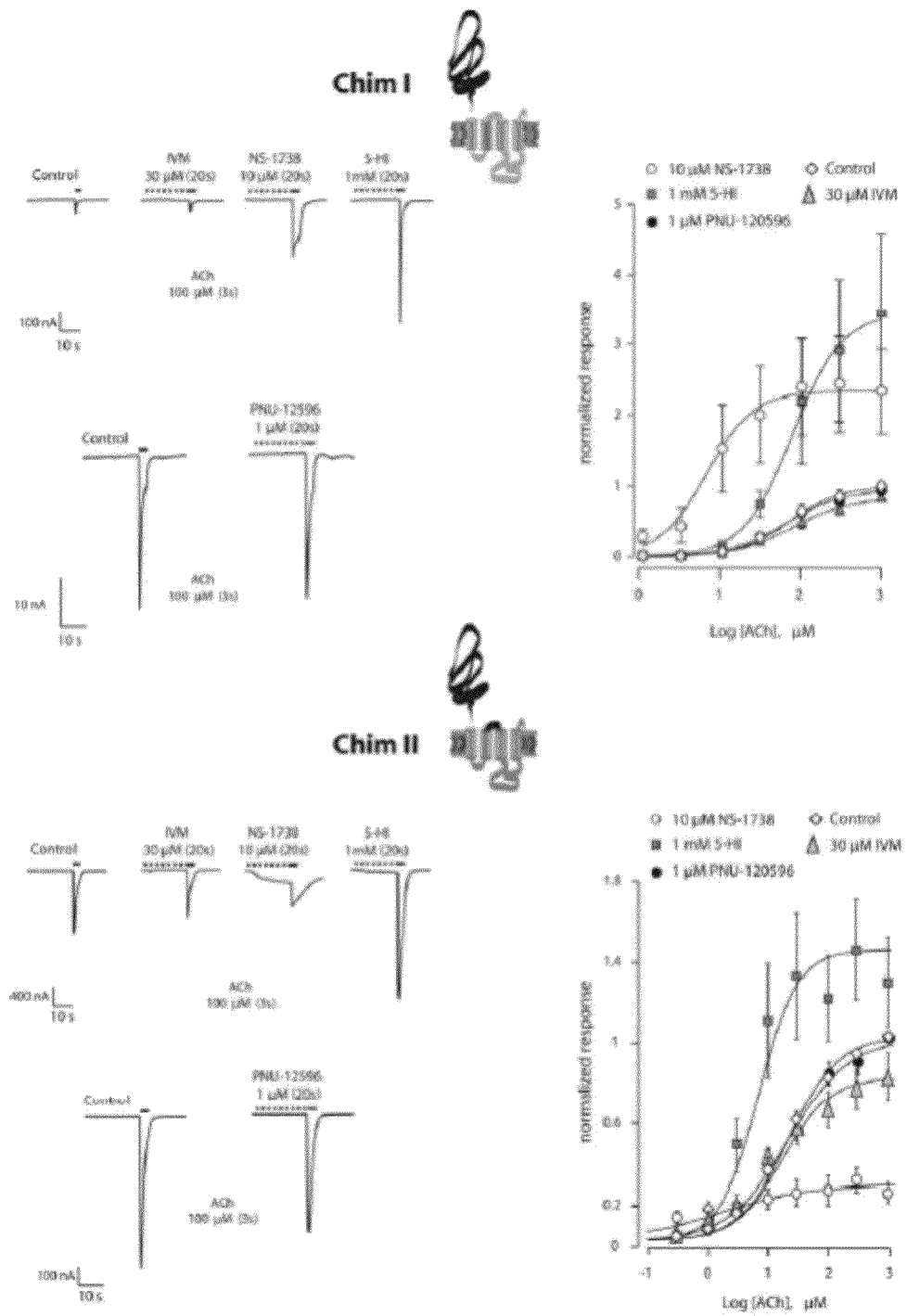
FIG. 10. Effects of four positive allosteric modulators at Chimeras I and II. Schematic representation of the α7-5HT3 fusion protein (Chimera 1; dark line indicates the α7 segment) is illustrated at the top together with the effects of the four modulators on the ACh-evoked currents and on the concentration-activation curves. Note the absence of effects of PNU-120596 and IVM, whereas a positive modulation is still observed with the 5-HI or the NS-1738. Cells were constantly held at −100 mV. Bottom, schematic representation and functional properties of Chimera 2, in which the N-terminal extracellular domain and the extracellular segment delimited by M2 and M3 have been replaced with that of α7 (dark line). Typical ACh-evoked currents measured first in control and after exposure to allosteric modulators are represented at bottom left and concentration-activation curves measured as for Chimera 1 are shown at bottom right. Curves through data points are the best fits obtained with the empirical Hill equation (see Materials and Methods). Corresponding coefficients are presented in Table 2.
Figure 11:
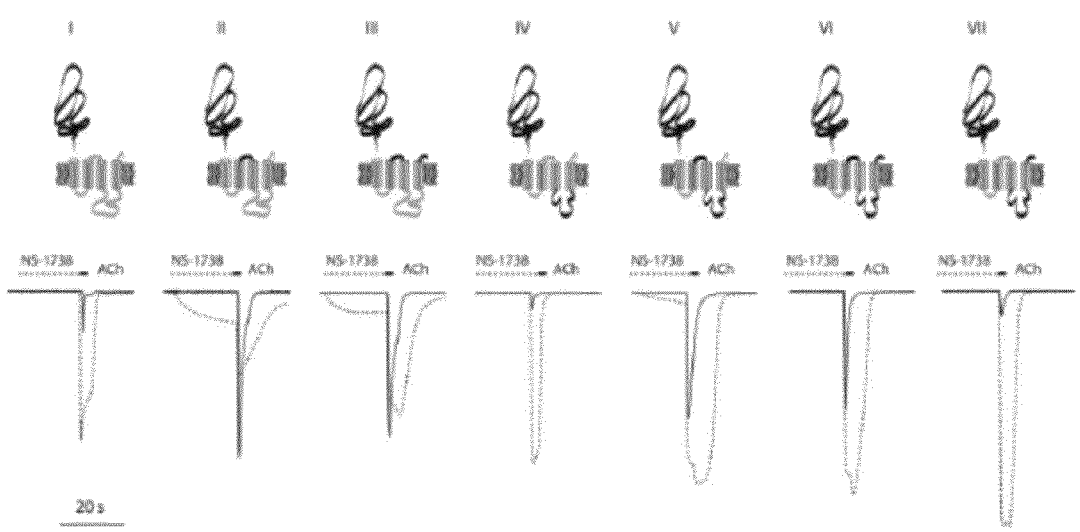
FIG. 11. Summary of the modulation caused by the NS-1738 at Chimera 1-7 contructs. Typical ACh-evoked currents recorded first in control conditions (continuous line) and after 20-s exposure to 10 μM NS-1738 for a series of chimeras are illustrated (dashed lines). Comparable recordings were obtained in at least three cells. Schematic representations of the corresponding Chimera constructs (1-7) are shown above each recording. Dark segments symbolize α7 amino acid sequences; gray lines represent the 5-HT3 segments.

Exposure of Chimera 2 to the NS-1738 alone evoked a significant inward current showing no desensitization over the 20 s of pre-application (FIGS. 10 and 11). Furthermore, the subsequent ACh-evoked response was significantly inhibited. A possible hypothesis that could explain both the sustained inward current and inhibition of the ACh evoked response is that substitution of the M2-M3 segment caused a reduction of the energy barrier between the resting and active state and that further reduction caused by exposure to the positive allosteric modulator NS-1738 is seen as spontaneous opening in absence of ligand. In agreement with this hypothesis, application of the competitive antagonist dihydro-β-erythroidine hydrobromide inhibited the inward current observed during the NS-1738 exposure (data not shown).

Figure 12:
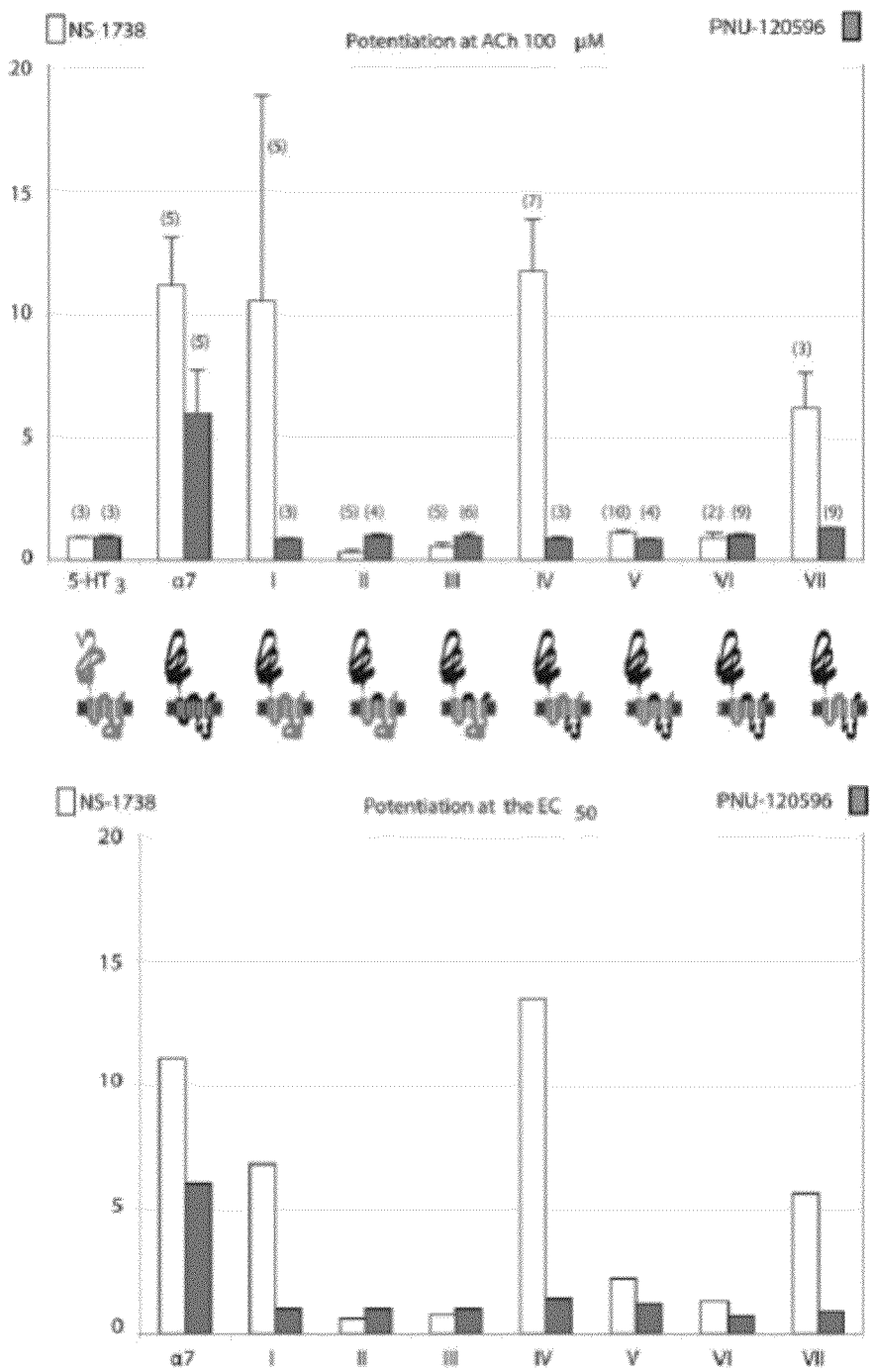
FIG. 12. Allosteric potentiation of Chimera 1-7 by the NS-1738 and PNU-120596. Plot of the potentiation ratio for the control receptors and seven Chimeras. Peak of the ACh-evoked currents recorded after a brief exposure to NS-1738 (10 μM, 20 s, empty boxes) were measured and the ratio versus control responses determined (top). Plot of the average potentiation ratio and S.E.M. are represented. Number of cells tested for each mutant and each condition are indicated in parenthesis. Note the absence of potentiation for the 5-HT3 receptor but significant potentiation in the Chimeras. Filled boxes represent the potentiation ratios determined using the same procedure for 1 μM PNU-150596. To best evaluate the potentiation caused by the NS-1738 and PNU-120596, measurements were repeated near the respective ACh sensitivity of each chimera subtype (bottom). Note the lack of potentiation for the PNU-120596 for the 5-HT3 receptors and the seven chimeras.

Activation of a current and subsequent inhibition of the ACh-evoked response observed after exposure to NS-1738 is reminiscent of the properties that would be exhibited by a partial agonist. To evaluate this possibility, further experiments were designed in which cells were exposed to a series of NS-1738 concentrations. Although important variations in the amplitude of the NS-1738-evoked currents were noticed between different cell batches, detectable currents were observed only for concentrations above 3 μM, but further increasing the NS-1738 concentration led to a reduction of this current (data not shown). This indicates either that this compound does not act as a partial agonist or that it causes both activation and blockade of the receptor. While Chimera 2 yielded robust ACh-evoked currents and showed sensitivity to NS-1738, preapplication of the PNU-120596 failed to increase the subsequent ACh-evoked responses (FIG. 12).

To fully reconstitute the α7 extracellular domain in the α7-5HT3 chimera, another chimera (Chimera 3) in which the N-terminal domain, the M2-M3 segment, and the M4-C-terminal end from the α7 subunit was constructed and evaluated. Incorporation of the α7 C-terminal fragment, however, caused no substantial differences in the biophysical and pharmacological properties compared with Chimera 2. PNU-120596 failed to potentiate this Chimera, whereas opening of the channels upon application of NS-1738 alone was observed (FIG. 11). It is noteworthy that of the seven Chimeras tested, constructs that contained the α7 M2-M3 segments displayed sustained activation when exposed to NS-1738 alone (FIG. 12). Because the ensemble of the protein structure defines properties of the receptor, modifications introduced in the different constructs might result in variation in their respective ACh sensitivities. Determination of the half-activation (EC50) for each of the seven Chimeras revealed a range of up to 10-fold differences in ACh sensitivities. To best characterize the effects of the NS-1738 or the PNU-120596, potentiation of currents evoked by ACh concentrations near the respective EC50 values were also determined (FIG. 12, bottom). The similitude observed between data obtained at 100 µM ACh and near the EC50 indicates that results obtained at a single agonist concentration give a good prediction of the overall sensitivity of the receptor to the allosteric modulator. Data presented in Table 3 summarize the shifts in ACh sensitivities caused by exposure to either NS-1738 or PNU-120596. These data confirm the lack of effect of PNU-120596 at the seven chimeras, and that Chimeras 2 and 6 show the largest displacement in the ACh sensitivity caused by the NS-1738.

In light of the inability to restore potentiation by PNU-120596 in chimeras incorporating the α7 extracellular segments, it remained possible that PNU-120596 interacts with the intracellular domain of the receptor. To test this, Chimeras 4-7 comprising the large intracellular loop of the α7 subunit, were designed and constructed. See FIG. 12. Although all chimeras yielded functional receptors and displayed robust currents in response to ACh, none of these constructs showed an increase of the peak-evoked response after a 10 µM pre-application with the PNU-120596. Likewise, no significant increase in the response duration was observed in these constructs indicating that structural features of these chimeras prevent the allosteric modulatory action of the PNU-120596.

Figure 13:
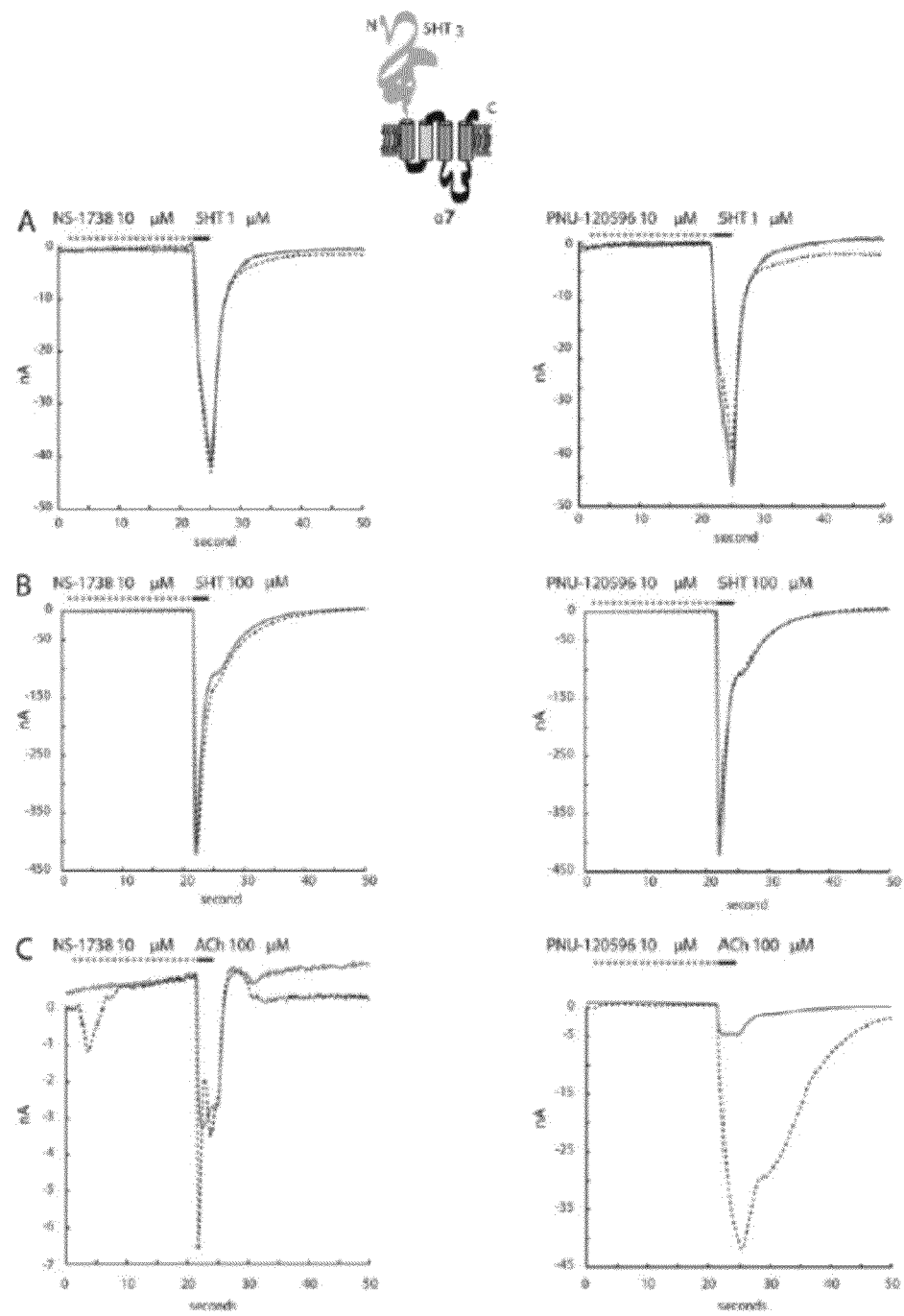
FIG. 13. Importance of the transmembrane domains for the potentiation by PNU-120596. Construction of the reverse 5HT3-α7 chimera (Chimera 8) yielded 5-HT evoked currents in only a few oocytes injected with this fusion protein. Cartoon represented above the traces illustrates the schematic structure of a single subunit inserted into the membrane. The gray line corresponds to the extracellular 5-TH3 receptor sequence, whereas the dark line indicates the α-7 segments. Despite the low yield of expression, significant and reproducible currents were evoked by brief exposure to 5-HT (continuous lines A and B). Exposure to NS-1738 (dashed lines, left) or PNU-120596 (dashed lines, right) caused no modification of the amplitude or time course of the 5-HT evoked currents (dashed lines). A, responses evoked by low 5-HT concentrations that are most susceptible to reveal a putative allosteric modulation. Small, but significant, currents were recorded when these cells were exposed to ACh. C, ACh-evoked currents measured in the same cell as A and B. Exposure to NS-1738 (dashed line) caused no modification of the subsequent ACh response, whereas a clear increase of the current was observed after exposure to PNU 120596 (dashed line).

To examine the putative role of the transmembrane domains, a reverse chimera comprising the 5-HT$_3$ ligand binding domain and the transmembrane domain of α7 was designed and constructed. Cell expressing the inverse chimera (Chimera 8) produced significant inward currents in response to 5-HT application. See FIG. 13. However, preapplication of either PNU-120596 or NS-1738 using the same protocol as for the α7 receptor caused no detectable modification of the subsequent 5HT-evoked current. See FIGS. 13A and B. To best evaluate a putative allosteric modulation, currents evoked by low agonist concentration were also investigated, but exposure to either NS-1738 or PNU-120596 caused no detectable modification of the response amplitude or time course. See FIG. 13B. Because cross talk between α7 and the 5HT3 receptors has often been reported, the possible effects of ACh and the positive allosteric modulators were examined. It was surprising to find that ACh evoked small, but reproducible, currents that were recorded in Chimera 8 and these effects were potentiated by the PNU-120596 but not by NS-1738. See FIG. 13C. Addition of ACh on a low 5-HT concentration+/−PNU 120596 was not distinguishable from ACh alone. Data not shown. With specific respect to FIG. 13, construction of the reverse 5HT$_3$-α7 chimera (Chimera 8), yielded 5-HT evoked currents in only a few oocytes injected with this fusion protein. The cartoon above the traces in FIG. 13 illustrates the schematic structure of a single subunit inserted into the membrane. The gray line corresponds to the extracellular 5HT$_3$ receptor sequence, whereas the dark line indicates the α7 segments. Despite the low yield of expression, significant and reproducible currents were evoked by brief exposure to 5-HT. See the continuous lines in 13A and B. Exposure to NS-1738 (dashed lines, left) or PNU-120596 (dashed lines, right) caused no modification of the amplitude or time course of the 5-HT evoked currents (dashed lines). In FIG. 13A, small, but significant, currents were recorded when cells were exposed to ACh. FIG. 13C, shows ACh-evoked currents measured in the same cell as in FIGS. 13A and B. Exposure to NS-1738 (dashed line) caused no modification of the subsequent ACh response, whereas a clear increase of the current was observed after exposure to PNU-120596 (dashed line).

Based on Examples 2 and 3, the observation that Chimera 1 is modulated by the NS-1738 indicates that introduction of the α7 N-terminal domain is sufficient to allow potentiation by this compound. On the contrary, the lack of modulation of Chimera 1 by the PNU-120596 indicates that this compound interacts with a distinct protein domain than the NS-1738. Progressive introduction of the extracellular and intracellular domain from α7 into the Chimera (I-7) revealed the critical role played by the short M2-M3 extracellular domain. Introduction of this amino acid segment was sufficient to cause a modification of the sensitivity to the NS-1738 with the apparition of an inward and dihydro-β-erythroidine-sensitive current upon exposure to NS-1738. By comparison, site-directed mutagenesis of the M2-M3 loop previously pointed out the relevance of this short segment in controlling the current amplitude versus amount of α-bungarotoxin binding, and it was hypothesized that this segment could play a role in the receptor gating (Castillo et al., 2006). A simple hypothesis accounting for such observation is that Chimera 2 displays a lower energy barrier between the resting and active state and that further reduction of this barrier causes spontaneous opening that resembled that observed in α7 mutants (Bertrand et al., 1997). Alternatively, it could be postulated that binding of NS-1738 partially activates the Chimera 2 receptor, which could explain the reduction of the subsequent ACh-evoked current by desensitization. Because NS-1738 evoked a small fraction of the ACh response that was variable from batch to batch, it is difficult to make conclusions about the mechanism by which NS-1738 causes opening of the Chimera 2 receptor. The determinant role of the M2-M3 further support previous observations made either on the GABA$_A$ and nAChRs (Kash et al., 2003; Lee and Sine, 2005; Lummis et al., 2005). No major modification of the sensitivity either to NS-1738 or to PNU-120596 was observed upon introduction of the α7 C-terminal domain (Chimera 3). A plausible postulate was that PNU-120596 could interact with the intracellular domain of α7 and that introduction of this amino acid segment might restore its potentiation. Construction of Chimera 4-7, however, failed to identify a segment that would restore PNU 120596. In the view of the high degree of sequence homology observed between the short M1-M2 segments of the α7 and 5-HT3 receptors, it is unlikely that the PNU-120596 effects are mediated through the interaction with this portion of the protein. All together, these data suggest that PNU-120596 probably interacts with one or more transmembrane domain of the receptor, whereas the NS-1738 interacts with the extracellular N-terminal domain. In agreement with this hypothesis, Chimera 8, which comprises the transmembrane domain of α7 but the N-terminal domain of the 5-HT3, shows a potentiation of ACh-evoked current. The relevance of the transmembrane segment in regulating the potentiation of the PNU-120596 is best understood in light of previous work carried out by photoaffinity labeling at the GABAA receptors, which identified the contribution of a single amino acid residue in M1 of the α subunit and another in the M3 of the β3 subunit in controlling the potentiation by the general anesthetic etomidate (Li et al., 2006). This suggests that, as proposed for the etomidate potentiation, the PNU-120596 might interact with the transmembrane segments and alter the energy barriers between the different states. Furthermore, it is important to note that although both NS-1738 and PNU-120596 belong to the biarylurea class of PAMs, there are differences in the substitution patterns on the aryl rings (for example, isoxazole in case of PNU-120596 versus substituted phenyl in case of NS-1738; FIG. 1); accordingly, there are differences in the log P values (~2.8 versus ~4.8, respectively). These differences can influence allosteric modulatory interactions of these two compounds at α7 nAChRs. The emergence of structurally distinct PAMs of different in vitro profiles offers valuable tools with which to further define the physiology and pharmacology of α7 nAChR transmission. For example, both types of PAMs have been reported to show in vivo efficacy in animal models of cognition and sensory gating deficit, although the underlying molecular mechanisms remain to be defined (Hurst et al., 2005; Ng et al., 2007). Our studies with α7 nAChRs show that both type I and II modulators cause, as expected for a positive allosteric modulator, a shift of the dose response toward lower ACh concentration, increase in the steepness of the curve (Hill coefficient), and increase in the maximal evoked current. Our investigation of the molecular mechanisms underlying PAM effects demonstrates key distinctions in the sites of action of these types of PAMs. In particular, we show, using recombinant Chimeras between extracellular domain of α7 nAChR and 5-HT3 receptors, that NS-1738 and PNU-120596 interact at distinct sites on the receptors and that amino acid residues of the M2-M3 loop control current activation evoked by PAMs such as NS-1738.

Example 4

Differential Effects of Nicotinic Agonists in Chimeras

Figure 14:
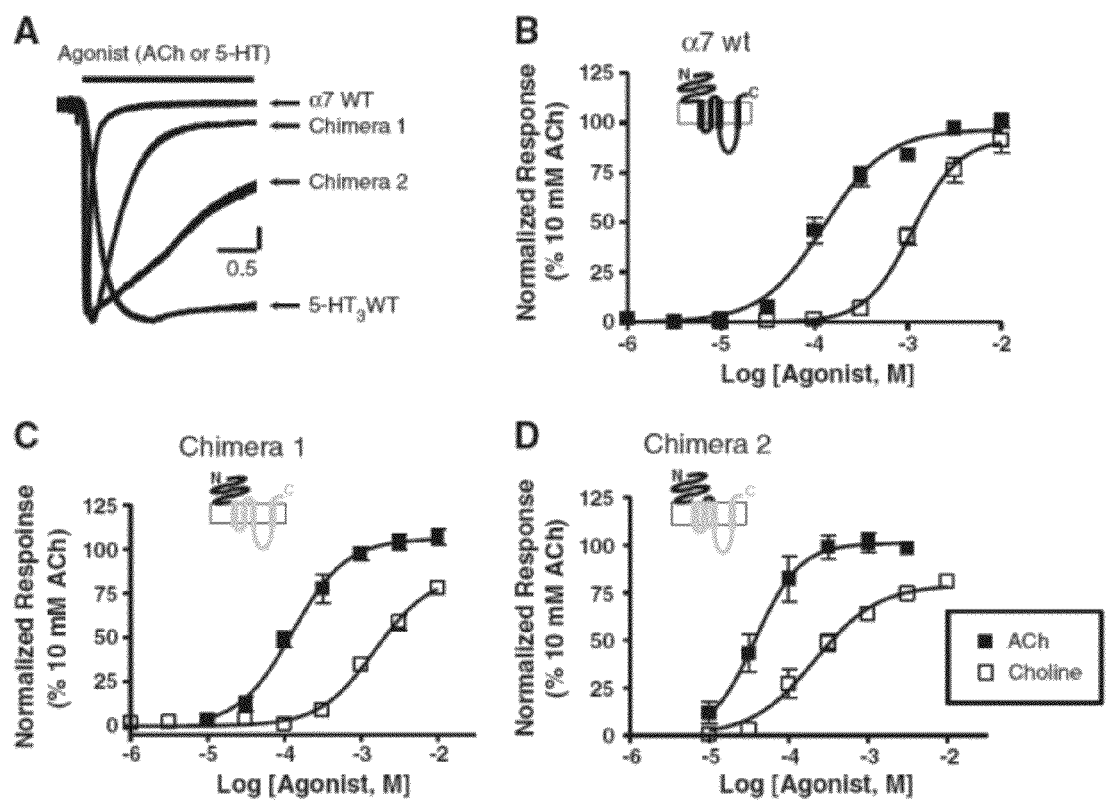
FIG. 14. Agonist-evoked responses at wild-type α7, wild-type 5-HT$_{3A}$, and chimeric constructs measured electrophysiologically. Panel (A) depicts representative current responses of the expressed receptors in *Xenopus* oocytes to maximally effective concentrations of agonists (10 mM ACh for Chimera 1, 2, and α7 nicotinic acetylcholine receptor, and 30 μM for 5-HT). The Y-axis is scaled to the maximum amplitude. Note differences in kinetic profiles, see text for description of decay constants. Panels (B-D) summarize the concentration-responses to ACh (■) and choline (□) for wild-type α7 (B), Chimera 1 (C), and Chimera 2 (D) receptors. Potency values are summaries in Table 1. The mean±S.E.M. maximum efficacy values are: 101±2% for ACh/Chimera 1 receptors, 91±7% for choline/Chimera 1 receptors, 107±4% for ACh/Chimera 2 receptors, 78±4% for choline/Chimera 2 receptors, 101±5% for ACh/wild-type α7 nicotinic acetylcholine receptors, and 81±4% for choline/wild-type α7 nicotinic acetylcholine receptors. The inset within each graph shows graphical representation of human α7 (dark) and 5-HT3A (light) receptor sequences encoding the various constructs. Each data-point is n=3-11.

The effects of two structurally different α7 PAMs of the α7 nicotinic acetylcholine receptor, 5-HI and genistein, on Chimera 1 and Chimera 2 were studied in order to identify and compare the domains critical for the allosteric potentiation of the receptor. Chimera 1 and Chimera 2 were transiently expressed in *Xenopus* oocytes and stably in HEK-293 cells. Agonist concentration-responses were then determined using two-electrode voltage clamp in oocytes, and by patch clamp and membrane potential dye imaging (FLIPR) in HEK-293 cells expressing the chimeric constructs. ACh- and choline-evoked currents in oocytes expressing chimeric 1 and 2 receptors, and wild-type α7 nicotinic acetylcholine receptors. For all three receptors, ACh was more potent than choline by ~10 fold when analyzing the maximum-evoked peak current amplitude response. Overall the receptor sensitivity to the two agonists was as follows: Chimera 2>Chimera 1~wild type α7 (See Table 4). For example, for ACh the $EC_{50}$ values were ~130 μM for Chimera 1 and wild type α7 receptors, and ~40 μM for Chimera 2 revealing ~3-fold difference. In the case of choline, the responses were 5-7-fold different favoring Chimera 2 receptors over Chimera 1 receptors and α7 nicotinic acetylcholine receptors. At wild-type human 5-HT3A receptors, choline failed to activate any current up to the highest concentration tested of 10 mM whereas ACh did so only marginally, weak current activation of ~30% at 10 mM (see Table 4). In comparison, 5-HT activated human 5-HT3A current with mean EC50 value of 1.5 (1.2-1.8, 95% C.I.) μM (n=6) and 100% maximum activation. Qualitatively the agonist-evoked currents in oocytes expressing the Chimeras exhibited different properties. Although the upstroke phase for the two Chimeras and wild-type α7 showed similar kinetics, the current decay was more rapid for wild-type α7 receptor followed by Chimera 1 and Chimera 2 receptors. For example when currents were evoked by 10 mM ACh, in the continued presence of the agonist the respective $\tau_{decay}$ values for Chimera 1, Chimera 2, and wild-type α7 receptors were 423.4±20.6 ms (n=4), 3281.3±686.0 ms (n=5), and 269.0±28.2 ms (n=4). Wild-type human 5-HT3A receptor mediated current responses activated and decayed much more slowly, often being non-decaying, precluding analysis of its τ decay (see FIG. 14A).

Figure 15:
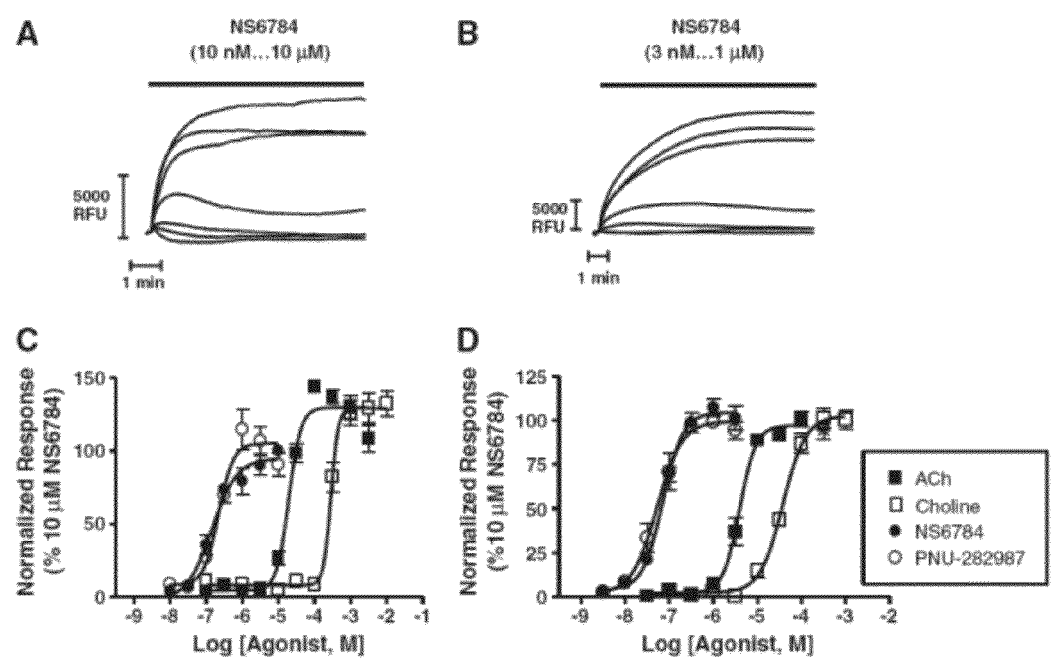
FIG. 15. Summary of agonist-evoked responses at the chimeric α7/5-HT$_{3A}$ receptors measured using membrane potential imaging. Panels (A) and (B) depict representative membrane potential imaging responses to increasing concentrations of NS6784 for Chimera 1 and 2 receptors, respectively. Panels (C, Chimera 1) and (D, Chimera 2) summarize the mean concentration-responses to NS6784, PNU-282987, ACh, and choline, see Table 1 for summary of potency. The mean±S.E.M. maximum efficacy values are: 132±9% for choline/Chimera 1 receptors, 144±3% for ACh/Chimera 1 receptors, 100% for NS6784/Chimera 1 receptors, 107±9% for PNU-292987, 101±6% for choline/Chimera 2 receptors, 101±4% for ACh/Chimera 2 receptors, 107±5% for NS6784/Chimera 2 receptors, and 99±2% for PNU-282987/Chimera 2 receptors. Each data-point is n=4-8; see Table 1 for summary of potency.

In addition to electrophysiological recordings, we have also carried out imaging experiments in HEK-293 cells expressing separately Chimera 1 and 2 receptors using FMP measurements. Specifically concentration-responses were determined to ACh, choline, NS6784, and PNU-282987. As summarized in FIG. 15 and Table 4, in both cell lines the rank order of potency was: NS6784~PNU-282987>ACh>choline. Comparison of the EC50 values for each agonist revealed that compounds were ~2-8 fold more potent in Chimera 2 than Chimera 1 HEK-293 cells (P<0.05 for comparison, see Table 4). The shifts appeared more pronounced for ACh or choline (~5 and 8-fold) than the synthetic agonists (~2 and 4-fold). These observations indicate that agonists were more effective in terms of potency in evoking responses by Chimera 2 than Chimera 1 receptors, confirming a critical role of M2-M3 loop for fine-tuning the channel activation.

Example 5

Figure 16:
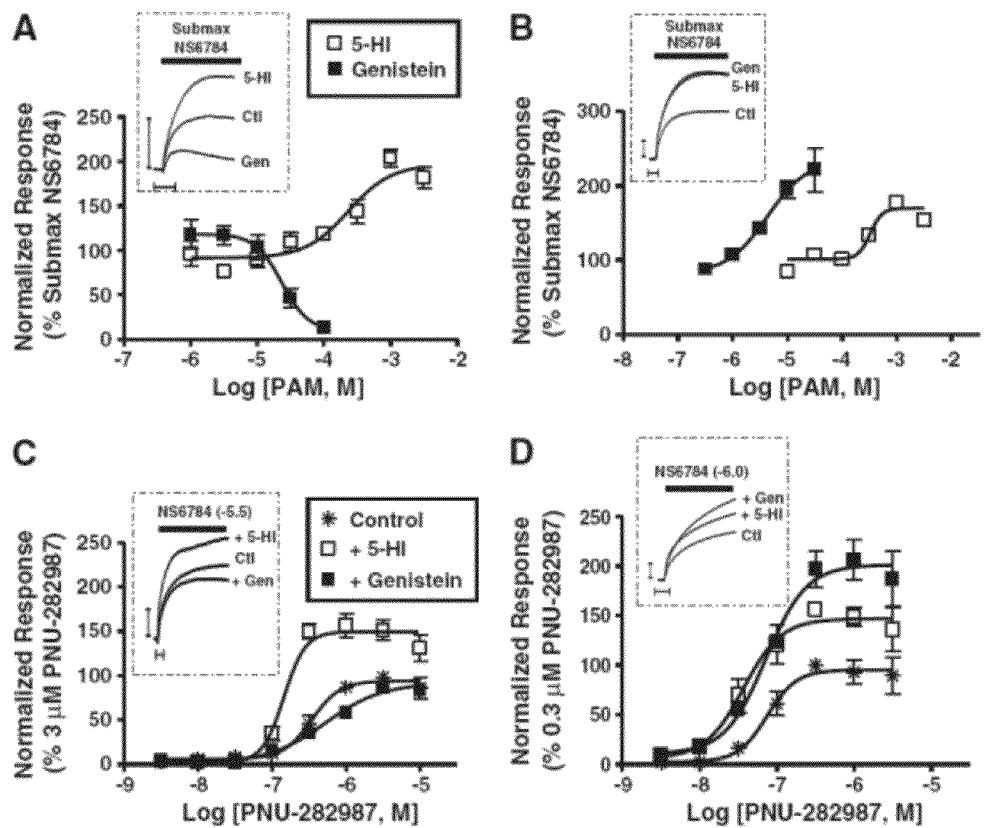
FIG. 16. Summary of effects of genistein and 5-HI on agonist-evoked membrane potential depolarization in chimeric HEK-293 cells. Shown are mean concentration-responses to increasing concentrations of 5-HI (□) and genistein (■) in Chimera 1 (panel A) and Chimera 2 (B) receptors on submaximumagonist (NS6784)-evoked responses (120-200 nM for Chimera 1 and 60-70 nM for Chimera 2). The mean±S.E.M. values for maximum positive allosteric modulation efficacy of genistein at Chimera 1 and 2 receptors are 14±3% and 221±30%, respectively. For 5-HI the corresponding values are 204±9% at Chimera 1 receptors, and 177±8% at Chimera 2 receptors. See Table 1 for summary of potency. Panels (C, Chimera 1) and (D, Chimera 2) illustrate the mean concentration-responses to PNU-282987 obtained in the presence of 10 μM genistein (■), 1 mM 5-HI (□), or their absence (*, control). At Chimera 1 receptors, PNU-282987 concentration-response parameters are: EC50 of 343 (276-426) nM and maximum efficacy of 98±2% for control, 527 (357-777) nM and 87±3% in the presence of genistein, and 145 (108-194) nM and 157±13% in the presence of 5-HI. At Chimera 2 receptors, PNU-282987 concentration-response parameters are: 75 (50-113) nM and 100±0.01% for control, 72 (46-112) nM and 207±21% in the presence of genistein, and 37 (22-62) nM and 156±4% in the presence of 5-HI. The upper-left insets within each panel depict representative membrane potential imaging traces obtained (for simplicity responses only to a single concentration are included). For panels (A) and (B), 5-HI (1 mM), genistein (Gen, 30 μM for A, and 10 μM for B), or blank control (Ctl) were added for at least 5 min prior to the addition of submaximum NS6784. In panels (C) and (D), the responses to NS6784 (3 μM for C, and 1 μM for D) were measured in the presence of 1 mM 5-HI, 10 mM genistein (Gen), or without (Ctl). Compound additions were as specified by the horizontal bars. Genistein enhanced agonist-evoked depolarization in Chimera 2 but was unable to do so in Chimera 1; 5-HI was effective in both Chimeras. Each data-point is n=3-9.
Figure 17:
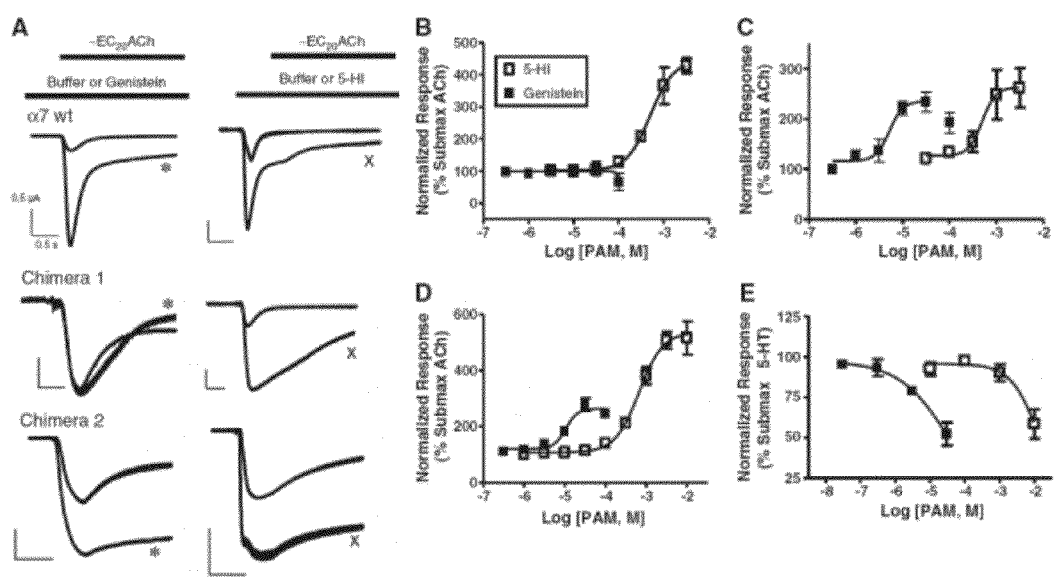
FIG. 17. Differential modulation effects of genistein and 5-HI at chimeric and wild-type receptors expressed in *Xenopus* oocytes. Panel (A) depicts representative current responses measured at wild-type α7, Chimera 1, and Chimera 2 receptors to the submaximum application of ACh (as indicated by the horizontal bar) in the absence or presence of genistein (left traces) and 5-HI (right traces), '*' and 'X' indicate traces measured in the presence of genistein (30 μM for wild-type α7, 100 μM for Chimera 1, and 10 μM for Chimera 2 receptors) and 5-HI (3 mM for wild-type α7, 1 mM for Chimera 1 and 2 receptors). Panels (B-E) summarize the modulator concentration-responses. Shown are the mean concentration-responses for genistein (■) and 5-HI (□) when tested at Chimera 1 (panel B), Chimera 2 (C), wild-type α7 nicotinic acetylcholine (D), and wild-type 5-HT3A (E) receptors. Responses are expressed as percentage potentiation of submaximum agonist-evoked responses (100 μM ACh for Chimera 1 and α7, 10-30 μM for Chimera 2, or 1-3 μM5-HT for 5-HT3A). The mean±S.E.M. values for genistein and 5-HI, respectively, are 65±27% and 428±23% for Chimera 1 receptors, 234±19% and 262±39% for Chimera 2 receptors, 246±17% and 516±59% for wild-type α7 nicotinic acetylcholine receptors, and 52±7% and 58±9% for wild-type 5-HT3A receptors. Potencies are summarized in Table 2. Each data-point is n=3-12.
Figure 18:
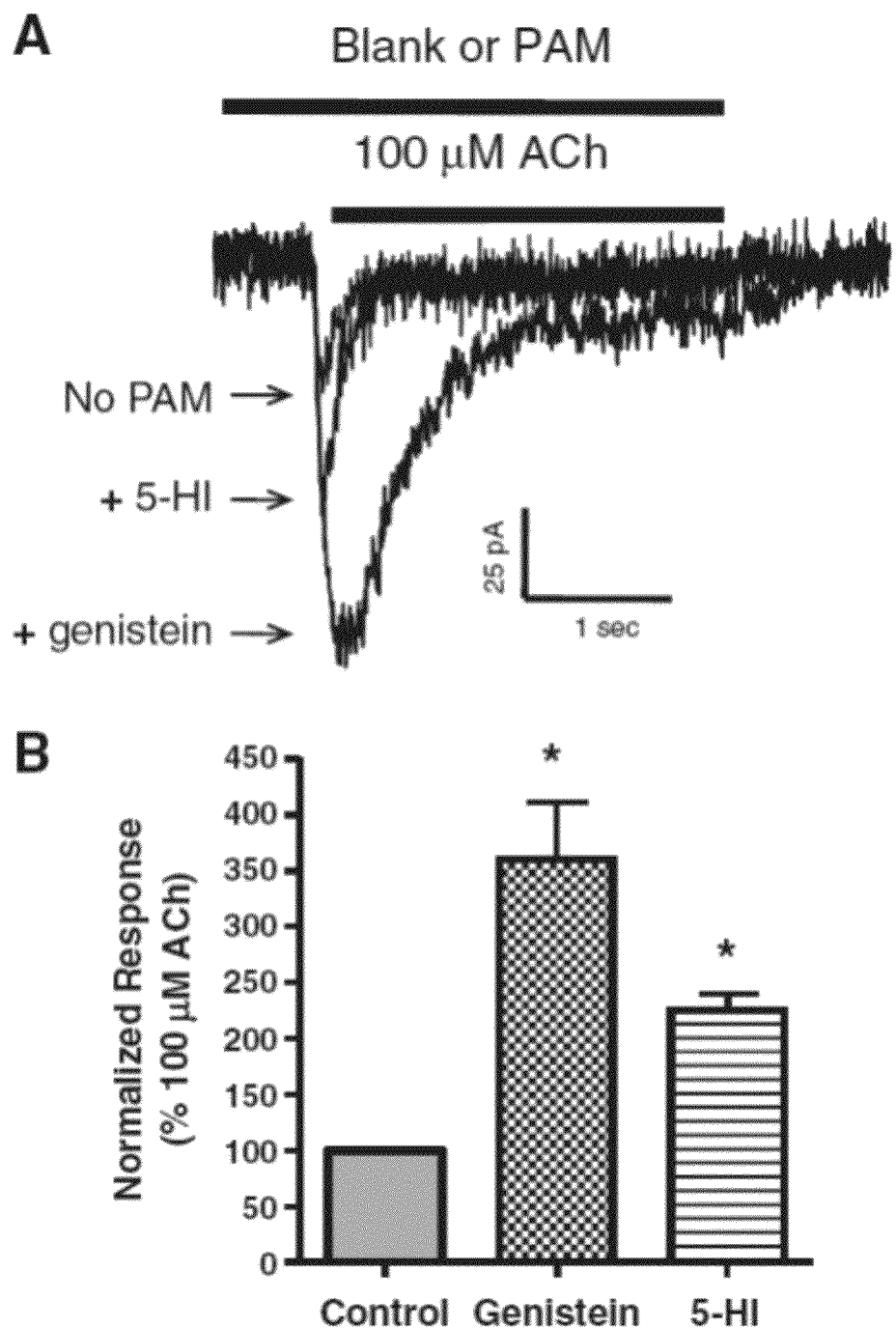
FIG. 18. Summary of modulation concentration-responses for genistein and 5-HI at the Chimera 2 receptors expressed in HEK-293 cells. Panel (A) depicts representative current responses measured using whole cell patch clamp method to the application of ACh in the presence of 5-HI (1 mM), genistein (50 μM), or black added as preincubation for ~60 s as indicated. Panel (B) summarizes to mean efficacy responses to ACh obtained in the presence of genistein (30-50 μM) and 5-HI (1 mM), expressed as percentage potentiation over baseline. * indicates Pb0.05 (Student's t test); each datapoint is n=3-5.

Selective Potentiation of Chimera 2 but not Chimera 1 Receptors by Genistein in Contrast to 5-HI Studies were undertaken to characterize the effects of 5-HI and genestein on ACh-evoked currents in Chimera 1 and 2 receptors. Pretreatment with 5-HI, but not genistein, potentiated the submaximum α7 agonist (NS6784) evoked membrane potential depolarization in Chimera 1 expressing HEK-293 cells. See FIGS. 16A and B. Both compounds were effective as positive allosteric modulators at Chimera 2 HEK-293 cells. The effects of 5-HI at both Chimeras were comparable (EC50 values ~200-300 μM). In contrast, genistein inhibited Chimera 1 and potentiated Chimera 2 receptors (modulator EC50 value ~5 μM) illustrating differential effect of genistein. To further characterize the effects of 5-HI and genistein at the two chimeras, concentration-responses to another selective α7 agonist, PNU-282987, were determined in the presence of control (blank), 1 mM 5-HI, or 10 μM genistein. These concentrations were chosen based on their effects at Chimera 2 receptors being higher than their modulator EC50 values (see FIG. 16B). As shown in FIG. 16(C,D), genistein enhanced the concentration-responses to this agonist in Chimera 2 only and not Chimera 1. 5-HI was effective in both chimeras. These experiments, hence, suggest an obligatory role of the M2-M3 loop in regulating the positive allosteric modulation effect of genistein at the α7 nicotinic acetylcholine receptor based on the observations made. A major limitation of the membrane potential imaging is that this method does not directly assess the effects on the channels or evoked current-responses but indirectly via depolarization requiring at least 5 min or more to reach a steady-state level. To confirm that 5-HI and genistein exhibit differential effects, electrophysiological measurements were made in *Xenopus* oocytes expressing the various constructs. As shown in FIG. 17, genistein both in Chimera 2 and wildtype α7, but not Chimera 1, increased the submaximum ACh-evoked currents by ~2-3-fold with comparable EC50 values of ~5 and 10 μM (*Xenopus* oocyte expression, PN0.05, non-significant difference for Chimera 2 versus α7 receptors). 5-HI enhanced ACh-evoked currents in both Chimeras and wild-type α7 with comparable potencies (see Table 5, *Xenopus* oocyte expression, EC50 values of ~500-700 μM). For comparison, genistein and 5-HI were also tested at 5-HT3A receptors expressed in *Xenopus* oocytes for their abilities to modulate submaximum 5-HT-evoked current responses. Neither compound increased the responses. Instead weak inhibition was noted for genistein (~50% at 30 μM) and for 5-HI (~40% at 10 mM) (see FIG. 17E). Additionally, a set of experiments was carried out in HEK-293 cells expressing Chimera 2 receptors using whole cell patch clamp and fast solution application (allowing for much more rapid solution exchange than possible using the *Xenopus* oocyte expression system and FLIPR imaging under the conditions of the present study). Since we have already characterized the modulation concentration-responses for genistein and 5-HI in these Chimera 2 HEK-293 cells using FMP imaging (and *Xenopus* oocyte expression system), we focused on testing single high concentrations predicted to increase agonistevoked current responses. As shown in FIG. 18, both 5-HI and genistein were effective as positive allosteric modulators providing confirmatory observations for the requirement of the α7 encoded M2-M3 present in Chimera 2 for the effect of genistein, but not for 5-HI. At wild-type α7 nicotinic acetylcholine receptors, this loop may have a key role in modulating the effect of genistein.

Example 6

Direct Activation of Chimera 2 but not Chimera 1 by Genistein and 5-HI

Figure 19:
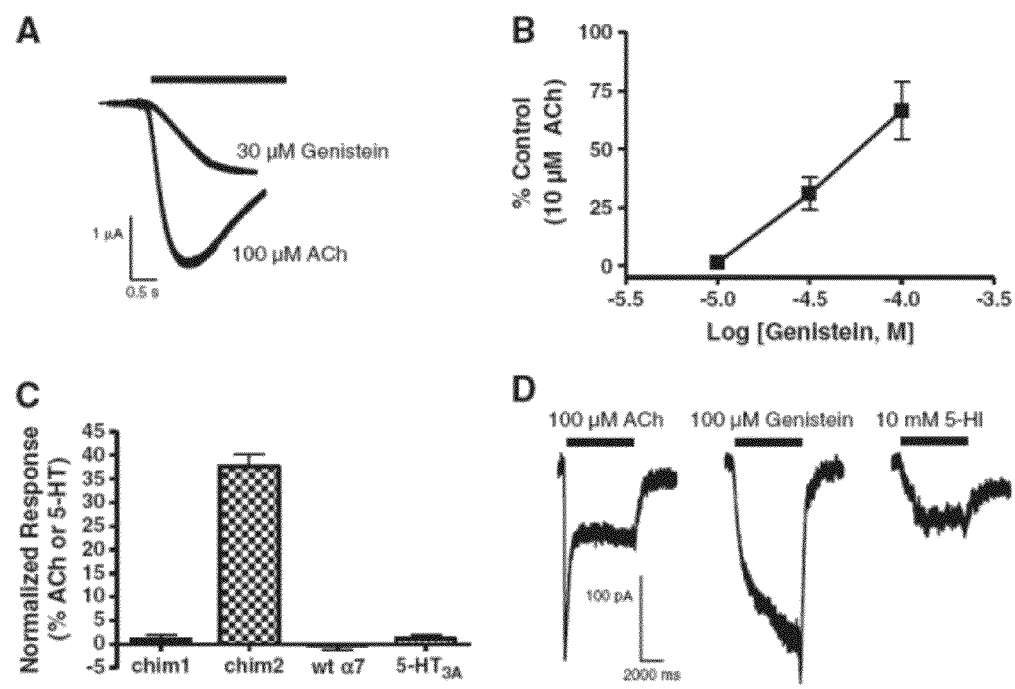
FIG. 19. Stimulation of agonist-like responses in Chimera 2 by genistein. Panels (A) and (D) depict representative current trace responses obtained in *Xenopus* oocytes expressing Chimera 2 (A) and in HEK-293 cells stably expressing Chimera 2 (D) to application of genistein, 5-HI or ACh as indicated by the horizontal bars. Note differences in kinetic profiles by ACh and genistein. Panel (B) summarizes the mean concentration-responses for genistein measured in *Xenopus* oocyte experiments (Chimera 2 expressing). Each data-point is n=5. Panel (C) depicts the responses to the direct addition of genistein (30 μM) measured in the various constructs. The reference agonists used are: ACh (100 μM) for Chimera 1 and wildtype α7, ACh (10-30 μM) for Chimera 2, and 5-HT (1-3 μM) for wild-type 5-HT3A receptors corresponding to EC20-EC40 efficacy for each construct. Only in Chimera 2, genistein and 5-HI (see text) evoked unique agonist-like current, each data-point is n=3-4. Panel (D) shows representative current responses measured in a single Chimera 2 HEK-293 cell to application of ACh, genistein, or 5-HI as indicated by the horizontal bars with at least 2 min washout interval in-between the additions.

The effects of genistein and 5-HI were determined as agonists in the two Chimera, and wild-type α7 and 5-$HT_{3A}$ receptors expressed in oocytes. As shown in FIG. 19, for Chimera 2, genistein activated currents at 30 and 100 μM, but it did not activate currents at 30 and 100 μM for Chimera 1, wild-type α7 or 5-$HT_{3A}$. The time course of activation was much slower and distinct from that observed from agonists such as ACh or choline. See FIG. 5 or 19A. In comparison, at 30 or 100 μM, genistein did not evoke currents in oocytes expressing Chimera 1, wild-type α7, or wild-type 5-$HT_{3A}$. See FIG. 19C. This indicates selective activation. Similarly, 5-HI at higher concentrations tested could also evoke responses in Chimera 2, but not Chimera 1, wild-type α7 or 5-$HT_{3A}$ receptors. At 1 and 3 mM, 5-HI, the Chimera 2 peak current amplitude responses were 5.4+/−1.8% and 37.8+/−11.6% (n=5) normalized to 10 μM ACh.

The direct effect of genistein (100 μM) was further investigated in Chimera 2 HEK-293 cells by patch clamp. See FIG. 19D. Similar to oocyte responses, genistein also directly activated the Chimera 2 receptor current in these cells with the profile of current activation being distinct from that of ACh. Whereas ACh-evoked current exhibited a clear upstroke, current decay, and usually a steady-state component (see FIG. 19 D), genistein-evoked responses were characterized by a relatively slow activation reaching a steady non-decaying phase. Qualitatively similar responses were also obtained by 5-HI (10 mM) but lower in magnitude (see FIG. 19 D). When normalized to 100 μM ACh, genistein (100 μM) and 5-HI (10 mM) evoked respective responses of 72.6±22.2% and 26.4±7.1% when analyzed as peak responses, and 162.5±5.3% and 52.4±10.3% (n=3 for all) for total charge (integral) determination. These experiments collectively demonstrate the abilities of genistein and 5-HI, both α7 positive allosteric modulators, to evoke direct current activation at concentration much higher than required for their modulation effect.

Example 7

Lack of Displacement of [$^3$H]A-585539 Binding by Genistein and 5-HI

Figure 20:
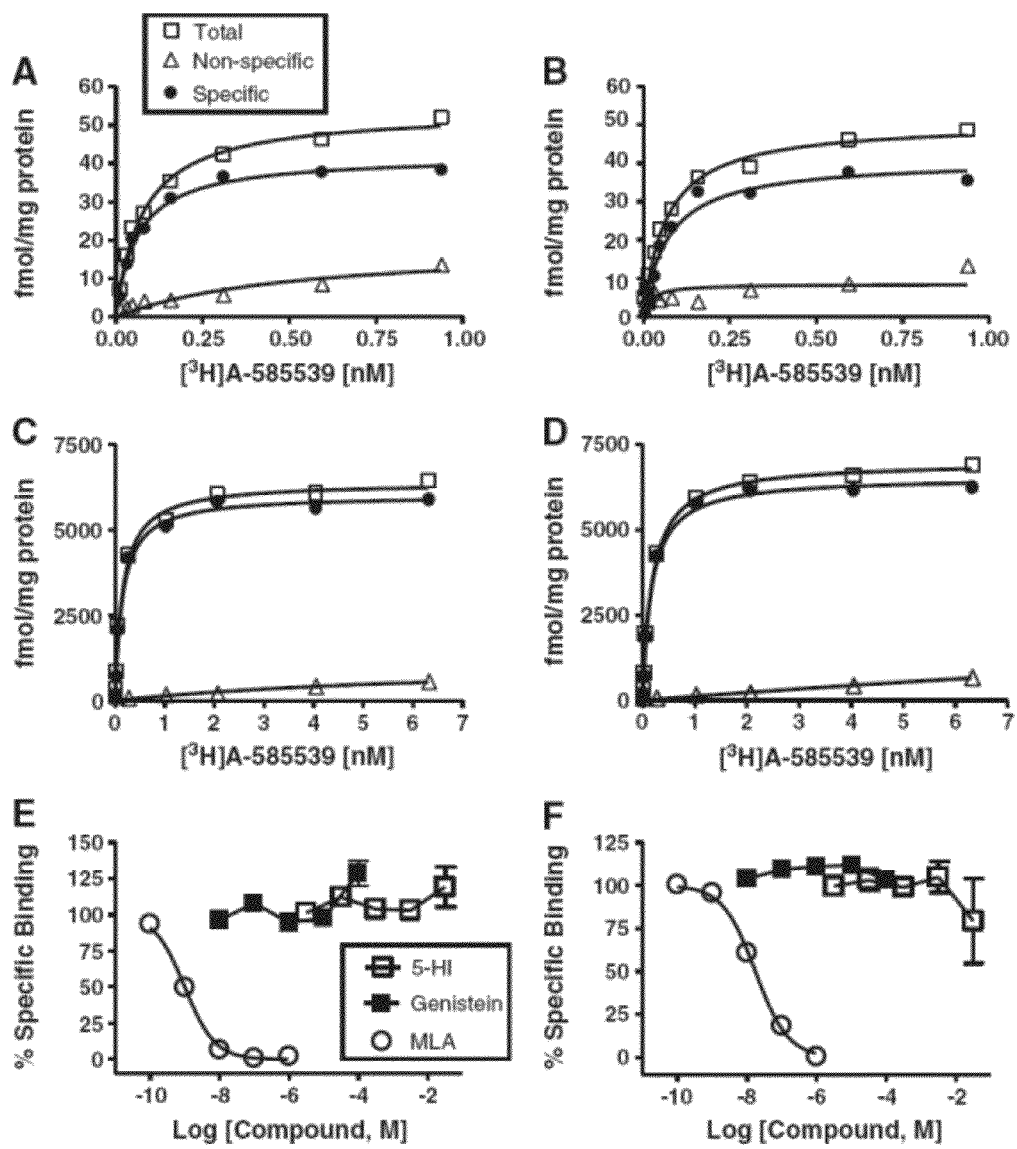
FIG. 20. Binding profile of [3H]A-585539 to rat brain and chimeric homogenates in the presence or absence of genistein and 5-HI. Representative saturation binding graphs are of [3H]A-585539 to rat brain (A, B) and Chimera 2 homogenates (C, D) in the absence (A, C) or presence (B, D) of 10 μM genistein. In these examples, the respective Kd and Bmax values are 0.062 nM and 42.0 fmol/mg protein (A), 0.071 nM and 40.9 fmol/mg protein (B), 0.15 nM and 6014 fmol/mg protein (C), and 0.17 nM and 6528 fmol/mg protein (D). Genistein did not alter the saturation binding of [3H]A-585539. The symbol legends specified in panel (A) also apply to panels (B-D). Panels (E, rat cortex) and (F, Chimera 2 receptor) summarize competition of [3H]A-585539 in the presence of increasing concentrations of genistein, 5-HI, and methyllycaconitine (MLA). Only methyllycaconitine competed with the binding of [3H]A-585539.

[$^3$H]A-585539 is a selective α7 nicotinic acetylcholine receptor ligand that binds to the orthosteric site of the receptor expressed both as a native (rat cortex) or α7/5-HT3 chimeric receptor (Malysz et al., 2009a; Anderson et al., 2008). In this study, saturation experiments were performed with this radioligand in the presence or absence of 10 μM genistein in homogenates prepared from rat brain and Chimera 2 HEK-293 cells. Representative single saturations from this series of studies are shown in FIG. 20 (A-D). Genistein at 10 μM did not alter the saturation profile for [3H]A-585539. In the rat brain, $K_d$ and $B_{max}$ values for of [3H]A-585539 binding were respectively 0.060±0.006 nM and 34.8±6.6 fmol/mg protein (n=3) without genistein, and 0.050±0.016 nM and 34.1 fmol/mg protein (n=3) in the presence of genistein. In the chimera, the values were 0.17±0.02 nM and 7016.0±798.2 fmol/mg protein (n=4) without genistein, and 0.18±0.01 nM and 7251.0±587.8 fmol/mg protein (n=4) in the presence of genistein using 20 μg/well, and were 0.11±0.01 nM and 5979.0±530.3 fmol/mg protein (n=4) without genistein, and 0.10±0.01 nM and 6058.0±809.3 fmol/mg protein (n=4) in the presence of genistein using 4 μg/well. In separate experiments, we investigated the degree of potential inhibition of the α7 agonist [3H]A-585539 binding to rat brain α7* nicotinic acetylcholine receptors and Chimera 2 receptors using competition assays carried out with increasing concentrations of 5-HI and genistein. As shown in FIG. 20 (C, rat cortex and D, Chimera 2), neither compound effectively displaced the binding of [3H]A-585539 at the concentrations in which they exhibited activities as positive allosteric modulators enhancing submaximum agonist evoking responses and directly evoking currents. These experiments, hence, confirmed the allosteric interaction of these compounds with the receptors examined.

TABLE 1

|  | Chimera 1 | Chimera 2 |
| --- | --- | --- |
| Electrophysiology (POETs) pEC$_{50}$ ± SEM | | |
| ACh | 3.9 ± 0.05 | 4.6 ± 0.06 |
| Choline | 2.9 ± 0.06 | 3.7 ± 0.08 |
| Radioligand Binding K$_D$ ± SEM | | |
| [$^3$H]A585539 | 0.65 ± 0.04 nM | 0.17 ± 0.02 nM |
| FLIPR-FMP pEC$_{50}$ ± SEM | | |
| NS6784 | 6.8 ± 0.10 | 7.1 ± 0.04 |
| PNU-282,987 | 6.8 ± 0.07 | 7.0 ± 0.04 |
| ACh | 4.7 ± 0.03 | 5.4 ± 0.03 |
| Choline | 2.9 ± 0.06 | 4.4 ± 0.04 |

TABLE 2

Coefficients for the best fits of α7 wild type, Chim I, and Chim II

| Receptor Type | CT | | 30 μM IVM | | 1 mM 5-HI | | 10 μM NS-1708 | | 10 μM PNU-120586 | |
|---|---|---|---|---|---|---|---|---|---|---|
| | $EC_{50}$ μM | $n_g$ | $EC_{50}$ μM | $n_g$ | $EC_{50}$ μM | $n_g$ | $EC_{50}$ μM | $n_g$ | $EC_{50}$ μM | $n_g$ |
| α7 | 146 ± 11 n = 5 | 1.7 ± 0.06 | 18.7 ± 1.8 n = 3 | 1.4 ± 0.16 | 72 ± 81 n = 3 | 1.97 ± 0.84 | 84 ± 7 n = 5 | 2.06 ± 0.55 | 12 ± 9 n = 4 | 1.2 ± 0.66 |
| Chim I | 71 ± 10 n = 4 | 1.35 ± 0.14 | 78 ± 6.3 n = 3 | 1.8 ± 0.05 | 76 ± 6.9 n = 3 | 1.4 ± 0.13 | 6 ± 1.5 n = 3 | 1.5 ± 0.09 | 64.7 ± 6.8 n = 3 | 1.2 ± 0.1 |
| Chim II[a] | 22 ± 1.6 n = 4 | 1 ± 0.04 | 17.8 ± 2.4 n = 4 | 1.1 ± 0.12 | 8 ± 8 n = 4 | 1.35 ± 0.25 | 1.6 ± 0.8 n = 4 | 0.71 ± 0.06 | 18.8 ± 6.8 n = 4 | 0.94 ± 0.02 |

CT, control.
[a] A concentration of 1 μM PNU-120586 was used for chimera II (Chim II)

TABLE 3

Effects of the modulators on the ACh sensitivity of the α7 wild-type receptor and the chimeras

| Receptor Type | CT | | 10 μM NS-1708 | | 1 μM PNU-120586 | |
|---|---|---|---|---|---|---|
| | $EC_{50}$ μM | $n_g$ | $EC_{50}$ μM | $n_g$ | $EC_{50}$ μM | $n_g$ |
| α7 | 146 ± 11 n = 5 | 1.7 ± 0.06 | 34 ± 7 n = 5 | 2.06 ± 0.65 | 59 ± 9 n = 4 | 1.2 ± 0.1 |
| I | 74 ± 6.5 n = 5 | 1.85 ± 0.14 | 17 ± 5 n = 5 | 1.5 ± 0.08 | 64.7 ± 6.8 n = 3 | 1.2 ± 0.1 |
| II | 22 ± 1.6 n = 4 | 1 ± 0.04 | 1 ± 0.37 n = 4 | 0.67 ± 0.08 | 18.8 ± 6.8 n = 4 | 0.04 ± 0.02 |
| III | 31 ± 12 n = 4 | 1.2 ± 0.17 | 4.8 ± 2.4 n = 5 | 0.67 ± 0.08 | 25.9 ± 8.1 n = 4 | 1.1 ± 0.08 |
| IV | 86 ± 16 n = 8 | 1.45 ± 0.1 | 16 ± 2 n = 6 | 0.67 ± 0.08 | 70 ± 31 n = 3 | 1.53 ± 0.13 |
| V | 19 ± 8 n = 8 | 1.48 ± 0.04 | 1.9 ± 1 n = 7 | 1.24 ± 0.04 | 23.5 ± 2.5 n = 4 | 0.95 ± 0.1 |
| VI | 16.5 ± 3.4 n = 8 | 0.63 ± 0.13 | 0.97 ± 0.1 n = 8 | 0.94 ± 0.07 | 29 ± 8.7 n = 2 | 1.16 ± 0.29 |
| VII | 112 ± 6.5 n = 7 | 1.4 ± 0.02 | 15.9 ± 0.63 n = 7 | 1.59 ± 0.06 | 98 ± 8.7 n = 3 | 1.31 ± 0.01 |

TABLE 4

Summary of agonist potencies in chimeras, wild-type α7 and 5-$HT_{3A}$ receptors.

| | Chimera 1 | Chimera 2 | α7 | 5-$HT_{3A}$ |
|---|---|---|---|---|
| | Two electrode voltage clamp, *Xenopus* oocyte: $EC_{50}$ (95% C.I.), μM | | | |
| ACh | 128.0 (97.6-167.7) | 38.1[a,b] (26.2-55.2) | 127.1 (103.5-155.9) | ~30% at 10,000 |
| Choline | 1513 (1050-2180) | 214.5[a,b] (144.1-319.3) | 1122.0 (903.0-1394.0) | No effect at 10,000 |
| | Membrane potential imaging: $EC_{50}$ (95% C.I.), μM | | | |
| ACh | 19.5 (15.4-24.6) | 3.9[a] (3.3-4.6) | | |
| Choline | 285.0 (233.9-347.2) | 37.8[a] (31.4-45.6) | | |
| NS6784 | 0.133 (0.091-0.193) | 0.072[a] (0.058-0.090) | | |
| PNU-282987 | 0.204 (0.146-0.286) | 0.053[a] (0.036-0.076) | | |

Each data-point is n = 3-11.
[a] Indicates statistical difference (P < 0.05) for chimera 2 vs chimera 1.
[b] Depicts statistical difference (P < 0.05) for chimera 2 vs α7.

TABLE 5

Summary of genistein and 5-HI positive allosteric modulation potencies on agonist-evoked responses in the chimeras, wild-type α7 and 5-HT$_{3A}$ receptors.

| | Chimera 1 | Chimera 2 | α7 | 5-HT$_{3A}$ |
|---|---|---|---|---|
| Two electrode voltage clamp, *Xenopus* oocyte: EC$_{50}$ (95% C.I.), μM | | | | |
| Genistein | ~35%[a] at 100 | 5.2 (2.5-10.3) | 10.6 (7.9-14.2) | ~48%[a] at 30 |
| 5-HI | 499.7 (301.8-827.3) | 496.2 (184.3-1337) | 666.9 (496.1-896.4) | ~42%[a] at 10,000 |
| FMP Imaging: EC$_{50}$ (95% C.I.), μM | | | | |
| Genistein | 23.3[a] (12.8-42.3) | 4.3 (1.4-12.7) | | |
| 5-HI | 233.6 (107.4-508.2) | 324.2 (243.2-432.3) | | |

[a]Indicates inhibition (IC$_{50}$ or observed % inhibitory effect at the specified concentration), each data-point is n = 3-12.

What is claimed is:

1. A recombinant nucleic acid encoding a cholinergic/serotoninergic chimeric receptor, wherein the nucleic acid comprises SEQ ID NO:2.

2. The nucleic acid of claim 1, wherein the nucleic acid encodes a polypeptide having an amino acid sequence as set forth in SEQ ID NO:10.

3. A vector comprising the recombinant nucleic acid of claim 1.

4. The vector of claim 3, wherein the recombinant nucleic acid is operably linked to control sequences recognized by a host cell transformed with the vector.

5. A host cell comprising the vector of claim 4.

6. A method of producing a cholinergic/serotoninergic chimeric receptor comprising transforming a host cell with the vector of claim 3.

7. A method for identifying a ligand to a cholinergic/serotoninergic chimeric receptor comprising the amino acid sequence of SEQ ID NO:10, wherein the method comprises contacting the cholinergic/serotoninergic chimeric receptor with a test compound, or a test compound and a positive allosteric modulator, and measuring a response of the cholinergic/serotoninergic chimeric receptor to the test compound, wherein a measurable response of the cell indicates that the test compound is a ligand to the cholinergic/serotoninergic chimeric receptor.

8. The method of claim 7, wherein the cholinergic/serotoninergic chimeric receptor's response to the compound is measured by a binding assay or an electrophysiological assay.

9. The method of claim 7, wherein the compound is selected from the group consisting of a human neuronal nicotinic cholinergic $\alpha 7$ agonist and a human neuronal nicotinic cholinergic $\alpha 7$ antagonist.

10. The method of claim 7, wherein the positive allosteric modulator is a type I positive allosteric modulator or a type II positive allosteric modulator.

* * * * *

SEQUENCE LISTING

<160> NUMBER OF SEQ ID NOS: 37

<210> SEQ ID NO 1
<211> LENGTH: 1401
<212> TYPE: DNA
<213> ORGANISM: Homo sapiens

<400> SEQUENCE: 1

```
atgcgctgct cgccgggagg cgtctggctg gctctggccg cgtcgctgct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga aagaaccaa gttttaacca ccaacatttg gctgcaaatg     240
tcttggacag atcactattt acagtggaat gtgtcagaat atccaggggt gaagactgtt     300
cgtttcccag atggccagat ttggaaacca gacattcttc tctataacag tgctgatgag     360
cgctttgacg ccacattcca cactaacgtg ttggtgaatt cttctgggca ttgccagtac     420
ctgcctccag gcatattcaa gagttcctgc tacatcgatg tacgctggtt tccctttgat     480
gtgcagcact gcaaactgaa gtttgggtcc tggtcttacg gaggctggtc cttggatctg     540
cagatgcagg aggcagatat cagtggctat atccccaatg gagaatggga cctagtggga     600
atccccggca agaggagtga aaggttctat gagtgctgca agagcccta ccccgatgtc     660
accttcacag tggtcatccg acgtaggcca ctcttctatg tggtcagcct gctactgccc     720
agcatcttcc tcatggtcat ggacatcgtg ggcttctacc tgccccccaa cagtggcgag     780
agggtctctt tcaagattac actcctcctg ggctactcgg tcttcctgat catcgtttct     840
gacacgctgc cggccactgc catcggcact cctctcattg gtgtctactt tgtggtgtgc     900
atggctctgc tggtgataag tttggccgag accatcttca ttgtgcggct ggtgcacaag     960
caagacctgc agcagcccgt gcctgcttgg ctgcgtcacc tggttctgga gagaatcgcc    1020
tggctacttt gcctgaggga gcagtcaact tcccagaggc ccccagccac ctcccaagcc    1080
accaagactg atgactgctc agccatggga aaccactgca gccacatggg aggaccccag    1140
gacttcgaga gagcccgag ggacagatgt agccctcccc caccacctcg ggaggcctcg    1200
ctggcggtgt gtgggctgct gcaggagctg tcctccatcc ggcaattcct ggaaaagcgg    1260
gatgagatcc gagaggtggc ccgagactgg ctgcgcgtgg gctccgtgct ggacaagctg    1320
ctattccaca tttacctgct agcggtgctg cctacagca tcaccctggt tatgctctgg    1380
tccatctggc agtacgcttg a                                               1401
```

```
<210> SEQ ID NO 2
<211> LENGTH: 1401
<212> TYPE: DNA
<213> ORGANISM: Homo sapiens

<400> SEQUENCE: 2
atgcgctgct cgccgggagg cgtctggctg gctctggccg cgtcgctgct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga agaaccaa gttttaacca ccaacatttg gctgcaaatg       240
tcttggacag atcactattt acagtggaat gtgtcagaat atccagggggt gaagactgtt    300 cgtttcccag atggccagat ttggaaacca gacattcttc tctataacag tgctgatgag    360
cgctttgacg ccacattcca cactaacgtg ttggtgaatt cttctgggca ttgccagtac    420
ctgcctccag gcatattcaa gagttcctgc tacatcgatg tacgctggtt tcccttgat     480 gtgcagcact gcaaactgaa gtttgggtcc tggtcttacg gaggctggtc cttggatctg    540
cagatgcagg aggcagatat cagtggctat atccccaatg agaatgggga cctagtggga    600
atccccggca gaggagtga aaggttctat gagtgctgca aagagcccta ccccgatgtc    660
accttcacag tggtcatccg acgtaggcca ctcttctatg tggtcagcct gctactgccc    720
agcatcttcc tcatggtcat ggacatcgtg ggcttctacc tgcccccaa cagtggcgag    780 agggtctctt tcaagattac actcctcctg ggctactcgg tcttcctgat catcgttgct    840
gagatcatgc ccgcaacatc cgattcgact cctctcattg tgtctacttt tgtggtgtgc    900
atggctctgc tggtgataag tttggccgag accatcttca ttgtgcggct ggtgcacaag    960
caagacctgc agcagcccgt gcctgcttgg ctgcgtcacc tggttctgga gagaatcgcc   1020
tggctacttt gcctgaggga gcagtcaact tcccagaggc cccagccac ctcccaagcc    1080 accaagactg atgactgctc agccatggga aaccactgca gccacatggg aggaccccag   1140
gacttcgaga agagcccgag ggacagatgt agccctcccc caccacctcg ggaggcctcg   1200
ctggcggtgt gtgggctgct gcaggagctg tcctccatcc ggcaattcct ggaaaagcgg   1260
gatgagatcc gagaggtggc ccgagactgg ctgcgcgtgg gctccgtgct ggacaagctg   1320
ctattccaca tttacctgct agcggtgctg gcctacagca tcaccctggt tatgctctgg   1380
tccatctggc agtacgcttg a                                               1401

<210> SEQ ID NO 3
<211> LENGTH: 1419
<212> TYPE: DNA
<213> ORGANISM: Homo sapiens

<400> SEQUENCE: 3
atgcgctgct cgccgggagg cgtctggctg gctctggccg cgtcgctgct gcacgtgtcc      60
ctgcaaggcg agttccagag gaagctttac aaggagctgg tcaagaacta caatcccttg     120
gagaggcccg tggccaatga ctcgcaacca ctcaccgtct acttctccct gagcctcctg     180
cagatcatgg acgtggatga agaaccaa gttttaacca ccaacatttg gctgcaaatg       240
tcttggacag atcactattt acagtggaat gtgtcagaat atccagggggt gaagactgtt    300 cgtttcccag atggccagat ttggaaacca gacattcttc tctataacag tgctgatgag    360
cgctttgacg ccacattcca cactaacgtg ttggtgaatt cttctgggca ttgccagtac    420
ctgcctccag gcatattcaa gagttcctgc tacatcgatg tacgctggtt tcccttgat     480
```

```
gtgcagcact gcaaactgaa gtttgggtcc tggtcttacg gaggctggtc cttggatctg      540
cagatgcagg aggcagatat cagtggctat atccccaatg gagaatggga cctagtggga      600
atccccggca agaggagtga aaggttctat gagtgctgca aagagcccta ccccgatgtc      660
accttcacag tggtcatccg acgtaggcca ctcttctatg tggtcagcct gctactgccc      720
agcatcttcc tcatggtcat ggacatcgtg ggcttctacc tgcccccaa cagtggcgag       780 agggtctctt tcaagattac actcctcctg ggctactcgg tcttcctgat catcgttgct      840
gagatcatgc ccgcaacatc cgattcgact cctctcattg gtgtctactt tgtggtgtgc      900
atggctctgc tggtgataag tttggccgag accatcttca ttgtgcggct ggtgcacaag      960
caagacctgc agcagcccgt gcctgcttgg ctgcgtcacc tggttctgga gagaatcgcc     1020
tggctacttt gcctgaggga gcagtcaact tcccagaggc ccccagccac ctcccaagcc     1080
accaagactg atgactgctc agccatggga aaccactgca gccacatggg aggacccag     1140 gacttcgaga gagcccgag ggacagatgt agccctcccc caccacctcg ggaggcctcg      1200
ctggcggtgt gtgggctgct gcaggagctg tcctccatcc ggcaattcct ggaaaagcgg     1260
gatgagatcc gagaggtggc ccgagactgg ctgcgcgtgg gctccgtgct ggacaagctg     1320
ctattccaca tttacctgct agcggtgctg gcctacagca tcaccctggt tatgctctgg     1380
tccatctggg tggaggccgt gtccaaagac tttgcgtga                            1419

<210> SEQ ID NO 4
<211> LENGTH: 1491
<212> TYPE: DNA
<213> ORGANISM: Homo sapiens

<400> SEQUENCE: 4
atgcgctgct cgccgggagg cgtctggctg gctctggccg cgtcgctgct gcacgtgtcc       60
ctgcaaggcg agttccagag gaagctttac aaggagctgg tcaagaacta caatcccttg      120
gagaggcccg tggccaatga ctcgcaacca ctcaccgtct acttctccct gagcctcctg      180
cagatcatgg acgtggatga gaagaaccaa gttttaacca ccaacatttg gctgcaaatg      240
tcttggacag atcactattt acagtggaat gtgtcagaat atccaggggt gaagactgtt      300
cgtttcccag atggccagat ttggaaacca gacattcttc tctataacag tgctgatgag      360
cgctttgacg ccacattcca cactaacgtg ttggtgaatt cttctgggca ttgccagtac      420
ctgcctccag gcatattcaa gagttcctgc tacatcgatg tacgctggtt tcccttttgat     480 gtgcagcact gcaaactgaa gtttgggtcc tggtcttacg gaggctggtc cttggatctg      540
cagatgcagg aggcagatat cagtggctat atccccaatg gagaatggga cctagtggga      600
atccccggca agaggagtga aaggttctat gagtgctgca aagagcccta ccccgatgtc      660
accttcacag tggtcatccg acgtaggcca ctcttctatg tggtcagcct gctactgccc      720
agcatcttcc tcatggtcat ggacatcgtg ggcttctacc tgcccccaa cagtggcgag       780 agggtctctt tcaagattac actcctcctg ggctactcgg tcttcctgat catcgtttct      840
gacacgctgc cggccactgc catcggcact cctctcattg gtgtctactt tgtggtgtgc      900
atggctctgc tggtgataag tttggccgag acagtgatcg tgctgcagta ccaccaccac      960
gaccccgacg ggggcaagat gcccaagtgg accagagtca tccttctgaa ctggtgcgcg     1020
tggttcctgc gaatgaagag gccgggggag acaaggtgc gccggcctg ccagcacaag       1080 cagcggcgct gcagcctggc cagtgtggag atgagcgccg tgggcccgcc gcccgccagc     1140
aacgggaacc tgctgtacat cggcttccgc ggcctggacg gcgtgcactg tgtcccgacc     1200
```

```
cccgactctg gggtagtgtg tggccgcatg gcctgctccc ccacgcacga tgagcacctc    1260
ctgcacggcg ggcaacccc cgaggggac cggacttgg ccaagatcct ggaggaggtc      1320
cgctacattg ccaaccgctt ccgctgccag gacgaaagcg aggcggtctg cagcgagtgg   1380
aagttcgccg cctgtgtggt ggacaagctg ctattccaca tttacctgct agcggtgctg   1440
gcctacagca tcaccctggt tatgctctgg tccatctggc agtacgcttg a             1491
```

<210> SEQ ID NO 5
<211> LENGTH: 1491
<212> TYPE: DNA
<213> ORGANISM: Homo sapiens

<400> SEQUENCE: 5

```
atgcgctgct cgccgggagg cgtctggctg gctctggccg cgtcgctgct gcacgtgtcc   60
ctgcaaggcg agttccagag gaagctttac aaggagctgg tcaagaacta caatcccttg   120
gagaggcccg tggccaatga ctcgcaacca ctcaccgtct acttctccct gagcctcctg   180
cagatcatgg acgtggatga agaaccaa gtttaacca ccaacatttg gctgcaaatg      240
tcttggacag atcactattt acagtggaat gtgtcagaat atccagggt gaagactgtt   300 cgtttcccag atggccagat ttggaaacca gacattcttc tctataacag tgctgatgag   360
cgctttgacg ccacattcca cactaacgtg ttggtgaatt cttctgggca ttgccagtac   420
ctgcctccag gcatattcaa gagttcctgc tacatcgatg tacgctggtt tccctttgat   480
gtgcagcact gcaaactgaa gtttgggtcc tggtcttacg gaggctggtc cttggatctg   540
cagatgcagg aggcagatat cagtggctat atccccaatg gagaatggga cctagtggga   600
atccccggca agaggagtga aaggttctat gagtgctgca aagagcccta ccccgatgtc   660
accttcacag tggtcatccg acgtaggcca ctcttctatg tggtcagcct gctactgccc   720
agcatcttcc tcatggtcat ggacatcgtg gccttctacc tgcccccca cagtggcgag   780 agggtctctt tcaagattac actcctcctg ggctactcgg tcttcctgat catcgttgct   840
gagatcatgc ccgcaacatc cgattcgact cctctcattg tgtctactt tgtggtgtgc   900 atggctctgc tggtgataag tttggccgag acagtgatcg tgctgcagta ccaccaccac   960
gaccccgacg gggcaagat gcccaagtgg accagagtca tccttctgaa ctggtgcgcg   1020
tggttcctgc gaatgaagag gcccggggag gacaaggtgc gccggcctg ccagcacaag    1080 cagcggcgct gcagcctggc cagtgtggag atgagcgccg tgggcccgcc gccgccagc    1140 aacgggaacc tgctgtacat cggcttccgc ggcctggacg gcgtgcactg tgtcccgacc   1200
cccgactctg gggtagtgtg tggccgcatg gcctgctccc ccacgcacga tgagcacctc   1260
ctgcacggcg ggcaacccc cgaggggac cggacttgg ccaagatcct ggaggaggtc      1320
cgctacattg ccaaccgctt ccgctgccag gacgaaagcg aggcggtctg cagcgagtgg   1380
aagttcgccg cctgtgtggt ggacaagctg ctattccaca tttacctgct agcggtgctg   1440
gcctacagca tcaccctggt tatgctctgg tccatctggc agtacgcttg a             1491
```

<210> SEQ ID NO 6
<211> LENGTH: 1509
<212> TYPE: DNA
<213> ORGANISM: Homo sapiens

<400> SEQUENCE: 6

```
atgcgctgct cgccgggagg cgtctggctg gctctggccg cgtcgctgct gcacgtgtcc   60
```

```
ctgcaaggcg agttccagag gaagctttac aaggagctgg tcaagaacta caatcccttg    120
gagaggcccg tggccaatga ctcgcaacca ctcaccgtct acttctccct gagcctcctg    180
cagatcatgg acgtggatga agaaccaa gttttaacca ccaacatttg gctgcaaatg     240
tcttggacag atcactattt acagtggaat gtgtcagaat atccagggt gaagactgtt    300 cgtttcccag atggccagat tggaaaacca gacattcttc tctataacag tgctgatgag    360
cgctttgacg ccacattcca cactaacgtg ttggtgaatt cttctgggca ttgccagtac    420
ctgcctccag gcatattcaa gagttcctgc tacatcgatg tacgctggtt tccctttgat    480
gtgcagcact gcaaactgaa gtttgggtcc tggtcttacg gaggctggtc cttggatctg    540
cagatgcagg aggcagatat cagtggctat atccccaatg gagaatggga cctagtggga    600
atccccggca agaggagtga aaggttctat gagtgctgca aagagcccta ccccgatgtc    660
accttcacag tggtcatccg acgtaggcca ctcttctatg tggtcagcct gctactgccc    720
agcatcttcc tcatggtcat ggacatcgtg ggcttctacc tgccccccaa cagtggcgag    780
agggtctctt tcaagattac actcctcctg gctactcgg tcttcctgat catcgttgct    840
gagatcatgc ccgcaacatc cgattcgact cctctcattg gtgtctactt tgtggtgtgc    900
atggctctgc tggtgataag tttggccgag acagtgatcg tgctgcagta ccaccaccac    960
gaccccgacg gggcaagat gcccaagtgg accagagtca tccttctgaa ctggtgcgcg   1020
tggttcctgc gaatgaagag gcccggggag gacaaggtgc gcccggcctg ccagcacaag   1080
cagcggcgct gcagcctggc cagtgtggag atgagcgccg tgggcccgcc gcccgccagc   1140
aacgggaacc tgctgtacat cggcttccgc ggcctggacg gcgtgcactg tgtcccgacc   1200
cccgactctg gggtagtgtg tggccgcatg gcctgctccc ccacgcacga tgagcacctc   1260
ctgcacggcg ggcaaccccc cgaggggac ccggacttgg ccaagatcct ggaggaggtc   1320
cgctacattg ccaaccgctt ccgctgccag gacgaaagcg aggcggtctg cagcgagtgg   1380
aagttcgccg cctgtgtggt ggacaagctg ctattccaca tttacctgct agcggtgctg   1440
gcctacagca tcaccctggt tatgctctgg tccatctggg tggaggccgt gtccaaagac   1500
tttgcgtga                                                           1509
```

<210> SEQ ID NO 7
<211> LENGTH: 1509
<212> TYPE: DNA
<213> ORGANISM: Homo sapiens

<400> SEQUENCE: 7

```
atgcgctgct cgccgggagg cgtctggctg gctctggccg cgtcgctgct gcacgtgtcc     60
ctgcaaggcg agttccagag gaagctttac aaggagctgg tcaagaacta caatcccttg    120
gagaggcccg tggccaatga ctcgcaacca ctcaccgtct acttctccct gagcctcctg    180
cagatcatgg acgtggatga agaaccaa gttttaacca ccaacatttg gctgcaaatg     240
tcttggacag atcactattt acagtggaat gtgtcagaat atccagggt gaagactgtt    300 cgtttcccag atggccagat tggaaaacca gacattcttc tctataacag tgctgatgag    360
cgctttgacg ccacattcca cactaacgtg ttggtgaatt cttctgggca ttgccagtac    420
ctgcctccag gcatattcaa gagttcctgc tacatcgatg tacgctggtt tccctttgat    480
gtgcagcact gcaaactgaa gtttgggtcc tggtcttacg gaggctggtc cttggatctg    540
cagatgcagg aggcagatat cagtggctat atccccaatg gagaatggga cctagtggga    600
atccccggca agaggagtga aaggttctat gagtgctgca aagagcccta ccccgatgtc    660
```

| | | | |
|---|---|---|---|
| accttcacag | tggtcatccg | acgtaggcca ctcttctatg tggtcagcct gctactgccc | 720 |
| agcatcttcc | tcatggtcat | ggacatcgtg ggcttctacc tgccccccaa cagtggcgag | 780 |
| agggtctctt | tcaagattac | actcctcctg ggctactcgg tcttcctgat catcgtttct | 840 |
| gacacgctgc | cggccactgc | catcggcact cctctcattg tgtctacttt gtggtgtgc | 900 |
| atggctctgc | tggtgataag | tttggccgag acagtgatcg tgctgcagta ccaccaccac | 960 |
| gaccccgacg | ggggcaagat | gcccaagtgg accagagtca tccttctgaa ctggtgcgcg | 1020 |
| tggttcctgc | gaatgaagag | gcccggggag acaaggtgc gcccggcctg ccagcacaag | 1080 |
| cagcggcgct | gcagcctggc | cagtgtggag atgagcgccg tgggcccgcc gcccgccagc | 1140 |
| aacgggaacc | tgctgtacat | cggcttccgc ggcctggacg gcgtgcactg tgtcccgacc | 1200 |
| cccgactctg | gggtagtgtg | tggccgcatg gcctgctccc ccacgcacga tgagcacctc | 1260 |
| ctgcacggcg | ggcaaccccc | cgaggggggac ccggacttgg ccaagatcct ggaggaggtc | 1320 |
| cgctacattg | ccaaccgctt | ccgctgccag gacgaaagcg aggcggtctg cagcgagtgg | 1380 |
| aagttcgccg | cctgtgtggt | ggacaagctg ctattccaca tttacctgct agcggtgctg | 1440 |
| gcctacagca | tcaccctggt | tatgctctgg tccatctggg tggaggccgt gtccaaagac | 1500 |
| tttgcgtga | | | 1509 |

<210> SEQ ID NO 8
<211> LENGTH: 1563
<212> TYPE: DNA
<213> ORGANISM: Homo sapiens

<400> SEQUENCE: 8

| | | | |
|---|---|---|---|
| atgcttggaa | agctcgctat | gctgctgtgg gtccagcagg cgctgctcgc cttgctcctc | 60 |
| cccacactcc | tggcacaggg | agaagccagg aggagccgaa acaccaccag gcccgctctg | 120 |
| ctgaggctgt | cggattacct | tttgaccaac tacaggaagg gtgtgcgccc cgtgagggac | 180 |
| tggaggaagc | caaccaccgt | atccattgac gtcattgtct atgccatcct caacgtggat | 240 |
| gagaagaatc | aggtgctgac | cacctacatc tggtaccggc agtactggac tgatgagttt | 300 |
| ctccagtgga | accctgagga | ctttgacaac atcaccaagt tgtccatccc cacggacagc | 360 |
| atctgggtcc | cggacattct | catcaatgag ttcgtggatg tggggaagtc tccaaatatc | 420 |
| ccgtacgtgt | atattcggca | tcaaggcgaa gttcagaact acaagcccct tcaggtggtg | 480 |
| actgcctgta | gcctcgacat | ctacaacttc cccttcgatg tccagaactg ctcgctgacc | 540 |
| ttcaccagtt | ggctgcacac | catccaggac atcaacatct ctttgtggcg cttgccagaa | 600 |
| aaggtgaaat | ccgacaggag | tgtcttcatg aaccagggag agtgggagtt gctgggggtg | 660 |
| ctgcccctact | tcgggagtt | cagcatggaa agcagtaact actatgcaga aatgaagttc | 720 |
| tatgtgacca | tgcgccgcag | gacgctctac tatggcctca acctgctgat ccctgtgtg | 780 |
| ctcatctccg | ccctcgccct | gctggtgttc ctgcttcctg cagattccgg ggagaagatt | 840 |
| tccctgggga | taacagtctt | actctctctt accgtcttca tgctgctcgt ggctgagatc | 900 |
| atgcccgcaa | catccgattc | ggtaccattg atagcccagt acttcgccag caccatgatc | 960 |
| atcgtgggcc | tctcggtggt | ggtgacggtg atcgtgctgc agtaccacca ccacgacccc | 1020 |
| gacggggggca | agatgcccaa | gtggaccaga gtcatcctt tgaactggtg cgcgtggttc | 1080 |
| ctgcgaatga | agaggcccgg | ggaggacaag gtgcgcccgg cctgccagca caagcagcgg | 1140 |
| cgctgcagcc | tggccagtgt | ggagatgagc gccgtggcgc cgccgcccgc cagcaacggg | 1200 |

```
aacctgctgt acatcggctt ccgcggcctg gacggcgtgc actgtgtccc gaccccgac      1260 tctggggtag tgtgtggccg catggcctgc tccccacgc acgatgagca cctcctgcac       1320
ggcgggcaac ccccgaggg ggacccggac ttggccaaga tcctggagga ggtccgctac      1380
attgccaacc gcttccgctg ccaggacgaa agcgaggcgg tctgcagcga gtggaagttc      1440
gccgcctgtg tggtggaccg cctgtgcctc atggccttct cggtcttcac catcatctgc      1500
accatcggca tcctgatgtc ggctcccaac ttcgtggagg ccgtgtccaa agactttgcg     1560
taa                                                                   1563
```

<210> SEQ ID NO 9
<211> LENGTH: 466
<212> TYPE: PRT
<213> ORGANISM: Homo sapiens

<400> SEQUENCE: 9

```
Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
        35                  40                  45

Gln Pro Leu Thr Val Tyr Phe Ser Leu Ser Leu Gln Ile Met Asp
    50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
    130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
        195                 200                 205

Phe Tyr Glu Cys Cys Lys Glu Pro Tyr Pro Asp Val Thr Phe Thr Val
    210                 215                 220

Val Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ala Ile
        275                 280                 285

Gly Thr Pro Leu Ile Gly Val Tyr Phe Val Val Cys Met Ala Leu Leu
    290                 295                 300
```

```
Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
            325                 330                 335

Glu Arg Ile Ala Trp Leu Leu Cys Leu Arg Glu Gln Ser Thr Ser Gln
            340                 345                 350

Arg Pro Pro Ala Thr Ser Gln Ala Thr Lys Thr Asp Cys Ser Ala
            355                 360                 365

Met Gly Asn His Cys Ser His Met Gly Gly Pro Gln Asp Phe Glu Lys
370                 375                 380

Ser Pro Arg Asp Arg Cys Ser Pro Pro Pro Arg Glu Ala Ser
385                 390                 395                 400

Leu Ala Val Cys Gly Leu Leu Gln Glu Leu Ser Ser Ile Arg Gln Phe
            405                 410                 415

Leu Glu Lys Arg Asp Glu Ile Arg Glu Val Ala Arg Asp Trp Leu Arg
            420                 425                 430

Val Gly Ser Val Leu Asp Lys Leu Leu Phe His Ile Tyr Leu Leu Ala
            435                 440                 445

Val Leu Ala Tyr Ser Ile Thr Leu Val Met Leu Trp Ser Ile Trp Gln
450                 455                 460

Tyr Ala
465

<210> SEQ ID NO 10
<211> LENGTH: 466
<212> TYPE: PRT
<213> ORGANISM: Homo sapiens

<400> SEQUENCE: 10

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
            20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
            100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
            180                 185                 190

Asn Gly Glu Trp Asp Leu Val Gly Ile Pro Gly Lys Arg Ser Glu Arg
            195                 200                 205
```

Phe Tyr Glu Cys Cys Lys Glu Pro Tyr Pro Asp Val Thr Phe Thr Val
            210                 215                 220

Val Ile Arg Arg Arg Pro Leu Phe Tyr Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
                260                 265                 270

Ser Val Phe Leu Ile Ile Val Ala Glu Ile Met Pro Ala Thr Ser Asp
            275                 280                 285

Ser Thr Pro Leu Ile Gly Val Tyr Phe Val Val Cys Met Ala Leu Leu
            290                 295                 300

Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
                325                 330                 335

Glu Arg Ile Ala Trp Leu Leu Cys Leu Arg Glu Gln Ser Thr Ser Gln
            340                 345                 350

Arg Pro Pro Ala Thr Ser Gln Ala Thr Lys Thr Asp Asp Cys Ser Ala
            355                 360                 365

Met Gly Asn His Cys Ser His Met Gly Gly Pro Gln Asp Phe Glu Lys
370                 375                 380

Ser Pro Arg Asp Arg Cys Ser Pro Pro Pro Pro Arg Glu Ala Ser
385                 390                 395                 400

Leu Ala Val Cys Gly Leu Leu Gln Glu Leu Ser Ser Ile Arg Gln Phe
                405                 410                 415

Leu Glu Lys Arg Asp Glu Ile Arg Glu Val Ala Arg Asp Trp Leu Arg
            420                 425                 430

Val Gly Ser Val Leu Asp Lys Leu Leu Phe His Ile Tyr Leu Leu Ala
            435                 440                 445

Val Leu Ala Tyr Ser Ile Thr Leu Val Met Leu Trp Ser Ile Trp Gln
450                 455                 460

Tyr Ala
465

<210> SEQ ID NO 11
<211> LENGTH: 472
<212> TYPE: PRT
<213> ORGANISM: Homo sapiens

<400> SEQUENCE: 11

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile

```
            100                 105                 110
Leu Leu Tyr Asn Ser Ala Asp Glu Arg Phe Asp Ala Thr Phe His Thr
        115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
        210                 215                 220

Val Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
            260                 265                 270

Ser Val Phe Leu Ile Ile Val Ala Glu Ile Met Pro Ala Thr Ser Asp
        275                 280                 285

Ser Thr Pro Leu Ile Gly Val Tyr Phe Val Val Cys Met Ala Leu Leu
        290                 295                 300

Val Ile Ser Leu Ala Glu Thr Ile Phe Ile Val Arg Leu Val His Lys
305                 310                 315                 320

Gln Asp Leu Gln Gln Pro Val Pro Ala Trp Leu Arg His Leu Val Leu
                325                 330                 335

Glu Arg Ile Ala Trp Leu Leu Cys Leu Arg Glu Gln Ser Thr Ser Gln
            340                 345                 350

Arg Pro Pro Ala Thr Ser Gln Ala Thr Lys Thr Asp Asp Cys Ser Ala
        355                 360                 365

Met Gly Asn His Cys Ser His Met Gly Gly Pro Gln Asp Phe Glu Lys
        370                 375                 380

Ser Pro Arg Asp Arg Cys Ser Pro Pro Pro Pro Arg Glu Ala Ser
385                 390                 395                 400

Leu Ala Val Cys Gly Leu Leu Gln Glu Leu Ser Ser Ile Arg Gln Phe
                405                 410                 415

Leu Glu Lys Arg Asp Glu Ile Arg Glu Val Ala Arg Asp Trp Leu Arg
            420                 425                 430

Val Gly Ser Val Leu Asp Lys Leu Leu Phe His Ile Tyr Leu Leu Ala
        435                 440                 445

Val Leu Ala Tyr Ser Ile Thr Leu Val Met Leu Trp Ser Ile Trp Val
        450                 455                 460

Glu Ala Val Ser Lys Asp Phe Ala
465                 470

<210> SEQ ID NO 12
<211> LENGTH: 496
<212> TYPE: PRT
<213> ORGANISM: Homo sapiens

<400> SEQUENCE: 12
```

```
Met Arg Cys Ser Pro Gly Gly Val Trp Leu Ala Leu Ala Ala Ser Leu
  1               5                  10                  15

Leu His Val Ser Leu Gln Gly Glu Phe Gln Arg Lys Leu Tyr Lys Glu
             20                  25                  30

Leu Val Lys Asn Tyr Asn Pro Leu Glu Arg Pro Val Ala Asn Asp Ser
             35                  40                  45

Gln Pro Leu Thr Val Tyr Phe Ser Leu Ser Leu Leu Gln Ile Met Asp
 50                  55                  60

Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
            130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
            210                 215                 220

Val Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
            260                 265                 270

Ser Val Phe Leu Ile Ile Val Ser Asp Thr Leu Pro Ala Thr Ala Ile
            275                 280                 285

Gly Thr Pro Leu Ile Gly Val Tyr Phe Val Val Cys Met Ala Leu Leu
            290                 295                 300

Val Ile Ser Leu Ala Glu Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Gln Arg Arg Cys Ser Leu Ala Ser
            355                 360                 365

Val Glu Met Ser Ala Val Ala Pro Pro Ala Ser Asn Gly Asn Leu
            370                 375                 380

Leu Tyr Ile Gly Phe Arg Gly Leu Asp Gly His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
```

```
                420              425              430
Leu Ala Lys Ile Leu Glu Glu Val Arg Tyr Ile Ala Asn Arg Phe Arg
            435              440              445

Cys Gln Asp Glu Ser Glu Ala Val Cys Ser Glu Trp Lys Phe Ala Ala
            450              455              460

Cys Val Val Asp Lys Leu Leu Phe His Ile Tyr Leu Leu Ala Val Leu
465             470              475              480

Ala Tyr Ser Ile Thr Leu Val Met Leu Trp Ser Ile Trp Gln Tyr Ala
            485              490              495

<210> SEQ ID NO 13
<211> LENGTH: 496
<212> TYPE: PRT
<213> ORGANISM: Homo sapiens

<400> SEQUENCE: 13

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
            195                 200                 205

Phe Tyr Glu Cys Cys Lys Glu Pro Tyr Pro Asp Val Thr Phe Thr Val
        210                 215                 220

Val Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
            260                 265                 270

Ser Val Phe Leu Ile Ile Val Ala Glu Ile Met Pro Ala Thr Ser Asp
        275                 280                 285

Ser Thr Pro Leu Ile Gly Val Tyr Phe Val Val Cys Met Ala Leu Leu
        290                 295                 300
```

```
Val Ile Ser Leu Ala Glu Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
            340                 345                 350

Val Arg Pro Ala Cys Gln His Lys Gln Arg Arg Cys Ser Leu Ala Ser
        355                 360                 365

Val Glu Met Ser Ala Val Ala Pro Pro Ala Ser Asn Gly Asn Leu
    370                 375                 380

Leu Tyr Ile Gly Phe Arg Gly Leu Asp Gly Val His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
            420                 425                 430

Leu Ala Lys Ile Leu Glu Glu Val Arg Tyr Ile Ala Asn Arg Phe Arg
        435                 440                 445

Cys Gln Asp Glu Ser Glu Ala Val Cys Ser Glu Trp Lys Phe Ala Ala
    450                 455                 460

Cys Val Val Asp Lys Leu Leu Phe His Ile Tyr Leu Leu Ala Val Leu
465                 470                 475                 480

Ala Tyr Ser Ile Thr Leu Val Met Leu Trp Ser Ile Trp Gln Tyr Ala
                485                 490                 495

<210> SEQ ID NO 14
<211> LENGTH: 502
<212> TYPE: PRT
<213> ORGANISM: Homo sapiens

<400> SEQUENCE: 14

Met Arg Cys Ser Pro Gly Gly Val Trp Leu Ala Leu Ala Ala Ser Leu
1               5                   10                  15

Leu His Val Ser Leu Gln Gly Glu Phe Gln Arg Lys Leu Tyr Lys Glu
                20                  25                  30

Leu Val Lys Asn Tyr Asn Pro Leu Glu Arg Pro Val Ala Asn Asp Ser
            35                  40                  45

Gln Pro Leu Thr Val Tyr Phe Ser Leu Ser Leu Leu Gln Ile Met Asp
        50                  55                  60

Val Asp Glu Lys Asn Gln Val Leu Thr Thr Asn Ile Trp Leu Gln Met
65                  70                  75                  80

Ser Trp Thr Asp His Tyr Leu Gln Trp Asn Val Ser Glu Tyr Pro Gly
                85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
            115                 120                 125

Asn Val Leu Val Asn Ser Ser Gly His Cys Gln Tyr Leu Pro Pro Gly
        130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190
```

```
Asn Gly Glu Trp Asp Leu Val Gly Ile Pro Gly Lys Arg Ser Glu Arg
            195                 200                 205
Phe Tyr Glu Cys Cys Lys Glu Pro Tyr Pro Asp Val Thr Phe Thr Val
    210                 215                 220
Val Ile Arg Arg Pro Leu Phe Tyr Val Val Ser Leu Leu Pro
225                 230                 235                 240
Ser Ile Phe Leu Met Val Met Asp Ile Val Gly Phe Tyr Leu Pro Pro
                245                 250                 255
Asn Ser Gly Glu Arg Val Ser Phe Lys Ile Thr Leu Leu Gly Tyr
            260                 265                 270
Ser Val Phe Leu Ile Ile Val Ala Glu Ile Met Pro Ala Thr Ser Asp
                275                 280                 285
Ser Thr Pro Leu Ile Gly Val Tyr Phe Val Val Cys Met Ala Leu Leu
            290                 295                 300
Val Ile Ser Leu Ala Glu Thr Val Ile Val Leu Gln Tyr His His His
305                 310                 315                 320
Asp Pro Asp Gly Gly Lys Met Pro Lys Trp Thr Arg Val Ile Leu Leu
                325                 330                 335
Asn Trp Cys Ala Trp Phe Leu Arg Met Lys Arg Pro Gly Glu Asp Lys
            340                 345                 350
Val Arg Pro Ala Cys Gln His Lys Gln Arg Arg Cys Ser Leu Ala Ser
            355                 360                 365
Val Glu Met Ser Ala Val Ala Pro Pro Ala Ser Asn Gly Asn Leu
    370                 375                 380
Leu Tyr Ile Gly Phe Arg Gly Leu Asp Gly Val His Cys Val Pro Thr
385                 390                 395                 400
Pro Asp Ser Gly Val Val Cys Gly Arg Met Ala Cys Ser Pro Thr His
                405                 410                 415
Asp Glu His Leu Leu His Gly Gly Gln Pro Pro Glu Gly Asp Pro Asp
            420                 425                 430
Leu Ala Lys Ile Leu Glu Glu Val Arg Tyr Ile Ala Asn Arg Phe Arg
        435                 440                 445
Cys Gln Asp Glu Ser Glu Ala Val Cys Ser Glu Trp Lys Phe Ala Ala
    450                 455                 460
Cys Val Val Asp Lys Leu Leu Phe His Ile Tyr Leu Leu Ala Val Leu
465                 470                 475                 480
Ala Tyr Ser Ile Thr Leu Val Met Leu Trp Ser Ile Trp Val Glu Ala
                485                 490                 495
Val Ser Lys Asp Phe Ala
            500

<210> SEQ ID NO 15
<211> LENGTH: 502
<212> TYPE: PRT
<213> ORGANISM: Homo sapiens

<400> SEQUENCE: 15

Met Arg Cys Ser Pro Gly Gly Val Trp Leu Ala Leu Ala Ala Ser Leu
1               5                   10                  15
Leu His Val Ser Leu Gln Gly Glu Phe Gln Arg Lys Leu Tyr Lys Glu
                20                  25                  30
Leu Val Lys Asn Tyr Asn Pro Leu Glu Arg Pro Val Ala Asn Asp Ser
            35                  40                  45
Gln Pro Leu Thr Val Tyr Phe Ser Leu Ser Leu Leu Gln Ile Met Asp
```

-continued

```
                50                  55                  60
Val Asp Glu Lys Asn Gln Val Leu Thr Thr Asn Ile Trp Leu Gln Met
 65                  70                  75                  80

Ser Trp Thr Asp His Tyr Leu Gln Trp Asn Val Ser Glu Tyr Pro Gly
                 85                  90                  95

Val Lys Thr Val Arg Phe Pro Asp Gly Gln Ile Trp Lys Pro Asp Ile
                100                 105                 110

Leu Leu Tyr Asn Ser Ala Asp Glu Arg Phe Asp Ala Thr Phe His Thr
                115                 120                 125

Asn Val Leu Val Asn Ser Ser Gly His Cys Gln Tyr Leu Pro Pro Gly
130                 135                 140

Ile Phe Lys Ser Ser Cys Tyr Ile Asp Val Arg Trp Phe Pro Phe Asp
145                 150                 155                 160

Val Gln His Cys Lys Leu Lys Phe Gly Ser Trp Ser Tyr Gly Gly Trp
                165                 170                 175

Ser Leu Asp Leu Gln Met Gln Glu Ala Asp Ile Ser Gly Tyr Ile Pro
                180                 185                 190

Asn Gly Glu Trp Asp Leu Val Gly Ile Pro Gly Lys Arg Ser Glu Arg
                195                 200                 205

Phe Tyr Glu Cys Cys Lys Glu Pro Tyr Pro Asp Val Thr Phe Thr Val
210                 215                 220

Val Ile Arg Arg Arg Pro Leu Phe Tyr Val Val Ser Leu Leu Leu Pro
225                 230                 235                 240

Ser Ile Phe Leu Met Val Met Asp Ile Val Gly Phe Tyr Leu Pro Pro
                245                 250                 255

Asn Ser Gly Glu Arg Val Ser Phe Lys Ile Thr Leu Leu Leu Gly Tyr
                260                 265                 270

Ser Val Phe Leu Ile Ile Val Ser Asp Thr Leu Pro Ala Thr Ala Ile
                275                 280                 285

Gly Thr Pro Leu Ile Gly Val Tyr Phe Val Val Cys Met Ala Leu Leu
                290                 295                 300

Val Ile Ser Leu Ala Glu Thr Val Ile Val Leu Gln Tyr His His His
305                 310                 315                 320

Asp Pro Asp Gly Gly Lys Met Pro Lys Trp Thr Arg Val Ile Leu Leu
                325                 330                 335

Asn Trp Cys Ala Trp Phe Leu Arg Met Lys Arg Pro Gly Glu Asp Lys
                340                 345                 350

Val Arg Pro Ala Cys Gln His Lys Gln Arg Arg Cys Ser Leu Ala Ser
                355                 360                 365

Val Glu Met Ser Ala Val Ala Pro Pro Ala Ser Asn Gly Asn Leu
370                 375                 380

Leu Tyr Ile Gly Phe Arg Gly Leu Asp Gly His Cys Val Pro Thr
385                 390                 395                 400

Pro Asp Ser Gly Val Val Cys Gly Arg Met Ala Cys Ser Pro Thr His
                405                 410                 415

Asp Glu His Leu Leu His Gly Gly Gln Pro Pro Glu Gly Asp Pro Asp
                420                 425                 430

Leu Ala Lys Ile Leu Glu Glu Val Arg Tyr Ile Ala Asn Arg Phe Arg
                435                 440                 445

Cys Gln Asp Glu Ser Glu Ala Val Cys Ser Glu Trp Lys Phe Ala Ala
                450                 455                 460

Cys Val Val Asp Lys Leu Leu Phe His Ile Tyr Leu Leu Ala Val Leu
465                 470                 475                 480
```

```
Ala Tyr Ser Ile Thr Leu Val Met Leu Trp Ser Ile Trp Val Glu Ala
                485                 490                 495

Val Ser Lys Asp Phe Ala
            500
```

<210> SEQ ID NO 16
<211> LENGTH: 520
<212> TYPE: PRT
<213> ORGANISM: Homo sapiens

<400> SEQUENCE: 16

```
Met Leu Gly Lys Leu Ala Met Leu Leu Trp Val Gln Gln Ala Leu Leu
1               5                   10                  15

Ala Leu Leu Leu Pro Thr Leu Ala Gln Gly Glu Ala Arg Arg Ser
            20                  25                  30

Arg Asn Thr Thr Arg Pro Ala Leu Leu Arg Leu Ser Asp Tyr Leu Leu
        35                  40                  45

Thr Asn Tyr Arg Lys Gly Val Arg Pro Val Arg Asp Trp Arg Lys Pro
    50                  55                  60

Thr Thr Val Ser Ile Asp Val Ile Val Tyr Ala Ile Leu Asn Val Asp
65                  70                  75                  80

Glu Lys Asn Gln Val Leu Thr Thr Tyr Ile Trp Tyr Arg Gln Tyr Trp
                85                  90                  95

Thr Asp Glu Phe Leu Gln Trp Asn Pro Glu Asp Phe Asp Asn Ile Thr
            100                 105                 110

Lys Leu Ser Ile Pro Thr Asp Ser Ile Trp Val Pro Asp Ile Leu Ile
        115                 120                 125

Asn Glu Phe Val Asp Val Gly Lys Ser Pro Asn Ile Pro Tyr Val Tyr
    130                 135                 140

Ile Arg His Gln Gly Glu Val Gln Asn Tyr Lys Pro Leu Gln Val Val
145                 150                 155                 160

Thr Ala Cys Ser Leu Asp Ile Tyr Asn Phe Pro Phe Asp Val Gln Asn
                165                 170                 175

Cys Ser Leu Thr Phe Thr Ser Trp Leu His Thr Ile Gln Asp Ile Asn
            180                 185                 190

Ile Ser Leu Trp Arg Leu Pro Glu Lys Val Lys Ser Asp Arg Ser Val
        195                 200                 205

Phe Met Asn Gln Gly Glu Trp Glu Leu Leu Gly Val Leu Pro Tyr Phe
    210                 215                 220

Arg Glu Phe Ser Met Glu Ser Ser Asn Tyr Tyr Ala Glu Met Lys Phe
225                 230                 235                 240

Tyr Val Thr Met Arg Arg Arg Thr Leu Tyr Tyr Gly Leu Asn Leu Leu
                245                 250                 255

Ile Pro Cys Val Leu Ile Ser Ala Leu Ala Leu Leu Val Phe Leu Leu
            260                 265                 270

Pro Ala Asp Ser Gly Glu Lys Ile Ser Leu Gly Ile Thr Val Leu Leu
        275                 280                 285

Ser Leu Thr Val Phe Met Leu Leu Val Ala Glu Ile Met Pro Ala Thr
    290                 295                 300

Ser Asp Ser Val Pro Leu Ile Ala Gln Tyr Phe Ala Ser Thr Met Ile
305                 310                 315                 320

Ile Val Gly Leu Ser Val Val Thr Val Ile Val Leu Gln Tyr His
                325                 330                 335

His His Asp Pro Asp Gly Gly Lys Met Pro Lys Trp Thr Arg Val Ile
```

```
              340             345             350
Leu Leu Asn Trp Cys Ala Trp Phe Leu Arg Met Lys Arg Pro Gly Glu
        355                 360                 365

Asp Lys Val Arg Pro Ala Cys Gln His Lys Gln Arg Arg Cys Ser Leu
        370                 375                 380

Ala Ser Val Glu Met Ser Ala Val Ala Pro Pro Ala Ser Asn Gly
385                 390                 395                 400

Asn Leu Leu Tyr Ile Gly Phe Arg Gly Leu Asp Gly Val His Cys Val
            405                 410                 415

Pro Thr Pro Asp Ser Gly Val Val Cys Gly Arg Met Ala Cys Ser Pro
        420                 425                 430

Thr His Asp Glu His Leu Leu His Gly Gly Gln Pro Pro Glu Gly Asp
        435                 440                 445

Pro Asp Leu Ala Lys Ile Leu Glu Glu Val Arg Tyr Ile Ala Asn Arg
        450                 455                 460

Phe Arg Cys Gln Asp Glu Ser Glu Ala Val Cys Ser Glu Trp Lys Phe
465                 470                 475                 480

Ala Ala Cys Val Val Asp Arg Leu Cys Leu Met Ala Phe Ser Val Phe
            485                 490                 495

Thr Ile Ile Cys Thr Ile Gly Ile Leu Met Ser Ala Pro Asn Phe Val
            500                 505                 510

Glu Ala Val Ser Lys Asp Phe Ala
            515                 520

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccgccatgc gctgctcgcc gggaggcgtc t                              31

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aggctgacca catagaagag tggcctacgt cggatgacca ctgtgaaggt gacatcg    57

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtcaagcgta ctgccagatg gaccaga                                   27

<210> SEQ ID NO 20
<211> LENGTH: 57
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
cgatgtcacc ttcacagtgg tcatccgacg taggccactc ttctatgtgg tcagcct       57

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Glu Ile Met Pro Ala Thr Ser Asp Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Asp Thr Leu Pro Ala Thr Ala Ile Gly
1               5                   10

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacactaacg tgttggtgaa ttctt                                          25

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcggatgttg cgggcatgat ctcagcaacg atgatcagga agaccgagta               50

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gaagttgact gctccctcag gcaa                                           24

<210> SEQ ID NO 26
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 26
atcatgcccg caacatccga ttcgactcct ctcattggtg tctac              45

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Glu Ala Val Ser Lys Asp Phe Ala
1               5

<210> SEQ ID NO 28
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tattccacat ttacctgcta gcggtgctgg cctacagcat caccctggtt atgctctg    58

<210> SEQ ID NO 29
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggccctcac gcaaagtctt tggacacggc ctccacccag atggaccaga gcataaccag    60
ggtga                                                                65

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cacattccac actaacgtgt tggtgaa                                 27

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atgccgtctc ctctcggcca aacttatcac c                            31

<210> SEQ ID NO 32
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atgccgtctc cgagaccgtg atcgtgctgc ag                                    32

<210> SEQ ID NO 33
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
catgctagca ggtaaatgtg aatagcagc ttgtccacca cacaggcgg                    49

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccgccatgc ttggaaagct cgctatgct                                        29

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agcgtcctgc ggcgcatggt cacatagaac ttcatttctg                            40

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gttacgcaaa gtctttggac acggc                                            25

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagaaatgaa gttctatgtg accatgcgcc gcaggacgct                            40
```